Figure 1B:
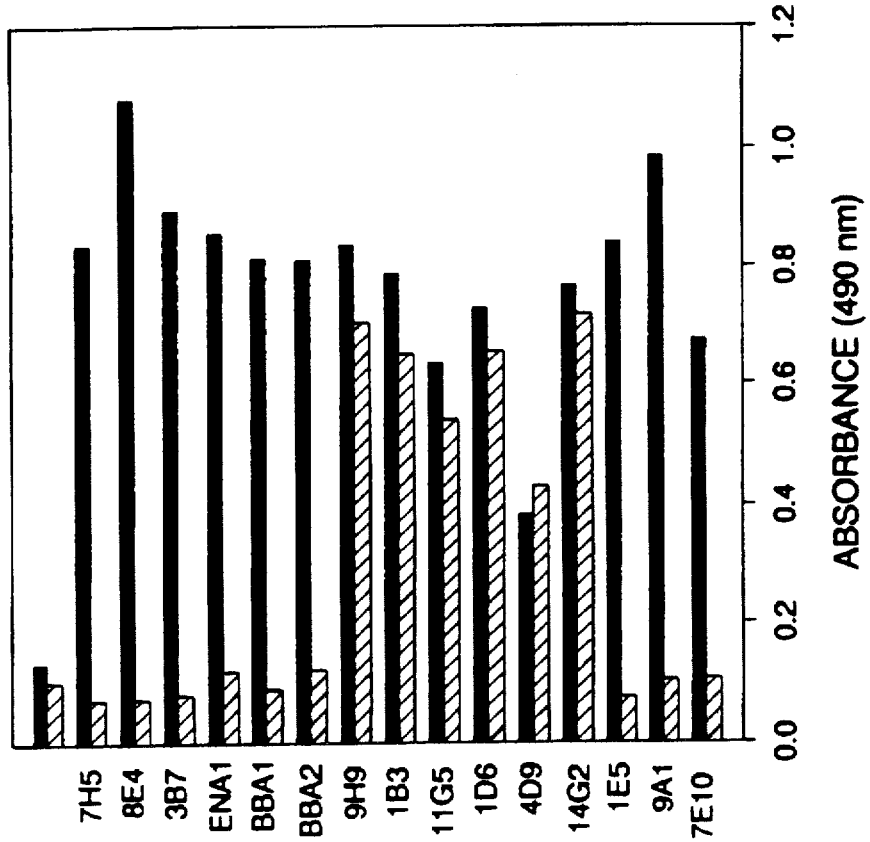

US005593882A

United States Patent [19]
Erbe et al.

[11] Patent Number: 5,593,882
[45] Date of Patent: Jan. 14, 1997

[54] SELECTIN VARIANTS

[75] Inventors: David V. Erbe, San Francisco; Laurence A. Lasky, Sausalito; Leonard G. Presta, San Francisco, all of Calif.

[73] Assignee: Genentech, Inc., South San Francisco, Calif.

[21] Appl. No.: 274,661

[22] Filed: Jul. 13, 1994

Related U.S. Application Data

[63] Continuation of Ser. No. 956,701, Oct. 1, 1992, abandoned, which is a continuation-in-part of Ser. No. 879,036, Apr. 30, 1992, abandoned.

[51] Int. Cl.$^6$ .......................... C12N 5/10; C07K 14/435
[52] U.S. Cl. .................. 435/240.2; 530/395; 536/23.1; 536/23.5; 435/69.1; 435/172.3; 435/252.3; 435/320.1; 514/8; 935/10
[58] Field of Search ............................ 536/23.5, 23.1; 435/69.1, 69.3, 172.1, 172.3, 240.2, 252.3, 320.1; 530/350, 395; 935/10; 514/8

[56] References Cited

U.S. PATENT DOCUMENTS

| | | | |
|---|---|---|---|
| 5,081,034 | 1/1992 | Bevilacqua | 435/252.33 |
| 5,098,833 | 3/1992 | Lasky | 435/69.1 |

FOREIGN PATENT DOCUMENTS

A92/01718  6/1992  WIPO .

OTHER PUBLICATIONS

Berg, E. L. et al., *J. Biol. Chem.* 266, 14869–72 (1991).
Bevilacqua, M. P., et al., *Science* 243, 1160–1165 (1989),
Bevilacqua, P. P. et al., *Proc. Natl. Acad. Sci. USA* 84, 9238–9242 (1987).
Bonfanti, R. et al., *Blood* 73, 1109–1112 (1989).
Brandley, B. et al., *Cell* 63, 861–863 (1990).
Gallatin et al., *Nature* 303, 30–34 (1983).
Imai, Y. et al., *J. Cell Biol.* 113 1213–1221 (1991).
Johnston et al., *Cell* 56, 1033–1044 (1989).
Kuijpers, T. W. et al., *J. Immunol.* 147 1369–1376 (1991).
Larsen, E. et al., *Cell* 59, 305–312 (1989).
Larsen, E. et al., *Cell* 63, 467–474 (1990).
Lasky, L. A. et al., *Cell* (1992), in press and copending U.S. application Ser. No. 07/834,902 filed 13 Feb. 1992.
Lasky, L. A., *Cell* 56, 1045–1055 (1989).
Lawrence, M. B. et al., *Cell*, 65, 859–873 (1991).
Ley, K. et al., *Blood* 77(12), 2553–2555 (1991).
Lowe J. B. et al., *Cell* 63 475–484 (1990).
Luscinkas, F. W. et al., *J. Immunol.*, 142 2257–2263 (1989).
McEver, R. et al., *J. Clin. Inv.* 84, 92–99 (1989).
Moore, K. L. et al., *J. Cell. Biol.* 112, 491–499 (1991).
Phillips, M. L. et al., *Science* 250 1130–1132 (1990).
Picker, L. J. et al., *Nature* 349 796–799 (1991).
Polley, M. J. et al., *Proc. Natl. Acad. Sci. USA* 88, 6224–6228 (1991).
Shimizu, Y. et al., *Nature* 349, 799–802 (1991).
Siegelman, M. et al., *Science* 243, 1165–1172 (1989).
Springer, T. and Lasky, L. A., *Nature* 349 196–197 (1991).
Stoolman, L. M. *Cell* 56; 907–910 (1989).

Tiemeyer, M. et al., *Proc. Natl. Acad. Sci. USA* 88 1138–1142 (1991).
True, D. D., et al., *J .Cell Biol.* 111, 2757–2764 (1990).
Tyrrell, D. et al., *Proc. Natl. Acad. Sci. USA*, 88, 10372–10376 (1991).
Von Andrian, V. et al., *Proc. Natl. Acad. Sci. USA* 88, 7538–7542 (1991).
Walz, G. A. et al., *Science* 250 1132–1135 (1990).
Watson, S. R., *Nature* 349 164–167 (1991).
Weis, W. et al., *Science* 254, 1608–1615 (1985).
Corrall, L. et al., *Biochem. Biphys. Res. Commun.* 172: 1349–1356 (1990).
Mulligan, M. et al., "Protective Effects of Oligosaccharides in P–Selectin–Dependent Lung Injury," *Nature* 364: 149–151 (1993).
Mulligan, M. et al., "Neutrophil–Dependent Acute Lung Injury," *J. Clin. Invest.* 90: 1600–7 (1992).
Watson, S. et al., "Neutrophil Influx Into An Inflammatory Site Inhibited by a Soluble Homing Receptor–IgG Chimaera," *Nature* 349: 164–167 (1991).
Imai et al., *J. Cell. Biol.* 113: 1213–1221 (1991).
G. I. Johnston et al. *Cell* 156:1033–44 Mar. 24, 1989.
B. R. Bowen et al. J. Cell Biology 110:147–53 Jan. 1990.
B C Cunningham et al Science 244:1081 Jun. 2, 1989.
Weis, W. et al., "Structure of the Influenza Virus Haemagglutinin Complexed with Its Receptor, Sialic Acid," *Nature (London)*, 333: 421–431 (1988).
Erbe, D. V., et al., "P– and E–Selectin Use Common sites for Carbohydrate Ligand Recognition and Cell Adhesion," *J. Cell Biol.* 120(5): 1227–1235 (1993).
Erbe, D. V. et al., "Identification of an E–Selectin Region Critical for Carbohydrate Recognition and Cell Adhesion," *J. Cell Biol.* 119(1): 215–227 (1992).
Kansas, G. S., "Structure and Function of L–Selectin," *AMPIS* 100(4): 287–293 (1992).
Mills, A., "Modelling the Carbohydrate Recognition Domain of Human E–Selectin," *FEBS Letters* 319(1–2): 5–11 (1993).
Pigott, R. et al., "Structural and Functional Studies of the Endothelial Activation Antigen Endothelial Leucocyte Adhesion Molecule–1 Using A Panel of Monoclonal Antibodies," *J. Immunol.* 147(1): 130–135 (1991).
Sali, A. et al., "From Comparison of Protein Sequences and Structures to Protein Modelling and Design," *TIBS Trends in Biochemical Sciences* 15: 235–240 (1990).
Weis, W. I. et al., "Structure of a C–Type Mannose–Binding Protein Complexed with an Oligosaccharide," *Nature* 360: 127–134 (1992).

*Primary Examiner*—Garnette D. Draper
*Assistant Examiner*—Lorraine M. Spector
*Attorney, Agent, or Firm*—Ginger R. Dreger

[57] ABSTRACT

This invention concerns selectin variants having an amino acid alteration at a site or sites of a selectin lectin domain amino acid sequence within a region defined by binding sites recognized by blocking monoclonal antibodies to the corresponding selectin unaltered in the lectin domain. Nucleotide sequences encoding such variants, expression vectors containing such nucleotide sequences, end host cells transformed with such expression vectors are also within the scope of the invention.

25 Claims, 18 Drawing Sheets
**(4 of 35 Drawings in Color

```
                                                        SEQ. ID. NO.
         E Selectin Lectin Domains
         1                            40
         WSYNTSTEAMTYDEASAYCQQRYTHLVAIQNKEEIEYLNS        36
Human
Rabbit    T  HF  A  N                 D                 37
                                       80
         ILSYSPSYYWIGIRKVNNNVWVWVGTQKPLTEEAKNWAPGE       38
Human
Rabbit     D                 I   H   G                  39
                                       120
         PNNRQKDEDCVEIYIKREKDVGMWNDERCSKKKLALCYTA        40
Human
Rabbit     K NN                P T                      41
```
FIG. 2A
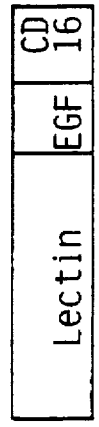
Human E Selectin-CD 16
Rabbit E Selectin-CD 16
HuRa-I
E Selectin-IgG
FIG. 2B

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
      ( A ) LENGTH: 27 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:1:

ATAAGTCATA GCGGCCGTGG AGGTGTT 27

( 2 ) INFORMATION FOR SEQ ID NO:2:

( i ) SEQUENCE CHARACTERISTICS:
      ( A ) LENGTH: 27 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:2:

ACTGGCCTCA TTGGCAGTCA TAGCTTC 27

( 2 ) INFORMATION FOR SEQ ID NO:3:

( i ) SEQUENCE CHARACTERISTICS:
      ( A ) LENGTH: 27 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:3:

CTCATTATAA GTGGCAGCTT CCGTGGA 27

( 2 ) INFORMATION FOR SEQ ID NO:4:

( i ) SEQUENCE CHARACTERISTICS:
      ( A ) LENGTH: 27 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:4:

ATAAGCACTG GCTGCATTAT AAGTCAT 27

( 2 ) INFORMATION FOR SEQ ID NO:5:

( i ) SEQUENCE CHARACTERISTICS:
      ( A ) LENGTH: 27 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:5:

CTCAATCTCT TCTGCGTTTT GAATTGC 27

( 2 ) INFORMATION FOR SEQ ID NO:6:

( i ) SEQUENCE CHARACTERISTICS:
      ( A ) LENGTH: 27 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:6:

ACTTGGTGAA TAGGCCAATA TGGAGTT 27

( 2 ) INFORMATION FOR SEQ ID NO:7:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:7:

ATAACTTGGT GAAGCGCTCA ATATGGA 27

( 2 ) INFORMATION FOR SEQ ID NO:8:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:8:

GTAATAACTT GGTGCATAGC TCAATAT 27

( 2 ) INFORMATION FOR SEQ ID NO:9:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:9:

CCAGTAATAA CTTGCTGAAT AGCTCAA 27

( 2 ) INFORMATION FOR SEQ ID NO:10:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:10:

AATCCAGTAA TAAGCTGGTG AATAGCT 27

( 2 ) INFORMATION FOR SEQ ID NO:11:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:11:

TCCAATCCAG TAAGCACTTG GTGAATA 27

( 2 ) INFORMATION FOR SEQ ID NO:12:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:12:

GATTCCAATC CAGGCATAAC TTGGTGA 27

( 2 ) INFORMATION FOR SEQ ID NO:13:

( i ) SEQUENCE CHARACTERISTICS:
        ( A ) LENGTH: 33 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:13:

TTCTTCTGTC AGAGGCGCCT GGGTTCCTAC CCA 33

( 2 ) INFORMATION FOR SEQ ID NO:14:

( i ) SEQUENCE CHARACTERISTICS:
        ( A ) LENGTH: 36 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:14:

GGGTTCACCT GGCGCCCAGT TCGCGGCTTC TTCTGT 36

( 2 ) INFORMATION FOR SEQ ID NO:15:

( i ) SEQUENCE CHARACTERISTICS:
        ( A ) LENGTH: 39 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:15:

CACGCAGTCC TCATCTGCTT GCGCATTGTT GGGTTCACC 39

( 2 ) INFORMATION FOR SEQ ID NO:16:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:16:

CTTGATGTAG ATGGCCACGC AGTCCTC 27

( 2 ) INFORMATION FOR SEQ ID NO:17:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:17:

TCTCTTGATG TAGGCCTCCA CGCAGTC 27

( 2 ) INFORMATION FOR SEQ ID NO:18:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:18:

TTCTCTCTTG ATGGCGATCT CCACGCA 27

( 2 ) INFORMATION FOR SEQ ID NO:19:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:19:

TTTTCTCTC TTGGCGTAGA TCTCCAC 27

( 2 ) INFORMATION FOR SEQ ID NO:20:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:20:

ATCTTTTCT CTCGCGATGT AGATCTC 27

( 2 ) INFORMATION FOR SEQ ID NO:21:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:21:

CACATCTTTT TCAGCCTTGA TGTAGAT 27

( 2 ) INFORMATION FOR SEQ ID NO:22:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:22:

GCCCACATCT TTGGCTCTCT TGATGTA 27

( 2 ) INFORMATION FOR SEQ ID NO:23:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:23:

CATGCCCACA TCGGCTTCTC TCTTGAT 27

( 2 ) INFORMATION FOR SEQ ID NO:24:

( i ) SEQUENCE CHARACTERISTICS:
    ( A ) LENGTH: 27 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:24:

CCACATGCCC ACGGCTTTTT CTCTCTT 27

( 2 ) INFORMATION FOR SEQ ID NO:25:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:25:

ATTCCACATG CCAGCATCTT TTTCTCT 27

( 2 ) INFORMATION FOR SEQ ID NO:26:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:26:

CTCATCATTC CATGCGCCCA CATCTTT 27

( 2 ) INFORMATION FOR SEQ ID NO:27:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:27:

CTTGCTGCAC CTCGCATCAT TCCACAT 27

( 2 ) INFORMATION FOR SEQ ID NO:28:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:28:

GGCAAGCTTC TTGGCGCTGC ACCTCTC 27

( 2 ) INFORMATION FOR SEQ ID NO:29:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:29:

GCATAGGGCA AGAGCCTTCT TGCTGCA 27

( 2 ) INFORMATION FOR SEQ ID NO:30:

( i ) SEQUENCE CHARACTERISTICS:
        ( A ) LENGTH: 36 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:30:

AGCTTCCGTG GAGTAGTGGT AAGTCCAGGC TCCACT 36

( 2 ) INFORMATION FOR SEQ ID NO:31:

( i ) SEQUENCE CHARACTERISTICS:
    ( A ) LENGTH: 33 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:31:

ATTATAAGTC ATATTTTCCG CGGAGGTGTT GTA    33

( 2 ) INFORMATION FOR SEQ ID NO:32:

( i ) SEQUENCE CHARACTERISTICS:
        ( A ) LENGTH: 33 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:32:

ACTGGCCTCA TTCCAACTGT AAGCTTCCGT GGA    33

( 2 ) INFORMATION FOR SEQ ID NO:33:

( i ) SEQUENCE CHARACTERISTICS:
        ( A ) LENGTH: 36 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:33:

ATTCCACATG CCCGTATCTT TTGGTCTCTT GATGTA    36

( 2 ) INFORMATION FOR SEQ ID NO:34:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:34:

CCAGTTCATG GGGGCTTCAG AATAATG    27

( 2 ) INFORMATION FOR SEQ ID NO:35:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:35:

CCATGAGTAT GCAGCTGTGC TGTAATG    27

( 2 ) INFORMATION FOR SEQ ID NO:36:

( i ) SEQUENCE CHARACTERISTICS:
        ( A ) LENGTH: 120 amino acids
        ( B ) TYPE: Amino Acid
        ( D ) TOPOLOGY: Linear ( x i ) SEQUENCE DESCRIPTION: SEQ ID NO:36:

| Trp | Ser | Tyr | Asn | Thr | Ser | Thr | Glu | Ala | Met | Thr | Tyr | Asp | Glu | Ala |
|---|---|---|---|---|---|---|---|---|---|---|---|---|---|---|
| 1 | | | | 5 | | | | | 10 | | | | | 15 |
| Ser | Ala | Tyr | Cys | Gln | Gln | Arg | Tyr | Thr | His | Leu | Val | Ala | Ile | Gln |
| | | | 20 | | | | | 25 | | | | | 30 | |
| Asn | Lys | Glu | Glu | Ile | Glu | Tyr | Leu | Asn | Ser | Ile | Leu | Ser | Tyr | Ser |
| | | | | 35 | | | | 40 | | | | | 45 | |

```
Pro  Ser  Tyr  Tyr  Trp  Ile  Gly  Ile  Arg  Lys  Val  Asn  Asn  Val  Trp
                     50                      55                          60

Val  Trp  Val  Gly  Thr  Gln  Lys  Pro  Leu  Thr  Glu  Glu  Ala  Lys  Asn
                     65                      70                          75

Trp  Ala  Pro  Gly  Glu  Pro  Asn  Asn  Arg  Gln  Lys  Asp  Glu  Asp  Cys
                     80                      85                          90

Val  Glu  Ile  Tyr  Ile  Lys  Arg  Glu  Lys  Asp  Val  Gly  Met  Trp  Asn
                     95                     100                         105

Asp  Glu  Arg  Cys  Ser  Lys  Lys  Lys  Leu  Ala  Leu  Cys  Tyr  Thr  Ala
                    110                     115                         120
```

( 2 ) INFORMATION FOR SEQ ID NO:37:

( i ) SEQUENCE CHARACTERISTICS:
        ( A ) LENGTH: 120 amino acids
        ( B ) TYPE: Amino Acid
        ( D ) TOPOLOGY: Linear ( x i ) SEQUENCE DESCRIPTION: SEQ ID NO:37:

```
Trp  Thr  Tyr  His  Phe  Ser  Ala  Glu  Asn  Met  Thr  Tyr  Asp  Glu  Ala
  1                   5                      10                          15

Ser  Ala  Tyr  Cys  Gln  Gln  Asn  Tyr  Thr  His  Leu  Val  Ala  Ile  Gln
                     20                      25                          30

Asn  Lys  Glu  Glu  Ile  Asp  Tyr  Leu  Asn  Ser  Ile  Leu  Asp  Tyr  Ser
                     35                      40                          45

Pro  Ser  Tyr  Tyr  Trp  Ile  Gly  Ile  Arg  Lys  Val  Asn  Asn  Val  Trp
                     50                      55                          60

Ile  Trp  Val  Gly  Thr  His  Lys  Pro  Leu  Thr  Glu  Gly  Ala  Lys  Asn
                     65                      70                          75

Trp  Ala  Pro  Gly  Glu  Pro  Asn  Asn  Lys  Gln  Asn  Asn  Glu  Asp  Cys
                     80                      85                          90

Val  Glu  Ile  Tyr  Ile  Lys  Arg  Pro  Lys  Asp  Thr  Gly  Met  Trp  Asn
                     95                     100                         105

Asp  Glu  Arg  Cys  Ser  Lys  Lys  Lys  Leu  Ala  Leu  Cys  Tyr  Thr  Ala
                    110                     115                         120
```

( 2 ) INFORMATION FOR SEQ ID NO:38:

( i ) SEQUENCE CHARACTERISTICS:
        ( A ) LENGTH: 117 amino acids
        ( B ) TYPE: Amino Acid
        ( D ) TOPOLOGY: Linear ( x i ) SEQUENCE DESCRIPTION: SEQ ID NO:38:

```
Trp  Thr  Tyr  His  Tyr  Ser  Glu  Lys  Pro  Met  Asn  Trp  Gln  Arg  Ala
  1                   5                      10                          15

Arg  Arg  Phe  Cys  Arg  Asp  Asn  Tyr  Thr  Asp  Leu  Val  Ala  Ile  Gln
                     20                      25                          30

Asn  Lys  Ala  Glu  Ile  Glu  Tyr  Leu  Glu  Lys  Thr  Leu  Pro  Phe  Ser
                     35                      40                          45

Arg  Ser  Tyr  Tyr  Trp  Ile  Gly  Ile  Arg  Lys  Ile  Gly  Gly  Ile  Trp
                     50                      55                          60

Thr  Trp  Val  Gly  Thr  Asn  Lys  Ser  Leu  Thr  Glu  Glu  Ala  Glu  Asn
                     65                      70                          75

Trp  Gly  Asp  Gly  Glu  Pro  Asn  Asn  Lys  Lys  Asn  Lys  Glu  Asp  Cys
                     80                      85                          90

Val  Glu  Ile  Tyr  Ile  Lys  Arg  Asn  Lys  Asp  Ala  Gly  Lys  Trp  Asn
                     95                     100                         105
```

Asp  Asp  Ala  Cys  His  Lys  Leu  Lys  Ala  Ala  Leu  Cys
               110              115       117

(2) INFORMATION FOR SEQ ID NO:39:

(i) SEQUENCE CHARACTERISTICS:
  (A) LENGTH: 117 amino acids
  (B) TYPE: Amino Acid
  (D) TOPOLOGY: Linear (xi) SEQUENCE DESCRIPTION: SEQ ID NO:39:

Trp  Thr  Tyr  His  Tyr  Ser  Thr  Lys  Ala  Tyr  Ser  Trp  Asn  Ile  Ser
 1              5                        10                      15

Arg  Lys  Tyr  Cys  Gln  Asn  Arg  Tyr  Thr  Asp  Leu  Val  Ala  Ile  Gln
              20                        25                      30

Asn  Lys  Asn  Glu  Ile  Asp  Tyr  Leu  Asn  Lys  Val  Leu  Pro  Tyr  Tyr
              35                        40                      45

Ser  Ser  Tyr  Tyr  Trp  Ile  Gly  Ile  Arg  Lys  Asn  Asn  Lys  Thr  Trp
              50                        55                      60

Thr  Trp  Val  Gly  Thr  Lys  Lys  Ala  Leu  Thr  Asn  Glu  Ala  Glu  Asn
              65                        70                      75

Trp  Ala  Asp  Asn  Glu  Pro  Asn  Asn  Lys  Arg  Asn  Asn  Glu  Asp  Cys
              80                        85                      90

Val  Glu  Ile  Tyr  Ile  Lys  Ser  Pro  Ser  Ala  Pro  Gly  Lys  Trp  Asn
              95                       100                     105

Asp  Glu  His  Cys  Leu  Lys  Lys  Lys  His  Ala  Leu  Cys
              110                      115       117

SELECTIN VARIANTS

This is a continuation of application Ser. No. 07/956,701 filed on 1 Oct. 1992, now abandoned, which is a continuation-in-part of application Ser. No. 07/879,036 filed 30 Apr. 1992 now abandoned. [See XVII below]

BACKGROUND OF THE INVENTION

I. Field of the Invention

This invention relates to selectin variants. The invention further relates to nucleic acids encoding, and to methods and means for preparing these variants.

II. Description of Background and Related Art

The selectins are cell adhesion molecules that are unified structurally by the inclusion of lectin, egf-like and complement binding-like domains [Bevilacqua, M. P., et al., Science 243, 1160–1165 (1989); Johnson, et al., Cell 26, 1033–144 (1989); Lasky, L. A., Cell 56, 1045–1055 (1989); Siegelman, M. et al., Science 243, 1165–1172 (1989); Stoolman, L. M., Cell 56; 907–910 (1989)], and functionally by their ability to mediate cell binding through interactions between their lectin domains and cell surface carbohydrate ligands [Brandley, B., et al. Cell 63, 861–863 (1990); Springer, T., and Lasky, L. A. Nature 349 196–197 (1991)].

Figure 9:
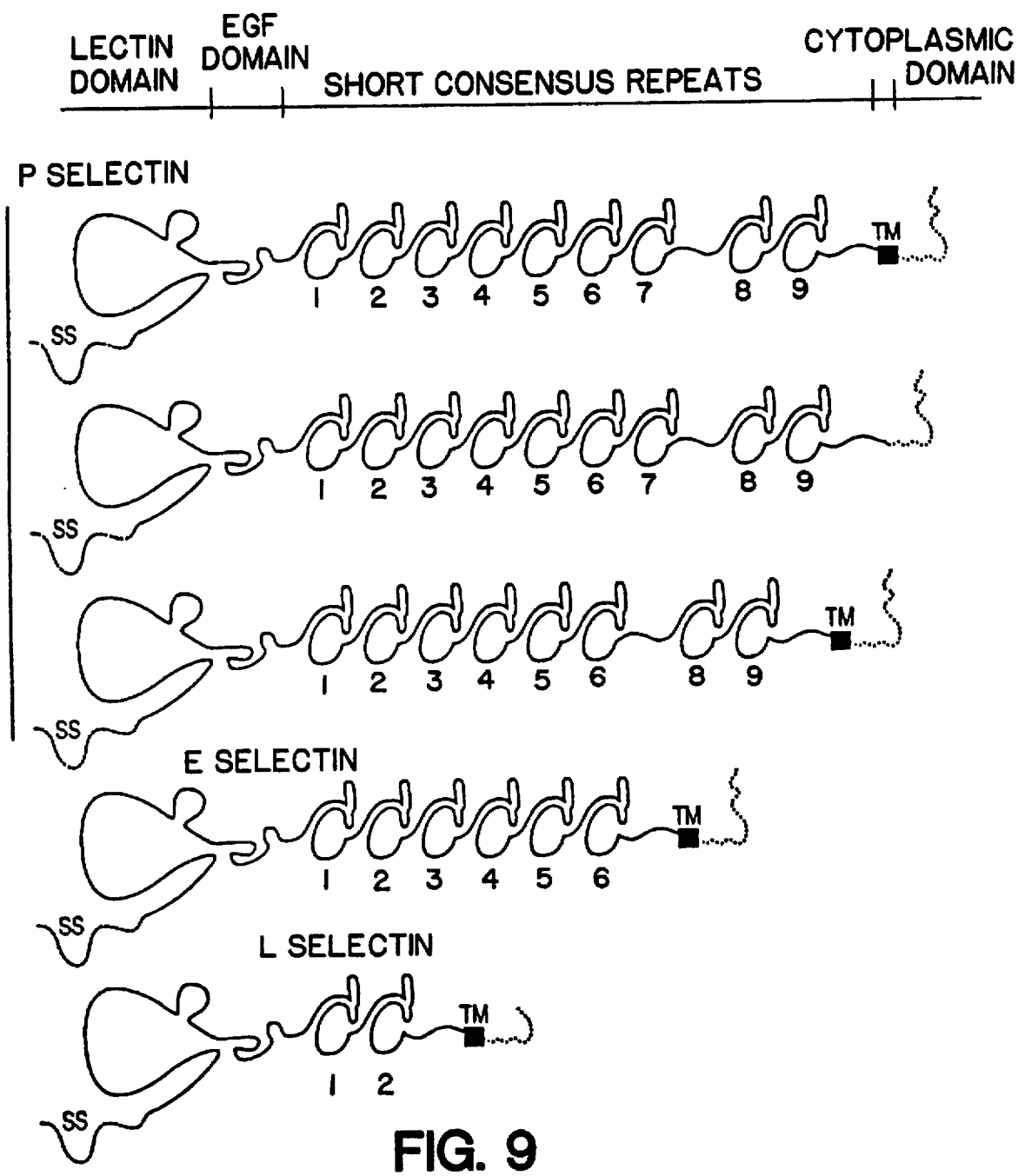

There are three members identified so far in the selectin family of cell adhesion molecules: L-Selectin (a.k.a. peripheral lymph node homing receptor (pnHR), LEC-CAM-1, LAM-1, $gp^{90MEL}$, $gp^{100MEL}$, $gp^{110MEL}$, MEL-14 antigen, Leu-8 antigen, TQ-1 antigen, DREG antigen), E-Selectin (LEC-CAM-2, LECAM-2, ELAM-1) and P-Selectin (LEC-CAM-3, LECAM-3, GMP-140, PADGEM). The structures of the selectin family members are illustrated in FIG. 9.

L-Selectin is found on leukocytes and is involved with the trafficking of lymphocytes to peripheral lymphoid tissues [Gallatin et al., Nature 303, 30–34 (1983)] and with acute neutrophil-mediated inflammatory responses [Watson, S. R., Nature 349 164–167 (1991)]. The amino acid sequence of L-Selectin and the encoding nucleic acid sequence are, for example, disclosed in U.S. Pat. No. 5,098,833 issued 24 Mar. 1992. L-Selectin appears to recognize sialylated, fucosylated, sulfated carbohydrate ligand(s) on at least two endothelial glycoproteins [True, D. D., et al., J. Cell Biol. 111, 2757–2764 (1990); Imai, Y. et al., J. Cell Biol. 113 1213–1221 (1991)], one of which has recently been cloned [Lasky, L. A. et al., Cell (1992), in press and copending U.S. application Ser. No. 07/834,902 filed 13 Feb. 1992].

E-Selectin is an endothelial adhesion molecule that is induced by various inflammatory stimuli [Bevilacqua, P. P. et al., Proc. Natl. Acad. Sci. U.S.A. 84, 9238–9242 (1987); Luscinskas, F. W. et al., J. Immunol. 142 2257–2263 (1989); Kuijpers, T. W. et al., J. Immunol. 147 1369–1376 (1991)]. A cloned gene encoding E-Selectin (ELAM-1) is disclosed in U.S. Pat. No. 5,081,034 issued 14 Jan. 1992. E-Selectin recognizes the neutrophil and monocyte cell surface carbohydrate, sialyl Lewis x (sLex) [Lowe J. B. et al., Cell 63 475–484 (1990); Phillips, M. L. et al., Science 250 1130–1132 (1990); Walz, G. A. et al. Science 250 1132–1135 (1990); Tiemeyer, M. et al., Proc. Natl. Acad. Sci. U.S.A. 88 1138–1142 (1991)], and in addition, may also be involved with the recognition of an sLex-like carbohydrate on the surface of a skin-homing subset of lymphocytes [Picker, L. J. et al., Nature 349 796–799 (1991); Shimizu, Y. et al., Nature 349, 799–802 (1991)]. The minimum sized sLex-related carbohydrate recognized by E-Selectin is a tetrasaccharide of the structure Sialic Acid alpha2-3 Galactose beta 1-4 N-Acetyl Glucosamine (Fucose alpha 1-3) [Tyrrell, D. et al., Proc. Natl. Acad, Sci. U.S.A. 88, 10372–10376 (1991)].

P-Selectin is found in alpha granules of platelets and Weible-Palade bodies of endothelial cells [Bonfanti, R. et al., Blood 73, 1109–1112 (1989); McEver, R. et al., J. Clin. Inv. 84, 92–99 (1989)]. Its surface expression is induced within minutes of exposure to thrombin, substance P, histamine or peroxide, and it appears to recognize a carbohydrate that is either identical to or closely related to sLex on both neutrophil and monocyte cell surfaces [Larsen, E. et al., Cell 59, 305–312 (1989); Larsen, E. et al. Cell 63, 467–474 (1990); Moore, K. L. et al. J. Cell Biol. 112, 491–499 (1991); Polley, M. J. et al., Proc. Natl. Acad. Sci. U.S.A. 88, 6224–6228 (1991)]. The P-Selectin amino acid and the encoding nucleotide sequences are disclosed by Johnston et al., Cell 56, 1033–1044 (1989).

The lectin domains of L-, E- and P-Selectins show remarkable sequence homology and structural similarity. Particularly noteworthy is the conservation of cysteine (Cys) residues at amino acid positions 19, 90, 109 and 117 of the selectin lectin domains, which results in a three dimensional structure comprising two-disulfide bonded loops defined by disulfide bonds formed between Cys19 and Cys117, and Cys90 and Cys109, respectively.

Much evidence has accumulated to indicate similarities in the nature of the carbohydrate ligands seen by selectins. In the case of all three selectins, the adhesive interactions between their lectin domains and carbohydrate ligands require the presence of alpha 2-3 linked sialic acid fucose residues [Brandley, B. et al., Cell 63, 861–863 (1990); Corrall, L. et al., Biochem. Biphys. Res. Commun. 172, 1349–1352 (1990); Springer, T. and Lasky, L. A. Nature 349 196–197 (1991); Tyrrell, D. et al., Proc. Natl. Acad. Sci. U.S.A. 88, 10372–10376 (1991)]. The adhesive interactions between selectin lectin domains and their carbohydrate ligands may be relatively weak, since L- and P-Selectin have been shown to be involved in the relatively low affinity "rolling" of leukocytes along the endothelium during inflammatory responses [Lawrence, M. B. et al., Cell 65, 859–873 (1991); Ley, K. et al. Blood 77 (12), 2553–2555 (1991); Von Andrian, V. et al., Proc. Natl. Acad. Sci. U.S.A. 88, 1538–1542 (1991)].

The molecular details of the interactions between selectin lectin domains and their carbohydrate ligands are poorly understood. The fact that all three selectins require sialic acid for adhesion, when coupled with the finding that certain negatively charged carbohydrate polymers, such as fucoidin, dextran sulfate, and polyphosphomannan ester, are effective inhibitors of some selectin-mediated cell adhesion, is consistent with the involvement of positively-charged amino acids in carbohydrate recognition. However, that such protein-sialic acid interactions can also be Accomplished by non-charged side chains is suggested by crystallographic analysis of the low-affinity interaction between the influenza hemagglutinin glycoprotein, which is not related to type C lectins, and its cell surface ligand, sialic acid, which has revealed that this interaction involves a diversity of amino acid side chains, none of which are positively charged [Weis, W. et al., Science 254, 1608–1615 (1985)]. That a simple face or pocket of the E-, and potentially P- [Polley, M. J. et al., Proc. Natl. Acad. Sci. U.S.A. 88, 6224–6228 (1991)] Selectin lectin domain is involved with the recognition of sLex is suggested by NMR solution analyses of the sLex structure which demonstrate that the critical sialic acid and fucose residues both point to one face of this carbohydrate ligand and are separated by ~10 angstroms, while an inactive form of this carbohydrate (with a 2–6 linked sialic acid) has these two important functional components pointing in very different directions. A similar structural analysis of another ligand for E-Selectin, sialyl Lewis a (sLea: Sialic Acid alpha 2-3 Galactose beta 1-3 N-Acetyl Glucosamine (Fucose alpha 1-4)), has revealed that the critical sialic acid and fucose residues again point to one face of the tetrasaccharide and are separated by approximately the same distance as they are in sLex. See Berg, E. L. et al. *J. Biol. Chem.* 265, 14869–72 (1991); Tyrrell, D. et al. (1991), Supra.

An object of the present invention is to identify the region(s) within the amino acid sequence of selectin lectin domains that is/are critical for the interaction of selectin receptors and their ligands.

It is another object to enable the preparation of amino acid sequence variants of selectins having improved ligand binding properties, in particular increased affinity for their respective ligands as compared to the corresponding native selectin receptors.

A further object is to identify selectin lectin domain sequences that are not critical for the interaction of selectins and their respective ligands.

It is another object to provide selectin amino acid sequence variants with improved pharmacological characteristics, e.g. increased physical and/or chemical stability, increased half-life, decreased rate of in vivo clearance, decreased severity or occurrence of side effects during therapeutic use, etc., having retained or increased ligand binding affinity as compared to the corresponding native selectin.

Selectin variants with enhanced ligand binding properties have great therapeutic potential as effective inhibitors of pathologic inflammatory responses mediated by selectins by blocking the selectin-selectin ligand interaction.

These and further objects of the present invention will be apparent for one skilled in the art.

SUMMARY OF THE INVENTION

The adhesive interactions between sLex and selectin lectin domains were analyzed following two strategies. In the first, chimeric human-rabbit selectin lectin domains were generated based upon amino acid sequence differences between the two species. These chimeras have then been used to map epitopes recognized by anti-human selectin blocking monoclonal antibodies (Mabs). In the second, selectin point mutants were generated and analyzed for binding to a panel of blocking and non-blocking anti-selectin Mabs and for their ability to adhere to immobilized sLex glycolipid. Residues affecting various aspects of selectin structure and/or function have then been superimposed onto a three-dimensional model of the selectin lectin domains that has been generated using the structural coordinates determined for a related C type lectin, the mannose binding protein [Weiss, W. et al., *Science* 254 1608–1615 (1991)]. Together, these data define a relatively small region within the selectin lectin domain that is critical for recognition of the carbohydrate ligand, sLex.

It has been found that the selectin amino acid residues primarily involved with carbohydrate recognition are within a patch on the surface of the lectin domain near the antiparallel beta sheet formed by the disulfide-linked N- and C-termini and the conformationally adjacent disulfide loop formed by the two internal cysteines. Accordingly, sLex is apparently recognized by a relatively small region of the selectin lectin domain, comprised of residues from the N- and C-termini and the small disulfide-bonded loop.

It has further been found that positively-charged amino acid side chains have an essential role in the recognition of carbohydrate ligands of selectins.

It has additionally been found that the replacement of charged amino acid residues by uncharged residues in the N-terminal region of selectins increase the binding affinity of selectins to their respective carbohydrate ligands.

In one aspect, the present invention provides a selectin amino acid sequence variant having an amino acid alteration at a site or sites of the selectin lectin domain recognized by blocking monoclonal antibodies to the corresponding unaltered selectin.

In a preferred embodiment, the amino acid alteration is at a site or sites within a patch comprising amino acids on the surface of the lectin domain near the antiparallel beta strand formed by the disulfide-linked N- and C-termini of the lectin domain and the amino acids of the adjacent disulfide loop formed by the two internal cysteines of the lectin domain.

In one particularly preferred embodiment, the amino acid alteration is within the patch defined by amino acid residue numbers 1–9, and 90 to the C-terminus of the lectin domain of the corresponding native selectin.

In a further preferred embodiment, the amino acid alteration is within the three dimensional patch defined by amino acid residue numbers 7–9, 90–109 and 113 of the lectin domain of the corresponding native selectin.

In an even more preferred embodiment, the alteration is at one or more of amino acid positions 7–9, 43–48, 82–86, 94–100 and 113 of the corresponding native human selectin.

In a still further preferred embodiment, the amino acid alteration is at amino acid residue numbers 7–9, or 84–86, and most preferably at amino acid residue number 8 or at amino acid residues 84 and 86.

In all cases, the amino acid alteration preferably is substitution.

In a particularly preferred embodiment, the amino acid alteration is the substitution of an small uncharged amino acid for a charged amino acid at amino acid residue number 8 of the lectin domain of the corresponding native selectin.

The variants preferably have a positively charged amino acid at at least one of the amino acid positions 97, 111 and 113 of the lectin domain of the corresponding native selectin.

In a still further preferred embodiments, the selectin amino acid sequence variants herein retain the egf like domain of a corresponding selectin.

In other embodiments, this invention relates to a nucleic acid sequence encoding the selectin variant described above, replicable expression vectors comprising and capable of expressing the nucleic acid sequence in a transformant host cell, and microorganisms and cell cultures transformed with the vector.

In a still further embodiment, the invention provides a method comprising:

(a) introducing an amino acid alteration into a selectin lectin domain at a site or sites recognized by blocking monoclonal antibodies to the corresponding unaltered selectin; and (b) screening the resultant selectin variant for enhanced binding affinity to a corresponding selectin ligand.

The selectin variants of the present invention with enhanced binding affinity for their respective native ligands can be used to block the binding of a corresponding native selectin to its ligand, and accordingly, are useful as inhibitors of pathologic inflammatory responses mediated by selectins. For example, such L-Selectin variants (L-Selectin agonists) effectively block the binding of the L-Selectin on a circulating leukocyte to its native ligand on an endothelial cell. This property is useful for treating a symptom or condition associated with excessive binding of circulating leukocytes to endothelial cells, such as inflammation associated with rheumatoid arthritis, psoriasis, multiple sclerosis, etc.

Accordingly, the present invention also provides a method for the treatment or prevention of a symptom or condition associated with a pathologic inflammatory response mediated by a selectin comprising administering to a patient having or at risk to develop such symptom or condition a therapeutically effective amount of a selectin amino acid sequence variant having enhanced ligand binding affinity.

The selectin variants of the present invention can be formulated according to known methods to prepare pharmaceutically useful compositions, whereby the variant is combined in admixture with a pharmaceutically acceptable carrier. Such pharmaceutical compositions are within the scope of the present invention.

The present invention further concerns chimeric proteins comprising a fusion of an amino acid sequence comprising a selectin lectin domain sequence with an alteration as hereinabove described (preferably along with egf like domain and short concensus repeat (SCR) sequences) to an immunoglobulin constant domain sequence.

In a further aspect, the present invention provides a hybrid selectin comprising a portion of a selectin from an animal species with complementary part or parts or a different type of selectin of the same animal species or of the same type of selectin of a different animal species.

In a still further aspect, this invention relates to an anti-E-Selectin monoclonal antibody composition capable of binding to substantially the same E-Selectin lectin domain epitope recognized by or which compete with, a monoclonal antibody selected from the group consisting of 7H5; 8E4; 3B7; 1D6; 4D9; 1E5; 9A1; 7E10;1B3; 14G2; 11G5; and 9H9.

Selectin variants having reduced affinity for their native ligand are useful in screening assays for substances (e.g., peptides, fermentation broth components, carbohydrate derivatives and the like) capable of blocking or enhancing the binding of the selectin with its ligand. In one embodiment, the ability of the substance to be tested to bind to the variant selectin is determined. If it is substantially unable to bind to the variant selectin and to the ligand, but does affect the binding of native selectin to its ligand, then one may conclude that it interacts with the selectin at residues instrumental in ligand binding. Such substances are of particular interest as antagonists of selectin-ligand binding.

In another embodiment, the selectin variants are used to immunize animals so as to identify antibodies that bind to other domains of the selectin.

In an additional embodiment, the variants are used to screen for other antibodies that bind specifically to the ligand binding domain of the selectin. In this embodiment, antibodies raised against the native selectin are screened for their ability to bind to the selectin variant of this invention. Antibodies that substantially do not bind to a variant of this invention are selected as being capable of binding to the ligand binding site. Other diagnostic embodiments will be apparent to the ordinary artisan.

The file of this patent contains at least one drawing executed in color. Copies of this patent with color drawing(s) will be provided by the Patent and Trademark Office upon request and with payment of the necessary fee.

BRIEF DESCRIPTION OF THE DRAWINGS

FIGS. 1A and 1B. Characterization of Anti-E-Selectin Monoclonal Antibodies. (A) Inhibition of HL60 cell adhesion to cytokine activated HUVECs (solid bars) and E-Selectin transfected COS cells (striped bars) by anti-E-Selectin monoclonal antibodies. Cells were preincubated with MAb's (10 ug/ml) for 1 hr at room temperature and HL60 cell adhesion determined as described in the Experimental Procedures section of Example 1. Each bar represents the mean +/− SD of triplicate determinations expressed as a percent of control binding. (B) Binding of anti-E-Selectin MAb's to human (solid bars) and rabbit (striped bars) E-Selectin. Antibodies (10 μg/ml) were incubated for 1 hr at room temperature on 96 well microtitre plates to which recombinant soluble human or rabbit E-Selectin had been bound. Wells were washed and incubated with horseradish peroxidase coupled goat anti-mouse IgG, washed and developed using standard protocols.

FIGS. 2A and 2B. E-Selectin Constructs. (A) Amino acid alignment of the lectin domains of human (SEQ. ID. NO: 36) and rabbit (SEQ. ID. NO: 37) E-Selectin beginning at the putative N-terminus of the mature polypeptide. Amino acid substitutions in the rabbit peptide are depicted, all other positions are identical with the human residues. (B) E-Selectin constructs used to map Mabs and sLex binding sites. The human E-Selectin contained amino acids 1–157, the rabbit E-Selectin encoded amino acids 1–156 and HuRa-1 contained residues 1–9 of human contiguous with residues 10–156 of rabbit E-Selectin. Each is anchored to the cell surface via a GPI link encoded by CD16 sequences. Also shown is an E-Selectin-IgG chimera (E Sel-IgG) containing the lectin, egf-like and complement binding-like domains (CBD) 1 and 2 of human E-Selectin ligated to the hinge, CH2 and CH3 regions of human IgG 1 [Watson et al., *J. Cell Biol.* 115, 235–243 (1990)].

FIG. 3. Binding of blocking antibodies to HuRa-1 chimera. Immunofluorescence localization of anti-E-Selectin antibody binding to human E-Selectin lec-egf-CD16 (column 1), rabbit E-Selectin lec-egf CD16 (column 2) and HuRa-1, human-rabbit chimeric E-Selectin lectin-egf CD16 (column 3) transfected COS cells. Transfected cells were fixed and stained with anti-E-Selectin Mabs 3B7 (row 1), 7H5 (row 2), 8E4 (row 3) or 14G2 (row 4).

FIG. 4. HL60 binding to HuRa-1 in the presence of blocking antibodies. Inhibition of HL60 binding to human E-Selectin lec-egf-CD16 (solid bars), rabbit E-Selectin lec-egf-CD16 (striped bars), and HuRa-1 human-rabbit chimeric E-Selectin lectin-egf-CD16 (striped bars) transfected COS cells by anti-E-Selectin blocking Mabs. Cells were preincubated with 3B7, 7H5, 8E4, or 14G2 (10 μg/ml) for 1 hr and HL60 cell adhesion determined as described in the Experimental Procedures section of Example 1. Each bar represents the mean +/− SD of triplicate determinations.

FIGS. 5A through 5E. Reactivity of anti-E-Selectin MAbs with Mutant Chimeras. E-Selectin-IgG chimeras with the mutations shown were tested for capture by each of fifteen anti-E-Selectin MAbs using the ELISA format described in the Experimental Procedures section of Example 1. Results shown represent the mean +/− S.D. of duplicate determinations and are expressed as percentage of control or wild type binding.

FIGS. 6A and B. Binding of Alanine Scan Mutants to Immobilized sLex Glycolipid. (A) E-Selectin-IgG chimeras in which the indicated residues were mutated to alanine were tested for binding to immobilized 2,3 sLex glycolipid by the ELISA procedure described in the Experimental Procedures section of Example 1. Results shown represent the mean +/− S.D. of triplicate determinations expressed as percentage of control or wild type binding. (B) E-Selectin-IgG mutant ESA (open squares) or wild type E-Selectin-IgG (closed squares) were tested at the indicated concentrations for binding to immobilized 2,3 sLex glycolipid by ELISA as above. Results shown represent the mean +/− S.D. of triplicate determinations.

Figure 7A:
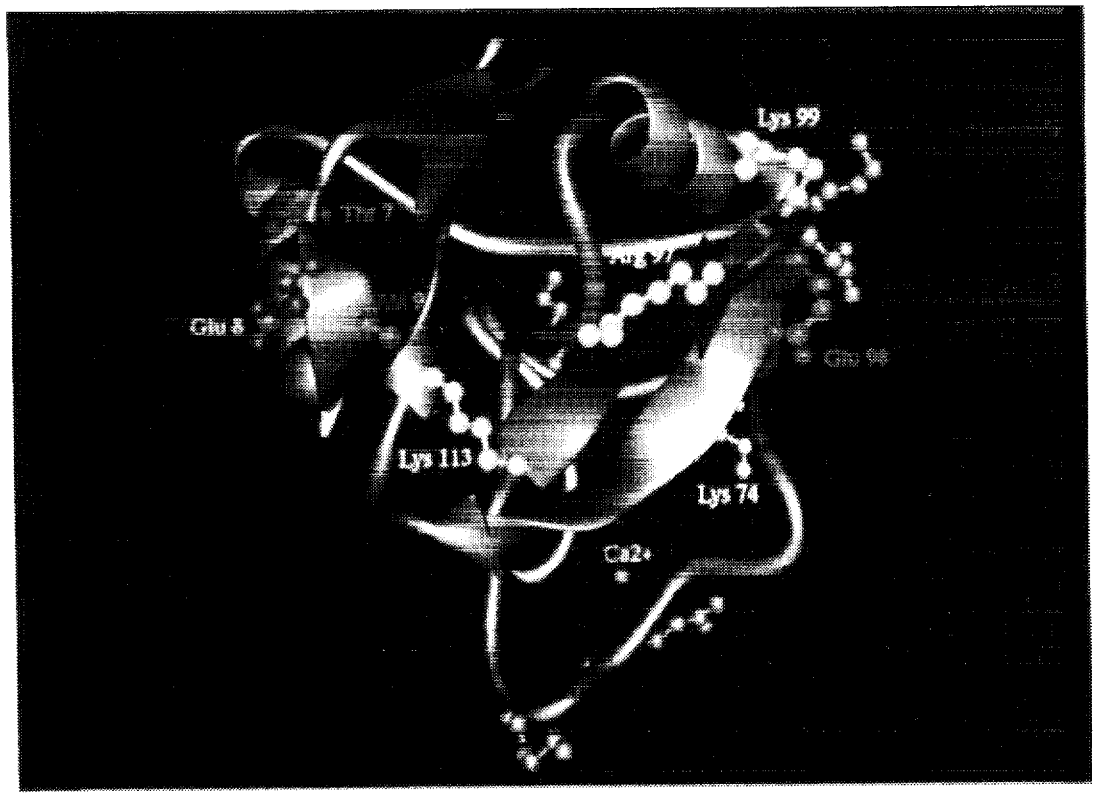

FIGS. 7A and B. A Model of the Lectin Domain of E-Selectin. Shown is a ribbon model of the E-Selectin lectin domain derived from the published coordinates of the related type C lectin, the mannose binding protein [Weis et al., *Science* 254, 1608–1615 (1991)]. Orientation A shows the amino acid residues whose mutation did not affect sLex or Mab binding (brown), the residue at position 74 whose mutation did not affect sLex binding but did affect the binding of a number of non-blocking Mab (pink), the residues at positions 7,9 and 98 whose mutation abolished binding of blocking Mab (red), the residues at positions 97,99 and 113 whose mutation abolished sLex binding (yellow), and the residue at position 8 whose mutation enhanced the affinity of E-Selectin for sLex (green). As noted hereinafter, mutation of residues 8 and 113 also affected the binding of some blocking Mabs. The single bound calcium is depicted as a green ball. Also shown in orientation A is the solution structure of sLex [Tyrrell et al., *Proc. Natl. Acad. Sci. U.S.A.* 88, 10372–10376 (1991); Berg et al., *J. Biol. Chem.* 265, 14869–14872 (1991)]. The dark purple loop (residues S43-Y48) and the dark blue loop (residues Y94-D100) denote two loops near the carbohydrate binding site of E-Selectin that are not found in the mannose binding protein. Orientation B shows the "active site" of carbohydrate binding from a face-on view, with residues involved with carbohydrate recognition and/or blocking Mab binding colored as in orientation A.

Figure 8:
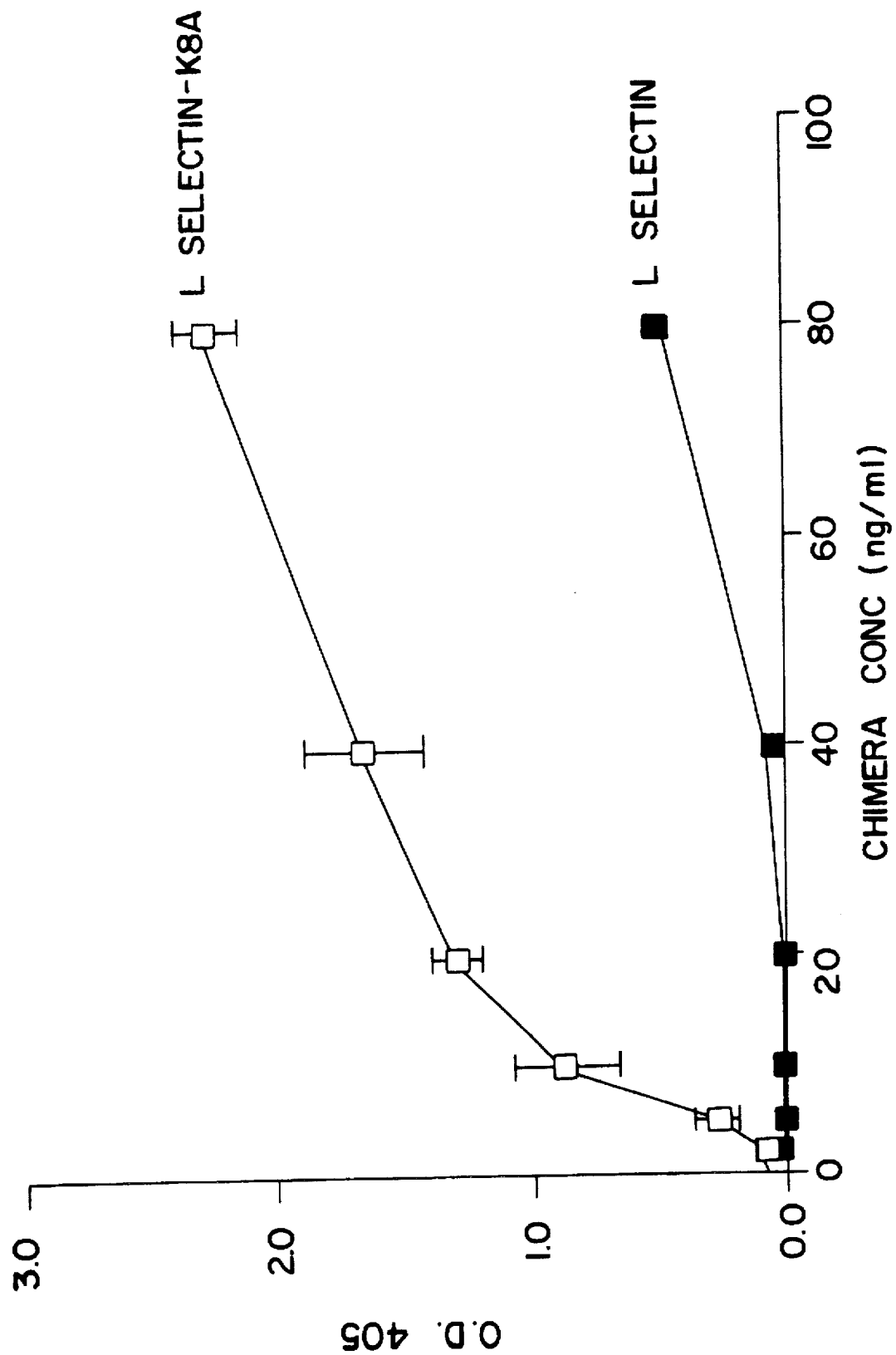

FIG. 8. Binding of L-Selectin-IgG mutant K8A to immobilized sLex. L-Selectin-IgG mutant K8A (open squares) or wild type L-Selectin-IgG (closed squares) was tested at the indicated concentrations for binding to immobilized 2,3 sLex glycolipid by ELISA as above. Results shown represent the mean +/− S.D. of triplicate determinations.

FIG. 9. Structures of the selectin (LEC-CAM) family members as determined by cDNA cloning. Illustrated are the structures for L-Selectin, E-Selectin and P-Selectin. The lectin, epidermal growth factor (EGF), and multiple short consensus repeats (SCRs) are shown with hypothetical disulfide bond structures as first proposed for GMP-140 by Johnston et al., *Cell* 56, 1033 (1989). An N-terminal sequence is also shown (subsequently cleaved in the mature protein) as well as a hydrophobic transmembrane spanning anchor (TM) and cytoplasmic tail. Two other forms of P-Selectin are also illustrated, one with a deleted scr-7 domain and another with a deleted membrane spanning anchor.

FIGS. 10A through 10D. Staining of HL-60 cells and neutrophils by selectin-IgG chimeras. Selectin-IgG chimeras were tested by flow cytometry for staining of either HL60 cells (A and C) or human neutrophils (B and D) as described in Example 3. In (A) and (B), the peaks to the left and far left of the vertical, dashed line represent P-Selectin-IgG staining in the presence of 10 mM EGTA and E-Selectin-IgG staining, respectively. The peak to the right of the dashed line represents P-Selectin-IgG staining. Staining with no chimera (secondary antibody only) was identical to E-Selectin-IgG staining for both cell types. (C) HL60 cells were treated as indicated in Example 3, and stained with P-Selectin-IgG as in (A). Results are expressed as percentage of cells staining positively (+/− SD of duplicates) based on staining with secondary antibody alone. (D) Human neutrophils before (solid bars) or after (striped bars) activation with PMA were stained with the indicated reagents and evaluated by flow cytometry as described in Example 3. Results are shown as the linear mean fluorescence.

Figure 11A:
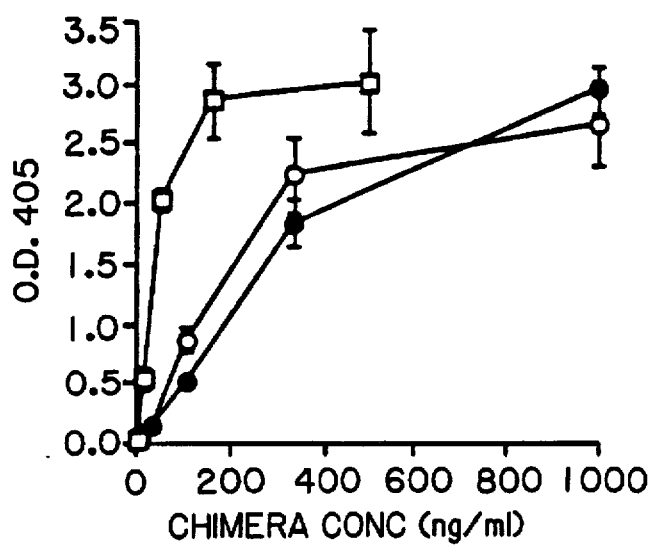
Figure 11B:
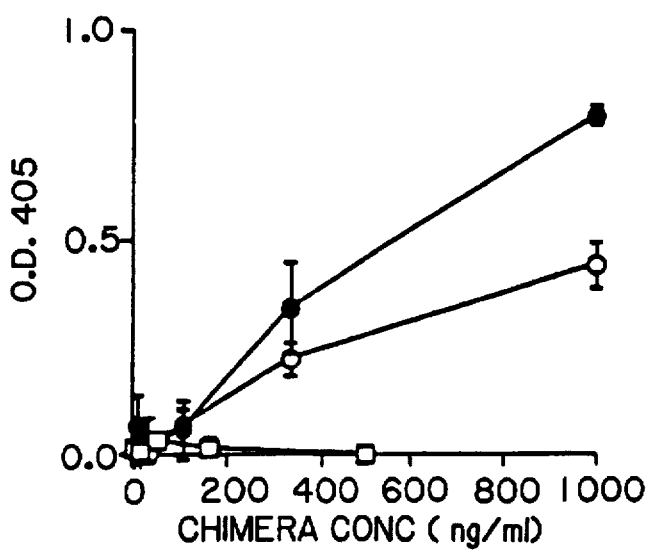
Figure 11C:
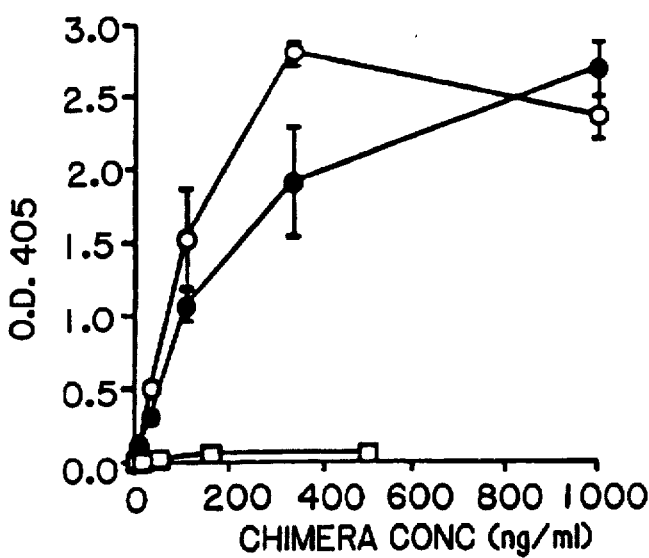

FIGS. 11A–C. Binding of the PE-1 chimera to Immobilized sLex Glycolipids and Sulfatides. P-Selectin-IgG (open circles), E-Selectin-IgG (open squares) or PE-1 (closed circles) were tested at the indicated concentrations for binding to immobilized 2'3 sLex glycolipid (A), 2'6 sLex glycolipid (B), or sulfatides (C) by the ELISA procedure described in Example 3. Results shown represent the mean +/− SD of triplicate determinations.

FIG. 12. Staining of HL60 cells with the PE-1 Chimera. The P-Selectin-IgG, E-Selectin-IgG, and PE-1 chimeras were tested for binding to HL60 cells by flow cytometry as in FIG. 10. The percentage of cells staining positively (based on staining with the secondary antibody alone) with each chimera is indicated.

FIGS. 13A and B. A Model of the Lectin Domain of P-Selectin. Shown is a ribbon model of the P-Selectin lectin domain (panel A) alongside a ribbon model of the E-Selectin lectin domain (panel B). Each model is similarly derived from the published coordinates of the related type C lectin, the mannose binding protein as described in Examples 1 and 3. Residues shown are colored as follows: for P-Selectin (panel A) K8-green, K84-brown, S-97-white, and top-to-bottom Y48-K113-K111-yellow; for E-Selectin (panel B) E8-green, R84-brown, R97-red, top-to-bottom Y48-K113-K111-yellow. The purple loop and the dark blue loop in each model denote two insertions near the proposed carbohydrate binding sites that are not found in the mannose binding protein. In each panel, the bar represents 10 Å.

FIG. 14. Reactivity of anti-P-Selectin mAb's with Mutant Chimeras. P-Selectin-IgG chimeras with the substitutions indicated were tested for capture by the mAb's AK-6 (solid bars), AC 1.2 (open bars), and CRC 81 (hatched bars) as in Table 1. Results shown represent the mean +/− SD of duplicate determinations and are expressed as percentage of control P-Selectin-IgG binding.

FIGS. 15A through 15D. Binding of P-Selectin-IgG Mutants to Immobilized Glycolipids and Cells. P-Selectin-IgG chimeras with the substitutions indicated were tested for binding to immobilized 2'3 sLex glycolipid (A), 2'6 sLex glycolipid (B), or sulfatides (C) as in FIG. 11, and for staining of HL60 cells (D) as in FIG. 10.

FIGS. 16A through 16C. Antibody Capture and 2'3 sLex binding of N82D E-Selectin. N82D E-Selectin was generated and tested as described in Example 1. (A) Antibody capture; (B) binding to 2'3 sLex; (C) binding to 2'3 sLex in the presence of added calcium.

DETAILED DESCRIPTION OF THE INVENTION

I. Definitions

The term "selectin" is used to refer to a cell adhesion molecule having, within its extracellular region, a lectin domain, an egf-like domain and complement binding-like domains and having the qualitative ability to mediate cell binding through interaction with a cell surface carbohydrate ligand, but nonetheless may have fewer or more domains if it still functions as a mediator of cell adhesion. The definition specifically includes "soluble" selectin molecules lacking a functional transmembrane domain as well as amino acid sequence and glycosylation variants and covalent modifications of a native selectin.

The expression "native selectin" is used to define a native sequence selectin molecule of any human or non-human animal species including naturally occurring allelic variations that might occur from individual to individual, demonstrated by (an) amino acid difference(s) in the overall sequence, without any limitation as to its mode of preparation. Thus, the native selectin may be obtained from any native source, may be produced synthetically or by recombinant DNA technology, or by suitable combination of such methods. The term specifically includes native mammalian, e.g. human and E-, L- and P-Selectins.

The expression "corresponding selectin" as used throughout the specification and claims refers to a selectin molecule having an unaltered native selectin lectin domain, that may, however, have alterations in other parts of the molecules in agreement with the foregoing definition for "selectin". Thus, for example, for E-Selectin variants the corresponding selectin has a native sequence (unaltered) E-Selectin lectin domain of any animal species but may otherwise differ from naturally occurring E-Selectins.

In the claims and throughout the specification certain alterations are defined with reference to amino acid residue numbers of the lectin domain of the corresponding native human selectin. The amino acid numbering starts at the first N-terminal amino acid of the lectin domain of a native human E-, L- or P-Selectin amino acid sequence. The amino acid sequence of the Lectin domain of native human E-Selectin is shown in FIG. 2(A) (amino acids 1–120) (SEQ. ID. NO: 36). The lectin domain of native human L-Selectin comprises amino acid residue numbers designated as residues 39–155 in FIG. 1 of U.S. Pat. No. 5,098,833 issued 24 Mar. 1992. Following the sequence numbering applied herein, these residues are referred to as amino acid residue numbers 1–117 and are shown in SEQ. ID. NO: 38. The amino acid sequence of the lectin domain of P-Selectin is, for example, shown in FIG. 2 of Lasky, L. A., *J. Cell. Biochem.* 45, 139–146 (1991) and is shown in SEQ. ID. NO: 39. The latter publication also shows the relative sequence homologies of the lectin domains of the three selectins.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

The terms "amino acid alteration" and "alteration" refer to amino acid substitutions, deletions or insertions or any combinations thereof in a selectin amino acid sequence. In the selectin variants of the present invention such alteration is at a site or sites of a selectin lectin domain amino acid sequence.

Substitutional variants herein are those that have at least one amino acid residue in a native selectin lectin domain sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native selectin lectin domain sequence. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the native selectin lectin domain amino acid sequence removed. Ordinarily, deletional variants will have one or two amino acids deleted in a particular region of the lectin domain amino acid sequence.

The designation of the substitution variants herein consists of a letter followed by a number followed by a latter. The first (leftmost) letter designates the amino acid in the native (unaltered) selectin lectin domain. The number refers to the amino acid position where the amino acid substitution is being made, and the second (righthand) letter designates the amino acid that is used to replace the native amino acid. The designation for an insertion variant consists of the letter "i" followed by a number designating the position of the residue in a native selectin amino acid sequence before which the insertion starts, followed by one or more capital letters indicating, inclusively, the insertion to be made. The designation for a deletion variant consists of the letter "d" followed by the number of the start position of the deletion to the number of the end position of the deletion, with the positions being based on the amino acid sequence of the native sequence, unaltered lectin domain of the corresponding (E, L or P) selectin. As mentioned before, the numbering starts at the N-terminal amino acid sequence of the selectin lectin domain (which is the N-terminal end of the mature native selectin molecule). Multiple alterations are separated by a comma (,) in the notation for ease of reading them.

The terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

Nucleic acid is "operably linked" when it is placed into a functional relationship with another nucleic acid sequence. For example, DNA for a presequence or secretory leader is operably linked to a DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property as screened for in the originally transformed cell are included.

"Transformation" means introducing DNA into an organism so that the DNA is replicable, either as an extrachromosomal element or by chromosomal integration.

"Transfection" refers to the taking up of an expression vector by a host cell whether or not any coding sequences are in fact expressed.

The terms "transformed host cell" and "transformed" refer to the introduction of DNA into a cell. The cell is termed a "host cell", and it may be a prokaryotic or a eukaryotic cell. Typical prokaryotic host cells include various strains of *E. coli*. Typical eukaryotic host cells are mammalian, such as Chinese hamster ovary cells or human embryonic kidney 293 cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published 4 May 1988, or via deoxynucleoside H-phosphanate intermediates as described by Froehler et al., *Nucl. Acids Res.* 14, 5399 (1986)]. They are then purified on polyacrylamide gels.

The technique of "polymerase chain reaction" or "PCR", as used herein, generally refers to a procedure wherein minute amounts of a specific piece of nucleic acid, RNA and/or DNA, are amplified as described in U.S. Pat. No. 4,683,195, issued 28 Jul. 1987 and in *Current Protocols in Molecular Biology*, Ausubel et al. eds., Greene Publishing Associates and Wiley-Interscience 1991, Volume 2, Chapter 15.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. The monoclonal antibodies include hybrid and recombinant antibodies produced by splicing a variable (including hypervariable) domain of an anti-selectin ligand antibody with a constant domain (e.g. "humanized" antibodies), only one of which is directed against a selectin, or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv). Cabilly, et al., U.S. Pat. No. 4,816,567; Mage & Lamoyi, in *Monoclonal Antibody Production Techniques and Applications*, pp.79–97 (Marcel Dekker, Inc., New York, 1987). Thus, the modifier "monoclonal" indicates the character of the antibody as being obtained from such a substantially homogeneous population of antibodies, and is not to be construed as requiring production of the antibody by any particular method.

The expression "blocking monoclonal antibody" is used to refer to monoclonal antibodies capable of inhibiting the binding of a selectin variant of the present invention to a native ligand of the corresponding (E, L or P) selectin in a standard binding assay such as the assay described in Example 1.

The term "immunoglobulin" generally refers to polypeptides comprising a light or heavy chain usually both disulfide bonded in the native "Y" configuration, although other linkage between them, including tetramers or aggregates thereof, is within the scope hereof.

Immunoglobulins (Ig) and certain variants thereof are known and many have been prepared in recombinant cell culture. For example, see U.S. Pat. No. 4,745,055; EP 256,654; Faulkner et al., *Nature* 298:286 (1982); EP 120, 694; EP 125,023; Morrison, *J. Immun.* 123:793 (1979); Köhler et al., *Proc. Nat'l. Acad. Sci. U.S.A.* 77:2197 (1980); Raso et al., *Cancer Res* 41:2073 (1981); Morrison et al., *Ann. Rev. Immunol.* 2:239 (1984); Morrison, *Science* 229:1202 (1985); Morrison et al., *Proc. Nat'l. Acad. Sci. U.S.A.* 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. L-Selectin-immunoglobulin chimeras are, for example, disclosed in WO 91/08298 published 13 Jun. 1991. The production and characterization of E-Selectin-immunoglobulin chimeras has been reported by Foxall et al., *J. Cell. Biol.* 1992, in press. P-Selectin-immunoglobulin chimeras have been constructed in an analogous manner. The immunoglobulin moiety in the chimera of the present invention may be obtained from IgG$_1$, IgG$_2$, IgG$_3$, or IgG$_4$ subtypes, IgA, IgE, IgD or IgM, but preferably IgG$_1$ or IgG$_3$.

II. Construction of the Selectin Variants and their Derivatives

Site Directed Mutagenesis

Preparation of selectin variants in accordance herewith is preferably achieved by site-specific mutagenesis of DNA that encodes an earlier prepared variant or a nonvariant version of the protein. Site-specific mutagenesis allows the production of selectin variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., *DNA*, 2: 183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.*, 153: 3 (1987)) may be employed to obtain single-stranded DNA.

The specific mutagenesis method followed in making the E-Selectin variants of Example 1 was described by Kunkel et al., *Methods in Enzymol.* 154 367–382 (1987).

In general, site-directed mutagenesis may, for example, be performed by first obtaining a single-stranded vector that includes within its sequence a DNA sequence that encodes the relevant selectin. An oligonucleotide primer bearing the desired mutated sequence is prepared, generally synthetically, for example, by the method of Crea et al., *Proc. Natl. Acad. Sci.* (U.S.A.), 75: 5765 (1978). This primer is then annealed with the single-stranded selectin sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected, via hybridization to a radioactive probe consisting of the $^{32}$P-labeled mutagenesis primer, that include recombinant vectors bearing the mutated sequence arrangement.

After such a clone is selected, the mutated selectin region may be removed and placed in an appropriate vector for selectin production, generally an expression vector of the type that typically is employed for transformation of an appropriate eukaryotic host. In the context of the present invention, Chinese hamster ovary (CHO) cells or 293 (human kidney cells described by Graham et al., *J. Gen. Virol.*, 36:59 (1977)) are preferred for the preparation of long-term stable selectin producers. However, the invention is not limited to CHO production, as it is known that numerous other cell types are suitably employed, particularly where one desires only transient production of the enzyme for test purposes. For example, described below is a transient system employing 293 cells that provides a convenient system for production of selectin variants for analytical purposes.

Another method for making mutations in the DNA sequence encoding a selectin involves cleaving the DNA at the appropriate position by digestion with restriction enzymes, recovering the properly cleaved DNA, synthesizing an oligonucleotide encoding the desired amino acid and flanking regions such as polylinkers with blunt ends (or, instead of using polylinkers, digesting the synthetic oligonucleotide with the restriction enzymes also used to cleave the selectin-encoding DNA, thereby creating cohesive termini), and ligating the synthetic DNA into the remainder of the selectin-encoding structural gene.

PCR Mutagenesis

PCR mutagenesis is also suitable for making the selectin amino acid variants of the present invention. While the following discussion refers to DNA, it is understood that the technique also find application with RNA. The PCR technique generally refers to the following procedure. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more)-part ligation.

Host Cell Cultures and Vectors

Although expression on Chinese hamster ovary (CHO) cells and in the human embryonic kidney cell line 293 [Urlaub and Chasin, *Proc. Natl. Acad. Sci. U.S.A.* 77, 4216 (1980); Graham et al., *J. Gen. Virol.*, 36, 59 (1977)] are ultimately preferred for the production of the selectin variants herein, the vectors and methods disclosed herein are suitable for use in host cells over a wide range of eukaryotic organisms.

In general, of course, prokaryotes are preferred for the initial cloning of DNA sequences and constructing the vectors useful in the invention. For example, *E. coli* K12 strain 294 (ATCC No. 31,446) and *E. coli* strain W3110 (ATCC No. 27,325) are particularly useful. Other suitable microbial strains include *E. coli* strains such as *E. coli* B, and *E. coli* X1776 (ATCC No. 31,537). These examples are, of course, intended to be illustrative rather than limiting.

Prokaryotes also are useful for expression. The aforementioned strains, as well as bacilli such as *Bacillus subtills*, and other enterobacteriaceae such as, e.g., *Salmonella typhimurium* or *Serratia marcesans*, and various Pseudomonas species are examples of useful hosts for expression.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include β-lactamase (penicillinase) and lactose promoter systems (Chang et al., *Nature*, 375: 615 (1978); Itakura et al., *Science*, 198: 1056 (1977); Goeddel et al., *Nature*, 281: 544 (1979)) and a tryptophan (trp) promoter system (Goeddel et al., *Nucl. Acids Res.*, 8: 4057 (1980); EPO Appl. Publ. No. 36,776), and the alkaline phosphatase systems. While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell*, 20:269 (1980)).

In addition to prokaryotes, eukaryotic microbes, such as yeasts, also are suitably used herein. *Saccharomyces cerevisiae*, or common baker's yeast, is the most commonly used among eukaryotic microorganisms, although a number of other strains are commonly available. For example, for expression in Saccharomyces, the plasmid YRp7 (Stinchcomb et al., *Nature*, 282: 39 (1979); Kingsman et al., *Gene*, 2: 141 (1979); Tschemper et al., *Gene*, 10: 157 (1980)) is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85:12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland et al., *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, CHO cell lines, and W138, BHK, COS-7, (ATCC CRL 1651), 293, and MDCK (ATCC CCL 34) cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., *Nature*, 273: 113 (1978)). Smaller or larger SV40 fragments are also suitably used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication typically is provided either by construction of the vector to include an exogenous origin, such as may be derived from SV40 or other viral (e.g., Polyoma, Adeno, VSV, BPV) source, or by the host cell chromosomal replication mechanism. If the vector is integrated into the host cell chromosome, the latter is often sufficient.

Satisfactory amounts of human selectin variants are produced by cell cultures; however, refinements, using a secondary coding sequence, serve to enhance production levels even further. The secondary coding sequence comprises dihydrofolate reductase (DHFR) that is affected by an externally controlled parameter, such as methotrexate (MTX), thus permitting control of expression by control of the MTX concentration.

In the selection of a preferred host cell for transfection by the vectors of the invention that comprise DNA sequences encoding both variant selectin and DHFR protein, it is appropriate to consider the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated, as described by Urlaub and Chasin, *Proc. Natl. Acad. Sci.* (U.S.A.) 77: 4216 (1980).

On the other hand, if DHFR protein with low binding affinity for MTX is used as the controlling sequence, it is not necessary to use DHFR-deficient cells. Because the mutant DHFR is resistant to MTX, MTX-containing media can be used as a means of selection, provided that the host cells are themselves MTX sensitive. Most eukaryotic cells that are capable of absorbing MTX appear to be sensitive to MTX. One such useful cell line is a CHO line, CHO-K1 (ATCC No. CCL 61).

Typical Cloning and Expression Methodologies Available

If mammalian cells are used as host cells, transfection generally is carried out by the calcium phosphate precipitation method as described by Graham and Van der Eb, *Virology*, 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.*, 75: 1929–1933 (1978).

If prokaryotic cells or cells that contain substantial cell wall constructions are used, the preferred method of transfection is calcium treatment using calcium as described by Cohen et al., *Proc. Natl. Acad. Sci. (U.S.A.)* 69: 2110 (1972), or more recently electroporation.

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 µg plasmid or DNA fragments is used with about 1 unit of enzyme in about 20 µl of buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C with 10 units of the Klenow fragment of DNA Polymerase I (Klenow), phenol-chloroform extracted, and ethanol precipitated.

Size separation of the cleaved fragments is performed using 6 percent polyacrylamide gel described by Goeddel et al., *Nucleic Acids Res.*, 8: 4057 (1980).

For ligation, approximately equimolar amounts of the desired components, suitably end tailored to provide correct matching, are treated with about 10 units T4 DNA ligase per 0.5 µg DNA. (When cleaved vectors are used as components, it may be useful to prevent religation of the cleaved vector by pretreatment with bacterial alkaline phosphatase.)

As discussed above, selectin variants are preferably produced by means of specific mutation. Variants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation being traversed.

For analysis to confirm correct sequences in plasmids constructed, the ligation mixtures are typically used to transform *E. coli* K12 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids. Res.*, 9: 309 (1981) or by the method of Maxam et al., *Methods of Enzymology*, 65: 499 (1980).

After introduction of the DNA into the mammalian cell host and selection in medium for stable transformants, amplification of DHFR-protein-coding sequences is effected by growing host cell cultures in the presence of approximately 20,000–500,000 nM concentrations of MTX, a competitive inhibitor of DHFR activity. The effective range of concentration is highly dependent, of course, upon the nature of the DHFR gene and protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Glycosylation Variants

Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. O-linked glycoslation sites may, for example, be modified by the addition of, or substitution by, one or more serine or threonine residue to the amino acid sequence of the ligand. For ease, changes are usually made at the DNA level, essentially using the techniques discussed hereinabove with respect to the amino acid sequence variants.

Chemical or enzymatic coupling of glycosydes to the selectin variants of the present invention may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxdryl groups, (e) aromatic residues such as those of phenylalanine, tyrosine, or tryptophan or (f) the amide group of glutamine. These methods are described in WO 87/05330 (published 11 Sep. 1987), and in Aplin and Wriston, *CRC Crit. Rev. Biochem.*, pp. 259–306 (1981).

Carbohydrate moieties present on a selectin variant may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., *Arch. Biochem, Biophys.* 259, 52 (1987) and by Edge et al., *Anal. Biochem.* 118, 131 (1981). Carbohydrate moieties can be removed by a variety of endo- and exoglycosidases as described by Thotakura et al., *Meth. Enzymol.* 138, 350 (1987). Glycosylation is suppressed by tunicamycin as described by Duskin et al., *J. Biol. Chem.* 257, 3105 (1982). Tunicamycin blocks the formation of protein-N-glycosydase linkages.

Glycosylation variants of the variants herein can also be produced by selecting appropriate host cells. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the selectin variant, are routinely screened for the ability to introduce variant glycosylation.

Covalent Modifications

Covalent modifications of a selectin variant molecule are included within the scope herein. Such modifications are traditionally introduced by reacting targeted amino acid residues of the selectin variant with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays of the selectin ligands, or for the preparation of anti-selectin ligand antibodies for immunoaffinity purification of the recombinant glycoprotein. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intramolecular aggregates of the selectin variants as well as for cross-linking the selectin variants to a water insoluble support matrix or surface for use in assays or affinity purification. In addition, a study of interchain cross-links will provide direct information on conformational structure. Commonly used cross-linking agents include 1,1-bis (diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel selectin variants of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The selectin variants may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The selectin variants may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

Construction of Selectin Variant-Immunoglobulin Chimeras

A selectin variant sequence can be linked to a immunoglobulin constant domain sequence as hereinbefore defined. The resultant molecules are commonly referred to as selectin immunoglobulin chimeras. Such chimeras can be constructed essentially as described in WO 91/08298 (published 13 Jun. 1991).

Ordinarily, the selectin variant is fused C-terminally to the N-terminus of the constant region of an immunoglobulin in place of the variable region(s), however N-terminal fusions of the selectin variants are also desirable. The transmembrane regions of the selectin variants are preferably inactivated or deleted prior to fusion.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, however, the selectin variant-immunoglobulin chimeras of this invention may be synthesized according to known methods.

The precise site at which the fusion is made is not critical; particular sites are well known and may be selected in order to optimize the biological activity, secretion or binding characteristics of the selectin variant.

In some embodiments, the hybrid immunoglobulins are assembled as monomers, or hetero- or homo-multimers, and particularly as dimers of tetramers, essentially as illustrated in WO 91/08298, Supra.

In a preferred embodiment, the C-terminus of a sequence which contains the binding site(s) for a selectin ligand, is fused to the N-terminus of the C-terminal portion of an antibody (in particular the Fc domain), containing the effector functions of an immunoglobulin, e.g. immunoglobulin $G_1$. It is possible to fuse the entire heavy chain constant region to the sequence containing the ligand binding site(s). However, more preferably, a sequence beginning in the hinge region just upstream of the papain cleavage site (which defines IgG Fc chemically; residue 216, taking the first residue of heavy chain constant region to be 114 [Kobet et al., Supra], or analogous sites of other immunoglobulins) is used in the fusion. In a particularly preferred embodiment, the amino acid sequence containing the ligand binding site(s) (preferably retaining the egf like and complement binding domains) is fused to the hinge region and $C_H2$ and $C_H3$ or $C_H1$, hinge, $C_H2$ and $C_H3$ domains of an $IgG_1$, $IgG_2$ or $IgG_3$ heavy chain. The precise site at which the fusion is made is not critical, and the optimal site can be determined by routine experimentation.

III. Preferred Selectin Variants

Ordinarily, the selectin variants of the present invention will have a lectin domain the amino acid sequence of which is substantially homologous (ordinarily more than about 80% based on complete amino acid identity, ignoring insertions or deletions) to that of a native selectin molecule, but containing one or more amino acid residue substitutions, deletions or insertions at one or more of certain specified sites within this domain. The variant selectin molecules of the present invention may exhibit altered (preferably enhanced) affinity for binding to a corresponding native selectin ligand as a result of the alteration(s) in their lectin domains. The inventive amino acid sequence variants of the present invention are one or combination of substitutional, insertional, or deletional variants at certain sites which have been identified by the inventors to be important or influential in modulating the ligand binding properties of selectins.

The amino acid residues identified as primarily involved with recognition of the carbohydrate ligands of selectins are a relatively small patch on the surface of the selectin lectin domain near the antiparallel beta sheet formed by the disulfide-linked N- and C-termini and the adjacent disulfide linked loop formed by the two internal cysteines. Based upon experimental evidence disclosed in the Examples, it is believed especially that positively charged amino acid residues in this region are critical for carbohydrate recognition. Accordingly, alterations in this region, and especially at positively charged amino acids are expected to have the greatest influence on the ligand binding properties of the selectin molecule.

In general, substantial changes in the ligand binding properties of the selectin molecule may be obtained by substituting amino acids within the above-identified region which have significantly different side chains than the native residue at that site. Such substitutions would be expected to affect (a) the structure of the polypeptide backbone in the area of substitution, for example as a sheet or helical conformation, (b) the charge or hydrophobicity of the molecule at the target site, or (c) the bulk of the side chain. The substitutions which would be expected to cause the greatest changes in the chemical and/or physical properties of the selectin molecule are those in which (a) a basic (positively charged) residue is substituted with an aliphatic or aromatic residue, (b) an acidic residue is substituted with an aliphatic or aromatic residue, (c) a hydrophilic residue is substituted with an aromatic or aliphatic residue, (d) an aromatic residue is substituted with an acidic or basic residue, (e) an aliphatic residue is substituted with an acidic or basic residue, or (f) a non-polar residue is substituted with an acidic or basic residue.

Figure 7B:

In particular, three positively charged amino acid residues that proved to be critical for sLex recognition by E-Selectin, arginine (R) at residue number 97, lysine (K) at residue number 111, and lysine (K) at residue number 113, are situated very close to each other on the E-Selectin model shown in FIG. 7. Lysine at amino acid positions 111 and 113 is conserved in all three selectins from a number of different species. Accordingly, the presence of a positively charged residue, e.g., lysine, at this position is believed to be essential for ligand binding. The replacement of this amino acid residue with an uncharged amino acid (alanine) completely abolished sLex recognition. The replacement of arginine at position 97 of the selectin lectin domain is conserved in E- and L-Selectin only, whereas P-Selectin has serine (a hydrophilic uncharged amino acid) at this site. In E-Selectin, the substitution of alanine for this residue abolished sLex binding, hence, this residue is also critical for carbohydrate recognition.

An entirely unexpected finding was the increase in ligand binding affinity observed as a result of the substitution of alanine for glutamic acid (a charged residue) at position 8 of the E-Selectin amino acid sequence. L- and P-Selectin contain a positive charge (K) at this site, the mutation of which to alanine in L-Selectin was found to significantly enhance sLex recognition (Example 2).

Accordingly, substantial changes in the ligand binding properties of a selectin molecule can be expected from alterations within the above-identified patch in the selectin lectin domain, and in particular, from replacing charged amino acid residues by uncharged residues at the above-described positions. In addition to the charge, the bulk of the amino acid is an important consideration.

Exemplary variant selectin molecules constructed as single-site substitutional variants of selectins are listed in Table 1 below.

TABLE 1

| Modulating Site Subst. | Preferred Subst. | Alternative |
|---|---|---|
| E8 (K8*) | A | V, S, T |
| R97** | K, H | S, T, N, Q, E, D |
| K111 | R, H | S, T, N, G, E, D |
| K113 | R, H | S, T, N, G, E, D |

*for L- and P-Selection
**for E- and L-Selection

In addition to the single-site substitutional variant selectin molecules listed in Table 1, the preferred multiple-site substitutional variant molecules include those having any of the foregoing amino acids substituted at position 8 of the selectin lectin domain, combined with one or more of the foregoing alterations at positions 97, 111 and 113.

Similar substitutions are possible in the amino acid regions 7–9, 43–48, 82–86, and 90–109, and specifically at positions 7, 8, 9, 47, 48, 82, 84, 86, 94, 96, 98 and 100, alone or in any combination.

The variants herein preferably retain the egf-like domains and the complement binding domains of native selectins, but may comprise additional alterations (e.g., conservative amino acid substitutions) at other parts of the molecule without significantly affecting the ligand binding properties of the resultant variants. Additional alterations are also possible at regions of the lectin domain identified as not being involved in ligand binding. The information disclosed herein about the ligand binding sites of selectins can be further refined by further mutagenesis studies, such as by homolog-scanning and by high resolution alanine-scanning mutagenesis [Cunningham, B. C. et al., Science 243: 1330–1336 (1989); Cunningham, B. C. and Wells, J. A., Science 244: 1081–1085 (1989); for review see Wells, J. A., Methods Enzymol. 202: 390–411 (1991)], and ultimately by determining the crystal structures of native selectins.

IV. Therapeutic Compositions

The selectin variants with enhanced ligand binding affinity can be used to block the binding of a corresponding selectin receptor to its native ligand. For example, an L-Selectin variant with enhanced ligand binding properties effectively blocks the binding of an L-Selectin receptor on a circulating leukocyte to its native ligand on an endothelial cell. This property is useful for treating a symptom or condition associated with excessive binding of circulating leukocytes to endothelial cells, such as inflammation associated with rheumatoid arthritis, psoriasis, multiple sclerosis, etc.

The selectin variants of the present invention can be formulated according to known methods to prepare pharmaceutically useful compositions, whereby the ligand is combined in admixture with a pharmaceutically acceptable carrier. Suitable carriers and their formulations are described in *Remington's Pharmaceutical Sciences*, 16th ed., 1980, Mack Publishing Co., edited by Oslo et al., specifically incorporated by reference. These compositions will typically contain an effective amount of the selectin variant, for example, from on the order of about 0.5 to about 10 mg/ml, together with a suitable amount of carrier to prepare pharmaceutically acceptable compositions suitable for effective administration to the patient. The variants may be administered parenterally or by other methods that ensure its delivery to the bloodstream in an effective form.

Compositions particularly well suited for the clinical administration of the selectin variants used to practice this invention include sterile aqueous solutions or sterile hydratable powders such as lyophilized protein. Typically, an appropriate amount of a pharmaceutically acceptable salt is also used in the formulation to render the formulation isotonic.

Dosages and desired drug concentrations of pharmaceutical compositions of this invention may vary depending on the particular use envisioned.

Further details of the invention are illustrated in the following non-limiting Examples.

V. Examples

EXAMPLE 1

A. Experimental Procedures
Production and Characterization of anti-E Selectin Monoclonal Antibodies Monoclonal antibodies to both human and rabbit E-Selectin were generated by immunization of mice with COS cells transiently expressing E-Selectin. COS cells ($5 \times 10^7$/ 0.8 ml in Dulbecco's phosphate buffered saline (DPBS) were transfected by electroporation (350 V, 250 µF, Bio-Rad Gene Pulser) with 20 µg human or rabbit E-Selectin cDNA, incubated on ice for 10 min., resuspended in Dulbecco's modified Eagle's medium (DMEM)/10% fetal bovine serum (FBS) and plated at $10^7$ cells/225 cm$^2$ tissue culture flask. Transfected cells were harvested non-enzymatically at 48–72 hrs., washed twice and resuspended in DPBS. Mice were routinely immunized i.p. with $1 \times 10^7$ cells and boosted every 2–3 weeks. Hybridomas were produced by fusion of immunized mouse splenocytes with SP2/0 cells using standard techniques [Galfre et al. *Nature* 266, 550–552 (1977)]. Hybridoma supernatants were screened by a differential binding enzyme-linked immunoassay (ELISA) to Immulon 2 microtitre plates (Dynatech Laboratories, Inc., Chantilly, Va.) coated with detergent extracts of membranes from E-Selectin transfected and control/non-transfected COS cells. Crude membrane fractions were extracted in 2% Triton X-100, 150 mM NaCl, 50 mM Tris pH 7.5 ($2.5 \times 10^9$ cell equivalents/ml). Extracts were diluted in 50 mM Na$_2$CO$_3$ pH 9.6 and directly coated onto assay plates. Anti-human antibodies were also screened by ELISA assay for selective binding to human umbilical vein endothelial cells (HUVECs) treated for 4 hrs with rhIL-1a (550 pg/ml) and rhTNF (400 U/ml) compared to untreated HUVECs. The specificity of these mAb's were confirmed with cytokine treated HUVECs, and transiently transfected COS cells by immunoblotting, immunoprecipitation, and indirect immunofluorescence (Wolitzky et al in preparation).

Mab 7H5 (IgG3), 8E4 (IgG2A), 3B7 (IgG1), 1D6 (IgG1), 4D9 (IgG3), 1E5 (IgG1), 9A1 (IgG1), 7E10 (IgG1), and 1B3 (IgM) were generated to human E-Selectin, while MAb's 14G2 (IgG1), 11G5 (IgM), and 9H9 (IgM) were produced to rabbit-E-Selectin. Ascites was produced by standard techniques [Hoogenraad and Wraight, *Methods Enzymol.* 121 375–381, (1986)] and antibodies were purified by the caprylic acid precipitation method as described [Reik et al., *J. Immunol. Methods* 100, 123 (1987)]. Mabs BBA 1 and BBA 2 were purchased from British Biotechnology (Oxford, England) while Mab ENA-1 was purchased from San Bio (Uden, the Netherlands)

Adhesion Assays

Confluent cultures of HUVECs plated onto gelatin-coated 96 well tissue culture plates (Costar Corp., Cambridge, Mass.) were treated for 4 hrs. with rhIL-1a (550 pg/ml) and rhTNF (400 U/ml). Wells were washed three times with DPBS and incubated for 1 hr. at 37° C. in DPBS containing 1% BSA and 10 ug/ml of designated MAb. HL60 cells were washed twice and resuspended in RPMI Medium 1640 (GIBCO Laboratories Grand Island, N.Y.) at $5 \times 10^6$ cells/ml and labeled for 30 min. at 37° C. with 40 ug/ml 6 Carboxyfluorescein (6-CFDA). 6-CFDA loaded HL60 cells (100, 000/well) were added and incubated for 20 min. at 25° C. Wells were filled with RPMI and plates were sealed, inverted and spun for 6 min. at 500×G. Non-adherent cells were removed by aspiration and plates read in a CytoFluor 2300 fluorescent plate reader (Millipore Corp., Bedford, Mass.).

COS cells were plated at $5 \times 10^5$ cells/35 mm-diameter well 18 hr prior to transfection. Cells were washed with DPBS and 2 µg DNA was added in 1 ml DMEM containing 10% Nutridoma (Boehringer-Mannheim, Indianapolis), 50 µM chloroquine, and 500 ng/ml DEAE dextran. After incubation for 2.5 hr at 37° C., the wells were aspirated and the cells were incubated in Iscove's modified Dulbecco's medium (IMDM) containing 10% FBS and 10% DMSO for 2.5 min. Wells were aspirated and cells grown in IMDM containing 10%FBS at 37° C. for 48–72 hrs. For adhesion assays, $5 \times 10^6$ 6-CFDA loaded HL60 cells were added to each 35mm diameter well and incubated for 30 min. at 25° C. Wells were washed 3 times with RPMI and the fluorescence associated with adherent cells determined in the CytoFluor 2300 plate reader.

Indirect Immunofluorescence

Transiently transfected COS cells were fixed in DPBS containing 1% (wt/vol) formaldehyde for 15 min at 25° C. Following two washes with DPBS, the cells were blocked with DPBS containing 10% horse serum (DPBS/10%HS) for 30 minutes at room temperature. Cells were incubated for 30 min with 5 ug/ml mAb's 387, 8E4, 7H5, or 14G2 in DPBS/10%HS and then washed three times with DPBS. Following a 30 min incubation with rhodamine-conjugated goat anti-mouse IgG, cells were washed with DPBS, and fluorescence observed on a Zeiss Axioskop microscope.

Human-Rabbit Chimeric E-Selectin Constructs

Expression of truncated forms of human and rabbit E-Selectin on the surface of COS cells was achieved by fusing the selectin sequences with the carboxy terminal 37 amino acids of CD16 which contains the signal sequence for cell surface anchorage via a glycosyl-phosphatidylinositol linkage (GPI) [Scallon et al., *Proc. Natl. Acad. Sci. U.S.A.* 86, 5079–5083 (1989)]. All E-Selectin fragments were generated by polymerase chain reaction (PCR) and cloned into the plasmid vector pBC12BI [Cullen, B. R. *Methods in Enzymology* (eds. Berger, S. L., and A. R. Kimmel) 152, 684–704 (1987)] that had been modified to contain the CD16 sequences. Recombinant genes were expressed using the initiating Met codon from the rat preproinsulin gene in pBC12BI and the primary translation product contains five amino acids derived from the insulin signal sequence. The human lectin-egf construct contained amino acids −15 through +157

[Bevilacqua et al., Science 243, 1160–1165 (1989)], the rabbit lectin-egf contained residues −17 through +156 [Larigan et al., J. of DNA and Cell Biology 11, 149–162 (1992)], while the HuRa-1 contained amino acids −15 to +9 of human E-Selectin contiguous with residues 10 through 156 of rabbit E-Selectin. The CD16 sequences required for GPI anchorage to the cell surface were fused to the carboxy termini of each construct.

Construction and Expression of E-Selectin-IgG Chimera Mutants

Production and characterization of the E-Selectin-IgG chimera has been previously described (Foxall et al., 1992, Supra). Mutations were introduced into the lectin domain of this chimera by the method of Kunkel [Kunkel et al., *Methods in Enzymol.* 154, 367–382 (1987)] using the Muta-Gene Phagemid in vitro Mutagenesis Kit (BioRad) according to the manufacturer's instructions. Correct mutants were confirmed by DNA sequencing and the mutant chimeras were transiently expressed and secreted by transfection of 293 cells [Watson et al., *Nature* 349, 164–167 (1991)]. The concentration of each chimera in the resultant supernatants were then quantified by ELISA using an anti-human IgG1-Fc specific mouse mAb as previously described [Watson et al., *J. Cell Biol.* 110, 221–2229 (1990)]. Point mutation sites are defined using the nomenclature of Cunningham and Wells (1989): wild type residue-position-mutant residue.

Oligonucleotide sequences used for mutagenesis:

| NAME | SEQUENCE (5'— —>3') | SEQ. ID. No. |
|---|---|---|
| E Selectin-E8A | 5'-ATA AGT CAT AGC GGC CGT GGA GGT GTT-3' | 1 |
| E Selectin-M10A | 5'-CTC ATT ATA AGT GGC AGC TTC CGT GGA-3' | 3 |
| E Selectin Y12A | 5'-ACT GGC CTC ATT GGC AGT CAT AGC TTC-3' | 2 |
| E Selectin E14A | 5'-ATA AGC ACT GGC TGC ATT ATA AGT CAT-3' | 4 |
| E Selectin K32A | 5'-CTC AAT CTC TTC TGC GTT TTG AAT TGC-3' | 5 |
| E Selectin-S43A | 5'-ACT TGG TGA ATA GGC CAA TAT GGA GTT'3' | 6 |
| E Selectin-Y44A | 5'-ATA ACT TGG TGA AGC GCT CAA TAT GGA-3' | 7 |
| E Selectin-S45A | 5'-GTA ATA ACT TGG TGC ATA GCT CAA TAT-3' | 8 |
| E Selectin-P46A | 5'-CCA GTA ATA ACT TGC TGA ATA GCT CAA-3' | 9 |
| E Selectin-S47A | 5'-AAT CCA GTA ATA AGC TGG TGA ATA GCT-3' | 10 |
| E Selectin-Y48A | 5'-TCC AAT CCA GTA AGC ACT TGG TGA ATA-3' | 11 |
| E Selectin-Y49A | 5'-GAT TCC AAT CCA GGC ATA ACT TGG TGA-3' | 12 |
| E Selectin-K67A | 5'-TTC TTC TGT CAG AGG CGC CTG GGT TCC TAC CCA-3' | 13 |
| E Selectin-K74A | 5'-GGG TTC ACC TGG CGC CCA GTT CGC GGC TTC TTC TGT-3' | 14 |
| E Selectin-R84A,K86A | 5'-CAC GCA GTC CTC ATC TGC TTG CGC ATT GTT GGG TTC ACC-3' | 15 |
| E Selectin-E92A | 5'-CTT GAT GTA GAT GGC CAC GCA GTC CTC-3' | 16 |
| E Selectin-I93A | 5'-TCT CTT GAT GTA GGC CTC CAC GCA GTC-3' | 17 |
| E Selectin-Y94A | 5'-TTC TCT CTT GAT GGC GAT CTC CAC GCA-3' | 18 |
| E Selectin-I95A | 5'-TTT TTC TCT CTT GGC GTA GAT CTC CAC-3' | 19 |
| E Selectin-K96A | 5'-ATC TTT TTC TCT CGC GAT GTA GAT CTC-3' | 20 |
| E Selectin-R97A | 5'-CAC ATC TTT TTC AGC CTT GAT GTA GAT-3' | 21 |
| E Selectin-E98A | 5'-GCC CAC ATC TTT GGC TCT CTT GAT GTA-3' | 22 |
| E Selectin-K99A | 5'-CAT GCC CAC ATC GGC TTC TCT CTT GAT-3' | 23 |
| E Selectin-D100A | 5'-CCA CAT GCC CAC GGC TTT TTC TCT CTT-3' | 24 |
| E Selectin-V101A | 5'-ATT CCA CAT GCC AGC ATC TTT TTC TCT-3' | 25 |
| E Selectin-M103A | 5'-CTC ATC ATT CCA TGC GCC CAC ATC TTT-3' | 26 |
| E Selectin-E107A | 5'-CTT GCT GCA CCT CGC ATC ATT CCA CAT-3' | 27 |
| E Selectin-K111A | 5'-GGC AAG CTT CTT GGC GCT GCA CCT CTC-3' | 28 |
| E Selectin-K113A | 5'-GCA TAG GGC AAG AGC CTT CTT GCT GCA-3' | 29 |
| E Selectin- | 5'-AGC TTC CGT GGA GTA GTG GTA AGT | 30 |

Oligonucleotide sequences used for mutagenesis:

| NAME | SEQUENCE (5'— —>3') | SEQ. ID. No. |
| --- | --- | --- |
| S2H,N4H,T5Y | CCA GGC TCC ACT-3' | |
| E Selectin-T7A,A9N | 5'-ATT ATA AGT CAT ATT TTC CGC GGA GGT GTT GTA-3' | 31 |
| E Selectin-M10Y, T11S,Y12W | 5'-ACT GGC CTC ATT CCA ACT GTA AGC TTC CGT GGA-3' | 32 |
| E Selectin-E98P,V101T | 5'-ATT CCA CAT GCC CGT ATC TTT TGG TCT CTT GAT GTA-3' | 33 |
| L Selectin-K8A | 5'-CCA GTT CAT GGG GGC TTC AGA ATA ATG-3' | 34 |
| P Selectin-K8A | 5'-CCA TGA GTA TGC AGC TGT GCT GTA ATG-3' | 35 |

Monoclonal Antibody Binding of E-Selectin-IgG Mutants

Reactivity of the mutant E-Selectin-IgG chimeras with the various antibodies was determined using a previously described ELISA format [Watson et al., 1990, supra] in which the purified Mab were coated onto microtitre wells, then blocked with BSA. 293 cell supernatants containing equal concentrations of wild type or mutant chimeras were incubated in the wells, followed by washing and detection of the captured chimeras with HRP-conjugated goat polyclonal anti-human Fc antibody.

Sialyl Lewis X Binding of E-Selectin-IgG Mutants

Assays for binding of the mutant E-Selectin-IgG chimeras to immobilized sLex glycolipids were performed essentially as described (Foxall et al., 1992, Supra). Briefly, sLex glycolipids were dried onto microtitre wells, washed with distilled water, and then blocked with BSA. Biotinylated goat F(ab') anti-human IgG Fc and alkaline phosphatase-streptavidin (Caltag, South San Francisco, Calif.) were each diluted 1:1000 into 293 cell supernatants containing equal concentrations of wild type or mutant chimeras and allowed to form a complex prior to addition to the wells. These supernatants were then incubated on the sLex glycolipid coated surfaces, followed by washing, addition of substrate (p-nitrophenyl phosphate), and measurement of the O.D. at 405 nm.

Generation of a Model of the E-Selectin Lectin Domain

The model of E-Selectin was generated based on the crystal structure of the rat mannose-binding protein (MBP) [Weis et al., 1991, Supra]. The sequence of E-Selectin was aligned with those of mouse L-Selectin (LHR) [Lasky et al., Cell 56, 1045–1055 (1989)] and MBP using the alignment of the latter two proteins provided [Weis et al., 1991, Supra). Eleven insertions and two deletions in E-Selectin relative to MBP mapped to four surface loops in the MBP structure. MBP (molecule 1) was transformed into E-Selectin in three steps. First, all residues except those involving insertions/deletions were changed to the E-Selectin sequence using the INSIGHT-II program (Biosym Technologies, San Diego). If possible, conformations of E-Selectin side chains were kept similar to those of MBP, otherwise they were based on rotamer libraries [Ponder and Richards, J. Mol. Biol. 193, 775–791 (1987)], packing and hydrogen-bonding considerations. Second, possible loop structures for the E-Selectin insertions/deletions were gleaned from a search of crystal structures in the Protein Data Bank [Berstein et al., J. Mol. Biol. 112, 535–542 (1977)] using the INSIGHT-II program. Third, each of the thirty water molecules present in the MBP crystal structure was evaluated regarding its retention in the E-Selectin model. Only seven waters were included in the E-Selectin model, four of which corresponded to MBP water molecules 23, 24, 25 and 30.

The E-Selectin model was subjected to 6000 cycles of energy minimization using the DISCOVER program (Biosym Technologies, San Diego). The all-atom AMBER forcefield [Weiner et al. J. Am. Chem. Soc. 106, 765–784 (1984), Weiner et al. J. Comp. Chem. 7, 230–252 (1986)] was used for all calculations, employing a 14Å cutoff for nonbonded interactions and a linear dielectric (e=4.0*r). Hydrogen atoms were added to the structure using INSIGHT-II and positions of hydrogens on Ser, Thr and Tyr side chains and on water molecules were checked visually for proper alignment in hydrogen-bonds, if present. Energy minimization was performed in six stages of 1000 cycles each. In stage 1, steepest-descents minimization was employed with Ca atoms of residues S2-V27, Q30-S40, Y49-R54, W60-V61, N75-N82, E88-I93 and W103-T119 constrained to their initial positions using a force constant of 100 kcal/Å. 105 hydrogen-bond constraints (50 kcal/mole) were also invoked involving primarily hydrogen-bonds between residues in the b-strands and a-helices. This allowed loop structures and sidechains to move while preserving the integrity of the secondary structure present in the E Selectin model. In stages 2 and 3, the Ca tether force constant was reduced to 50 and 10 kcal/Å, respectively, and conjugate gradients minimization was utilized. In stages 4 and 5, the Ca constraints were released and, finally, in stage 6 the hydrogen-bond constraints were released. The MBP crystal structure includes two $Ho^{2+}$ atoms which occupy the two $Ca^{2+}$-binding sites in MBP. E-Selectin retains one $Ca^{2+}$-binding site, but looses the second (see results). Since the AMBER forcefield (Weiner et al. 1984, and 1986, Supra) does not include a representation for $Ca^{2+}$, the $Ca^{2+}$ atom was removed and the sidechains which coordinate the $Ca^{2+}$ (E80, N82, E88, N105, D106) were fixed throughout the minimization procedure.

B. Results

Characterization of a Panel of E-Selectin Antibodies

Figure 1A:
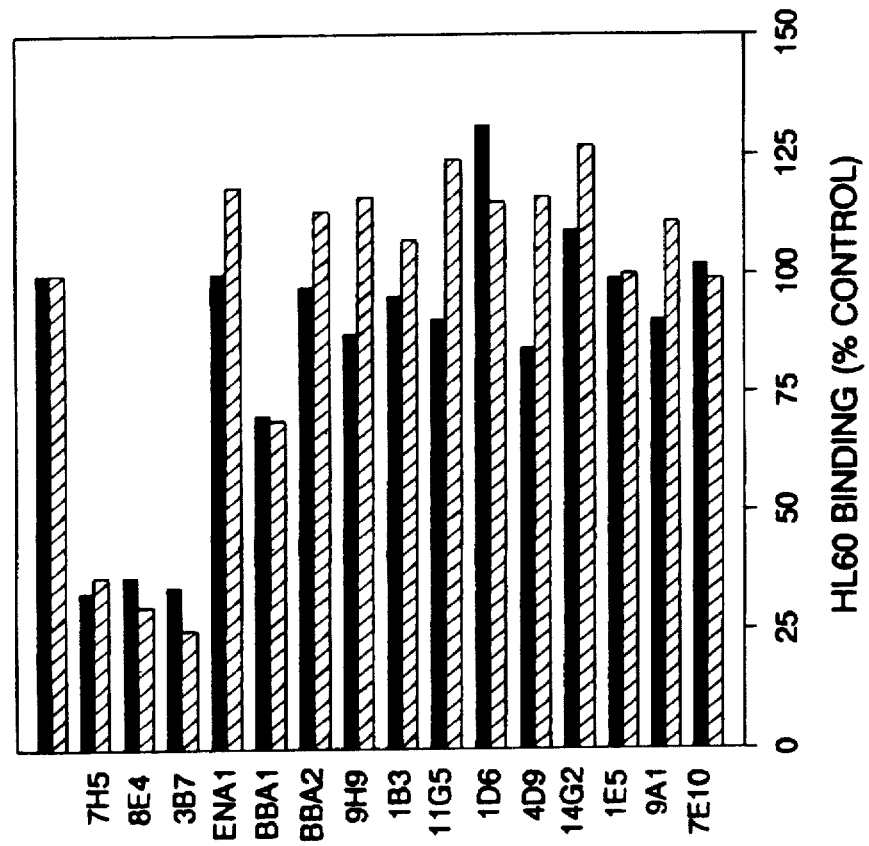

To facilitate the study of E-Selectin structure and function, we generated a panel of blocking and non-blocking Mabs directed against human and rabbit E-Selectin (see Experimental Procedures). Three anti-human E-Selectin Mabs (7H5, 8E4, and 3B7) were found to inhibit the adhesion of HL60 cells to cytokine activated HUVECs and E-Selectin transfected COS cells (FIG. 1A). Cross reactivity studies demonstrated that these three blocking Mabs did not recognize rabbit E-Selectin (FIG. 1B), a result that facilitated the mapping of the epitopes recognized by these Mabs (see below). The commercially available anti-human E-Selectin MAbs, BBA1, BBA2 and ENA-1, also did not cross react with rabbit E-Selectin (FIG. 1B). While none of these three commercial MAb's significantly blocked E-Selectin-mediated HL60 adherence in our cell adhesion assay (FIG. 1A), BBA2 has clear adhesion blocking activity in cell adhesion assays done at low temperature [Pigott et al., J. Immunol. 147, 130–135 (1991); C. Phipps-personal communication] and ENA-1 has been shown to block neutrophil adhesion to activated HUVECs [Leeuwenberg et al., *Clin. exp. Immunol.* 81 496–500 (1990)]. Furthermore, BBA2 and ENA-1 both effectively inhibit binding of E-Selectin to immobilized sLex glycolipid (Foxall et al., 1992, Supra). Since sLex is the major carbohydrate ligand for E-Selectin on the leukocyte cell surface, it seemed likely that analysis of the epitopes recognized by this panel of blocking antibodies (7H5, 8E4, 3B7, BBA2 and ENA-1) would indicate the region(s) of E-Selectin involved with carbohydrate recognition and resultant cell adhesion. In addition, the mapping of regions recognized by other, non-blocking Mabs should confirm and emphasize the site(s) found for blocking antibodies by indicating regions of the lectin domain not involved with carbohydrate recognition and cell adhesion. Therefore, the initial step in analyzing the regions of E-Selectin involved in carbohydrate interactions consisted of mapping the epitopes recognized by blocking and non-blocking anti-E Selectin Mabs.

Analysis of E-Selectin Monoclonal Antibody Binding

The E-Selectin mutagenesis strategy was driven by two major considerations. The first consideration derived from previous work on the localization of the epitope recognized by the murine L-Selectin blocking Mab, Mel 14 [Bowen et al., *J. Cell Biol.* 107, 1853–1862 (1990)]. This work demonstrated that this antibody recognized a region within the N-terminal 53 amino acids of murine L-Selectin. It was assumed that blocking antibodies directed against E-Selectin may also recognize epitopes contained within the N-terminus of the lectin domain, and this region was, therefore, targeted for mutagenesis. A second strategy targeted positively-charged residues in the lectin domain using both alanine-scanning and species homologue mutagenesis protocols [Cunningham and Wells, *Science* 244, 1081–1085 (1989)]. The fact that all selectins require a negatively charged sialic acid as part of the carbohydrate ligand along with other observations could be interpreted as indicating the formation of a charge-mediated interaction between the negatively-charged carboxylate of the sialic acid and one or more positively charged residues in the lectin domain.

Figure 3:
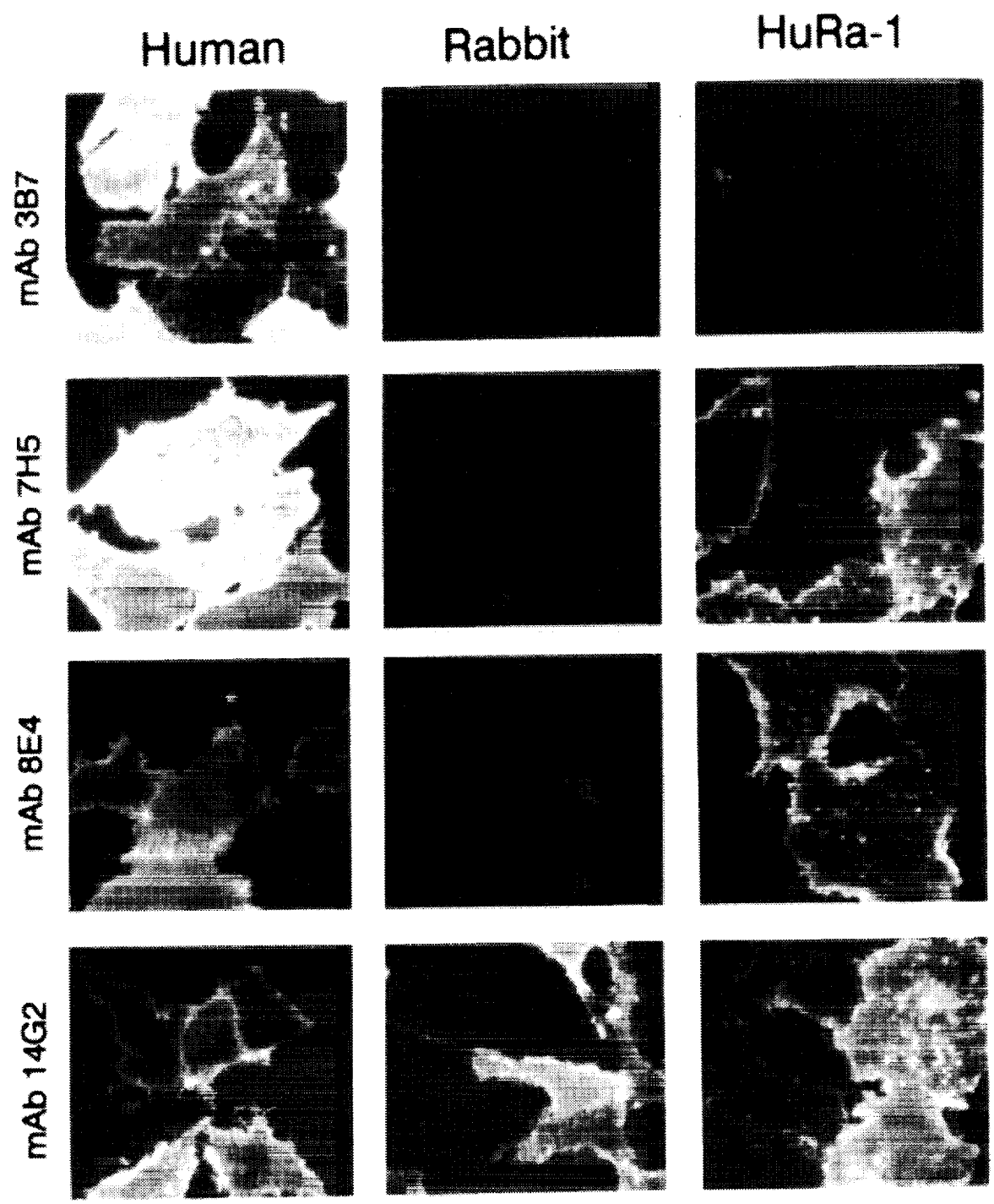
Figure 4:
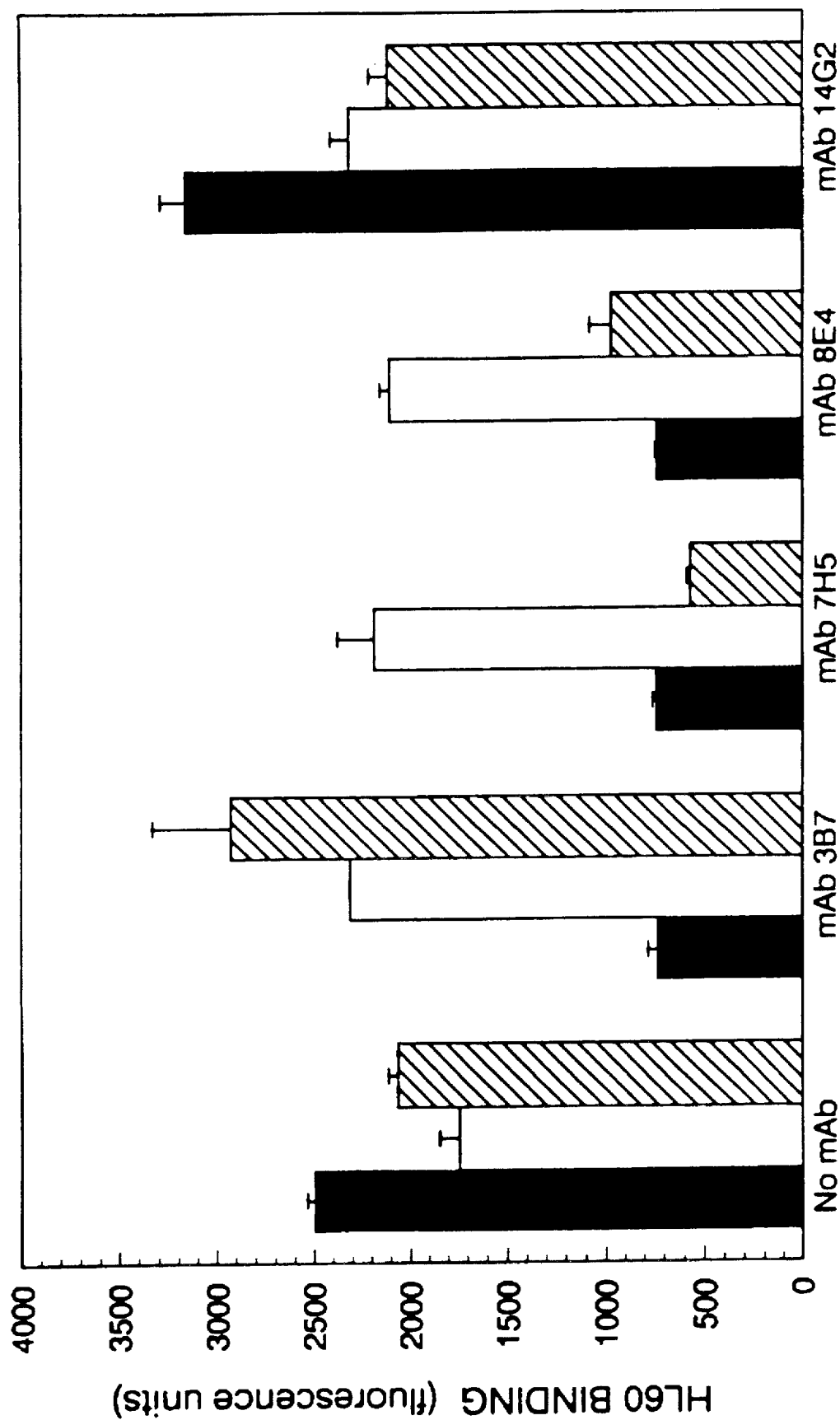

As described above, none of the anti-human E-Selectin blocking Mabs reacted with rabbit E-Selectin, and analysis of the amino acid sequences of the lectin domains of human and rabbit E-Selectin showed that 5 of 16 differences were clustered in the N terminal nine amino acids (FIG. 2A). To determine whether blocking MAbs map to this region, a chimeric protein containing rabbit E-Selectin lectin and egf-like domains with the N-terminal 9 amino acids replaced by the corresponding sequence from human E-Selectin was generated (Hu-Ra-1) (see FIG. 2B). This construct was produced as a fusion of the lectin and egf-like domains with a region of CD16 sufficient to allow anchoring of the expressed protein to the cell surface by a glycosyl-inositol phosphate linkage (FIG. 2B). The egf-like domain was included because previous data suggested that the overall conformation of selectin lectin domains required the presence of the adjacent egf-like domain. Indirect immunofluorescence on COS cells transfected with human lectin-egf-CD16, rabbit lectin-egf-CD16, or the human-rabbit chimera (Hu-Ra-1) demonstrated that human amino acids 1–9 in the rabbit E-Selectin background were sufficient to confer MAb 7H5 and 8E4 binding but not MAb3B7 binding (FIG. 3). In similar experiments, ENA-1, but not BBA2, bound to HuRa-1 (not shown). In addition, the adhesion of HL60 cells to Hu-Ra-1 transfected COS cells was inhibited by MAb's 7H5 and 8E4, but was unaffected by MAb 3B7 or the non-blocking MAb 14G2 (FIG. 4). These data were consistent with the localization of the epitopes recognized by three blocking Mabs (7H5, 8E4 and ENA-1) to the N-terminal 9 amino acids of human E-Selectin.

To facilitate further Mab mapping analysis and allow for direct carbohydrate binding studies (see below), mutations were introduced into the lectin domain of an E-Selectin-human immunoglobulin G (IgG) chimera that is similar to a previously described L-Selectin-IgG chimera (FIG. 2B) [Watson et al., 1990, 1991, Supra; Foxall et al., 1992, Supra). The E-Selectin-IgG chimera allowed for easy quantitation of each individual mutant by analysis of the amount of human IgG produced from each transient cell transfection assay (see Experimental Procedures). The inclusion of the human IgG tail also allowed for rapid analysis of the ability of each mutant to bind the anti-E-Selectin antibody panel, as well as to immobilized sLex, by use of labeled anti-IgG antibody. In this way, mutants that affected global lectin structure (loss of recognition by all MAbs), localized structure (loss of recognition by a subset of Mabs), and carbohydrate recognition (loss of sugar recognition with retention of recognition by most or all Mabs) could be rapidly differentiated.

FIG. 5 shows a number of mutations that appear to affect the binding of various monoclonal antibodies to E-Selectin. Since the chimeric construct of the lectin domains of human and rabbit E-Selectin (HuRa-1) identified the N-terminal nine amino acids as forming at least part of the epitopes for three blocking antibodies (8E4, 7H5 and ENA-1), we first constructed further mutants within this region, concentrating on the five positions (residues 2, 4, 5, 7, and 9) which differ between rabbit and human. A human E-Selectin-IgG chimera in which residues 2, 4, and 5 were mutated retained binding to the entire panel of antibodies, indicating that these amino acids are not critical for MAb binding (data not shown). However, a mutation which replaces the human E-Selectin amino acids at positions 7 and 9 with their counterparts found in the rabbit E-Selectin sequence resulted in loss of binding of antibodies 7H5, 8E4 and ENA-1 (FIG. 5A). The loss of binding of these 3 mAb's directly corresponds to the gain of binding demonstrated with the HuRa-1 chimera. Another N-terminal mutant, E8A, was found to abolish the binding of BBA2 and ENA 1 (FIG. 5C). Thus, in agreement with the human-rabbit chimera studies described above, residues at positions 7, 8, and 9 of the E-Selectin lectin domain contribute to the epitope recognized by four anti-E-Selectin blocking Mabs.

Figure 5A:
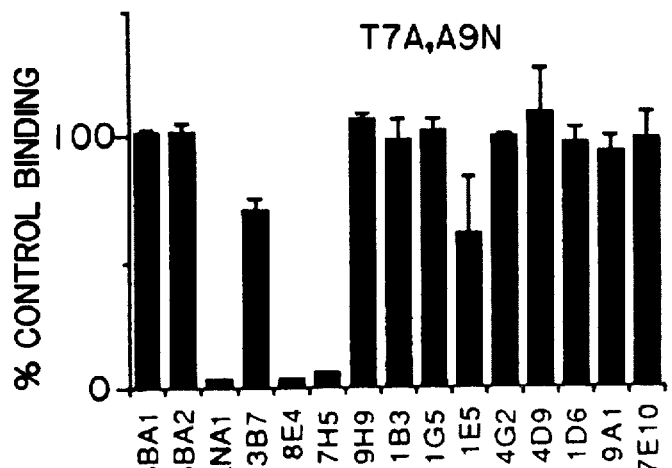
Figure 5B:
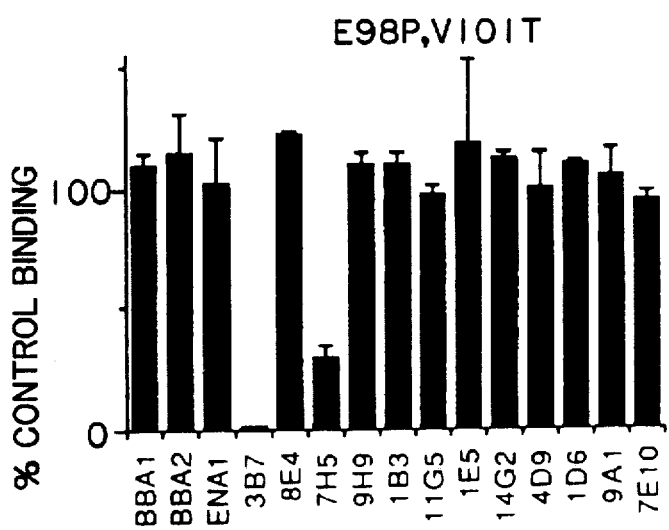

The mutations at positions 7, 8 and 9 enabled the mapping of all blocking antibodies except for Mab 3B7. Replacement of the human residues with their rabbit counterparts at other sites of the E-Selectin lectin domain revealed that a double mutation at residues 98 and 101 completely abolished the binding of this blocking Mab (FIG. 5B). Importantly, the converse experiment was also done where the human residues at these two sites (98 and 101) were placed into the HuRa-1 background. The resultant mutant was found to bind Mab 3B7, thus confirming that this site contained an epitope recognized by this blocking Mab (data not shown). Finally, an E-Selectin-IgG mutant which contained a valine to alanine replacement at position 101 retained binding to Mab 3B7, indicating that the E at position 98 was a crucial component of the 3B7 epitope.

Figure 5C:
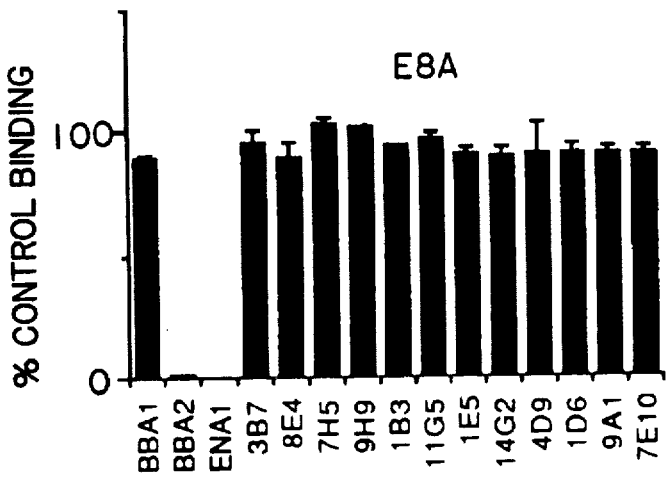
Figure 5D:
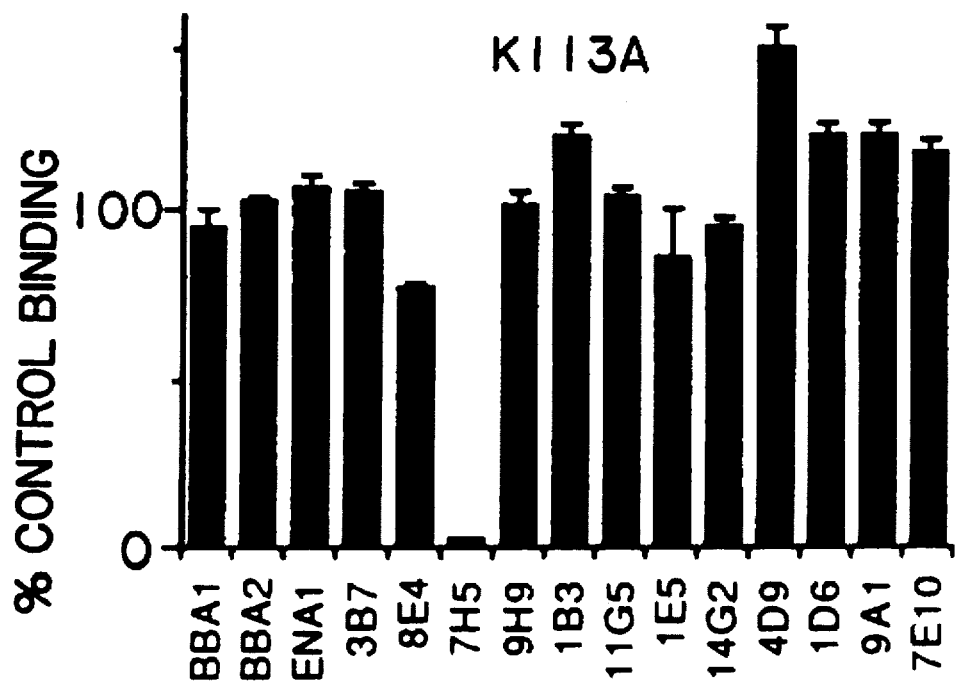

The complexity of the epitope recognized by the 7H5 blocking Mab is revealed by the mutation K113A (FIG. 5C). This mutation, which is at the C-terminus of the lectin domain, completely abolishes binding of this MAb. Since the binding of 7H5 was also abolished by two point mutations made at the N-terminus of the lectin domain (positions 7 and 9, FIG. 5A), it may be concluded that the epitope recognized by this blocking antibody is derived from both the N- and C-termini. Indeed, the partial loss of 7H5 binding found for mutations at residues 98 and 101 (FIG. 5B) was consistent with the close alignment of this region with the N and C terminal sites recognized by this Mab as well. One interpretation of this result is that these regions may be closely aligned in the tertiary structure of the lectin domain (see below).

Figure 5E:
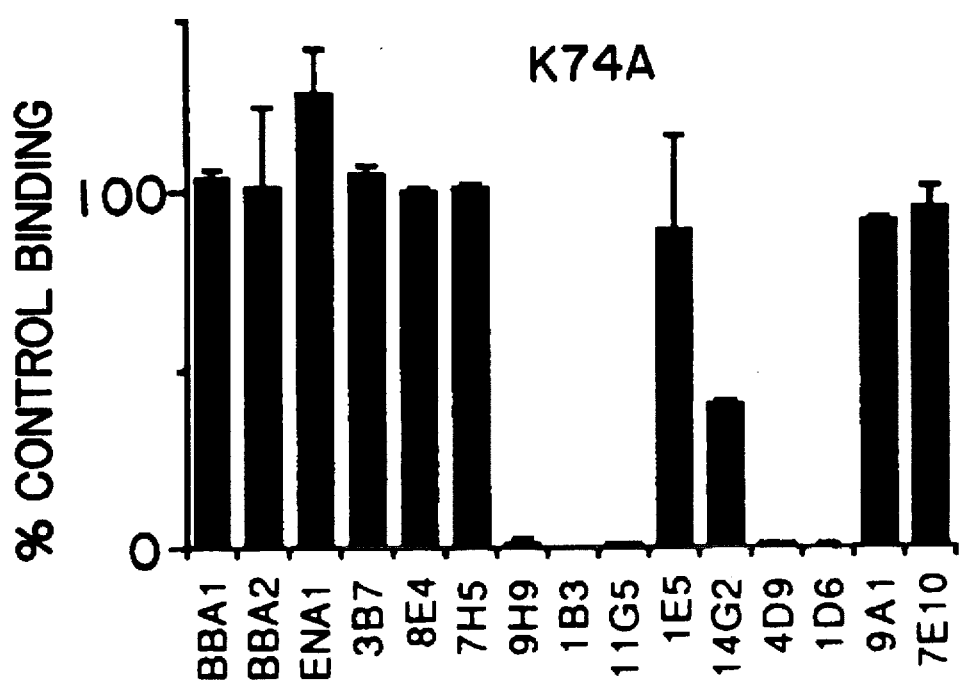

The binding of all of the non-blocking Mabs did not appear to be grossly affected by mutations that disrupted blocking Mab recognition (FIGS. 5A–D). This was consistent with these two classes of Mabs recognizing distant sites in the lectin domain. For example, mutant K74A completely lost binding of a number of these non-blocking antibodies (9H9, 1B3, 11G5, 4D9 and 1D6) and partially lost binding of another (14G2) (FIG. 5E). This mutant did not affect the binding of any of the blocking Mabs that we analyzed, suggesting that this region of E-Selectin may not be directly involved in carbohydrate recognition.

Lastly, a number of mutants (M10A, Y12A, E14A, I93A, Y94A, I95A, K96A, E98A and M103A) resulted in the loss of binding to all of the antibodies in the anti-E-Selectin panel, including 9A1 and 7E10 which recognize determinants in the complement binding like domains 1 and 2 of E-Selectin. This result was obtained even though normalized amounts of these mutants, based upon human IgG concentrations, were added to the antibody-coated wells. These mutations, therefore, appeared to have global effects on the recombinant E-Selectin domains, and the apparent lack of monoclonal antibody reactivity could have been due to denaturation and/or degradation.

Carbohydrate Recognition by E Selectin Mutants

While the blocking Mab mapping data described above were consistent with the involvement of the N- and C-terminal regions as well as the region surrounding residues 98 and 101 of E Selectin with carbohydrate recognition, the large shadow cast on an antigen by a bound monoclonal antibody [typically 680–880 Å$^2$ [Jin et al., 1992, Supra; Davies and Padlan, *Ann. Rev. Biochem.* 59, 439–473 (1990)] may cause blocking by steric hindrance of carbohydrate recognition sites relatively distant from the antibody epitope. Therefore, we analyzed the ability of a number of the E-Selectin-IgG mutants to bind to sLex glycolipid [Kameyama et al., *Carbohydrate Res.* 209, c1–c4 (1991)] that had been immobilized on plastic microtitre wells. This assay has been validated previously (Foxall et al., 1992, Supra), and the binding of the E-Selectin-IgG chimera has been shown to be calcium dependant, inhibited by E-Selectin blocking Mabs and dependant upon the presence of the alpha 2–3 sialic acid form of the carbohydrate.

Figure 6A:
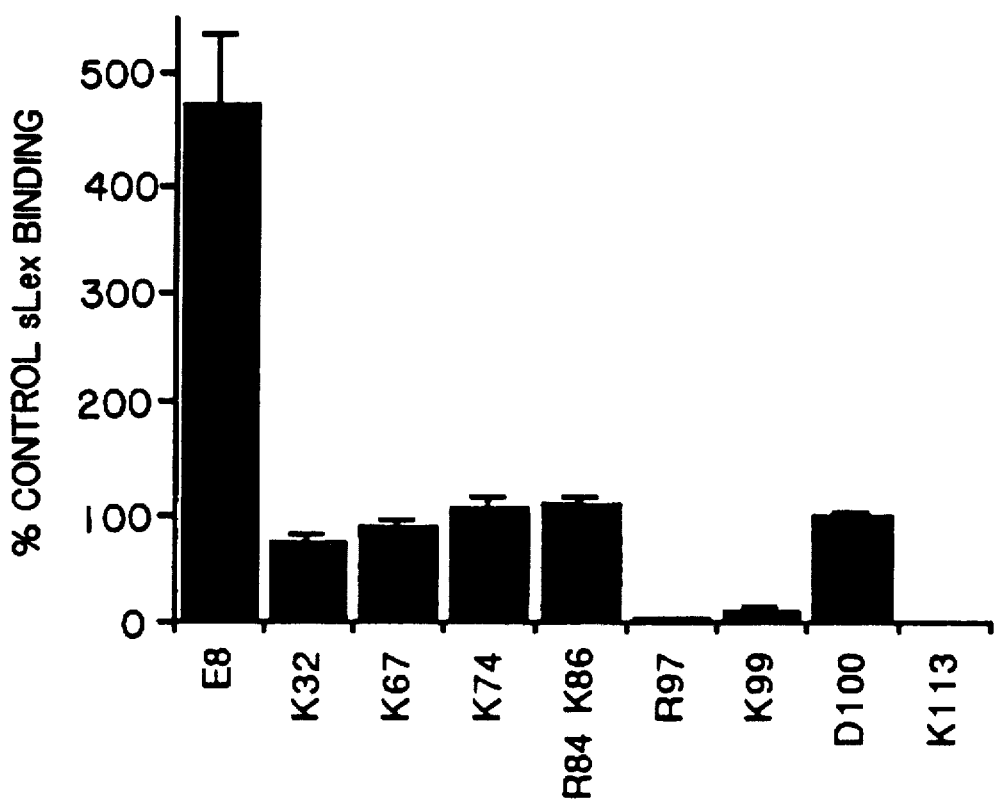
Figure 6B:
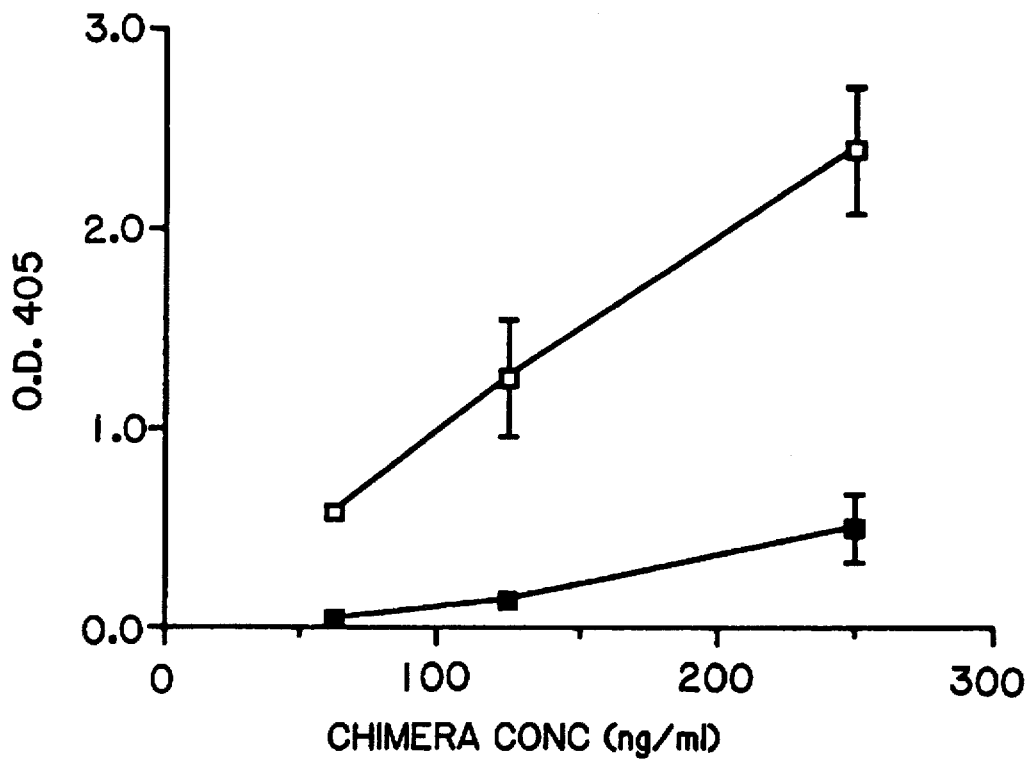

As can be seen in FIG. 6A, three different types of results were obtained with the various mutants analyzed. A number of mutations did not affect the binding of E Selectin to immobilized sLex. These mutations were found to be of the type that either did not affect the binding of any monoclonal antibody (mutants K32A, K67A, and R84A, K86A) or affected binding of only non-blocking antibodies (mutant K74A). This result was consistent with the previously mentioned possibility that this region of E-Selectin was not involved with carbohydrate recognition. Another type of effect was exemplified by mutations at positions R97, K99 and K113. Conversion of any of these sites to alanine either completely (R97 and K113) or almost completely (K99) abolished the binding of E-Selectin to sLex. While mutations at R97 and K99 were found to have no effect on the binding of blocking antibodies, mutation at K113 was found to completely abolish the binding of blocking antibody 7H5 (see above). In addition, mutation at sites 98 and 101, adjacent to R97 and K99, abolished the binding of another blocking Mab, 3B7. These results unified the locations of blocking Mab binding sites with residues that were critical for carbohydrate recognition, and were consistent with the direct involvement of these regions of E-Selectin with carbohydrate binding. The final, somewhat unexpected, effect of E-Selectin mutation on sLex binding was exemplified by the E8A mutant. FIG. 6A shows that this mutant appeared to show enhanced binding to sLex when the mutant was added to wells at the same concentration as wild type E-Selectin chimera. A dose response curve comparing the E8A mutant with wild type E-Selectin (FIG. 6B) reveals that the mutant bound ~5 fold more avidly to sLex than wild type. This enhanced binding by mutant E8A was completely calcium dependant and did not occur on the inactive alpha 2-6 sialic acid form of the carbohydrate (data not shown). As described previously, mutations in this region (i.e. at residues 7,8 and 9) profoundly affect the binding of several blocking Mabs. Thus, it is likely that this region of E-Selectin also plays a critical role in carbohydrate recognition.

A Model of E Selectin

While the results described above allow for a number of important conclusions about the regions of the E-Selectin linear sequence involved in carbohydrate recognition, their relevance would be enhanced if they could be applied to a structural model of the lectin domain of this protein. In the absence of crystallographic data, a three-dimensional model of a molecule can be constructed using structural coordinates of related molecules [Greer, *J. Mol. Biol.* 153, 1027–1042 (1981)]. Recently, the X-ray structure of the mannose binding protein (MBP), a type C lectin that is homologous to the lectin domain of E-Selectin, was determined (Weis et al., 1991, Supra). In order to more fully understand the relative importance of the functional mutations described above, we, therefore, used these structural data to develop a model of the E-Selectin lectin domain.

Derivation of the E-Selectin lectin model from the MBP coordinates was based on secondary structure common to both, encompassing 78 (of 121) E-Selectin residues (Weis et al., 1991, Supra) (FIG. 7). Three models of E-Selectin were evaluated, differing only in the conformation of two surface loops: S43-Y48 and Y94-D100, corresponding to MBP K152-S154 and V199-D200, respectively. The S43-Y48 loop contains a three residue insertion relative to MBP while the Y94-D100 loop contains a five residue insertion. The E-Selectin model prior to energy-minimization had a root-mean-square (r.m.s.) deviation of 0.17Å (78 Ca atoms) while that of the best energy-minimized model was 0.68Å. For comparative purposes, we also subjected the MBP crystal structure to the same energy-minimization regimen as utilized for the E-Selectin model. The minimized MBP (molecule 1 only) showed a Ca r.m.s. deviation of 0.45Å (residues K110-C217, i.e. excluding seven N- and C-termini residues) versus the crystal structure. Hence the energy-minimization regimen maintained the secondary structure of the E-Selectin model; this was accomplished by initially constraining the secondary structure Ca atoms and hydrogen-bonds during minimization.

Weis (Weis et al., 1991, Supra) noted the presence of small and large hydrophobic cores in MBP that were critical for overall structure. For the small core only two of six residues are conserved in E-Selectin (G52, A115) though the model could accommodate the other four E-Selectin side chains without disturbing the protein fold. In the large core only six of fourteen residues are conserved. One substitution, A155(MBP) to Y49(E-Selectin), necessitated moving a-helix-2 (K32-L42) slightly away from the protein center in order to accommodate introduction of the Y49 sidechain. This Y49 side chain interacts with the two loops S43-Y48 and Y94-D100 mentioned above. At the opposite (N-terminus) end of the helix, the substitution of P138(MBP) to I29(E Selectin) also contributed to the slight shift in a-helix-2. However, the substitutions in E-Selectin in the large hydrophobic core fill the internal space created by the slight shift of a-helix-2. Thus, the relatively large number of amino acid changes in the hydrophobic core regions of MBP and the E-Selectin lectin domain could be accommodated by the model.

The MBP crystal structure contains two putative $Ca^{2+}$-binding sites which, in the crystal structure, are occupied by two $Ho^{2+}$ ions. As noted by Weis, Supra, site 2 is retained in E-Selectin: E80 Oe2, N82 Od1, E88 Oe2, N105 Od1, D106 Od2, D106 backbone carbonyl oxygen, and one water molecule coordinate this $Ca^{2+}$. The other $Ca^{2+}$-binding site is probably not present in E-Selectin, also noted previously (FIG. 7). While D89 (D194 in MBP) is conserved in E-Selectin, D161 in MBP is replaced by K55 in E-Selectin and two other side chains which coordinate the MBP site 1 $Ca^{2+}$, i.e. E165 and D188, are replaced by N57 and N83 in E-Selectin. While an Asn side chain could still coordinate a $Ca^{2+}$ via its Od1 atom, N57 is adjacent to a two residue deletion and the loop of which it is a part probably changes conformation. Likewise, N83 is part of a loop which has a proposed conformation in E-Selectin different from that in MBP. Though this loop contains no insertions or deletions, the MBP sequence HGSG forms a Type II' reverse turn with the Gly at position 4 having a backbone conformation allowable only for Gly (136°, 148°). The E-Selectin sequence RQKD necessitated a different loop conformation due to the G to Q and G to D replacements. Thus, only one calcium binding site appears to exist in the E-Selectin lectin domain.

Of course, the most interesting aspect of the model is the location of the amino acid side chains whose mutation appeared to affect monoclonal antibody binding and/or sLex recognition. As can be seen from the model (FIG. 7), the amino acid residues involved in blocking Mab recognition appear to form a patch on the surface of the lectin domain near the antiparallel beta sheet formed by the disulfide-linked N- and C-termini and the adjacent disulfide-linked loop formed by the two internal cysteines. Thus, amino acid side chains at positions 7,8,9, 98, 101 and 113, all of which affected the binding of various blocking Mabs, are all found to be very close to each other on the surface of E-Selectin (within a patch of ~80 square angstroms). Of particular importance was the close alignment of the side chains of residues 7, 9 and 113 which was consistent with the effect of mutations at these residues on the binding of the 7H5 blocking Mab. The partial effect of mutations at residues 98 and 101 on 7H5 binding is also consistent with the model, since the disulfide-bonded loop containing these residues is also close to residues 7, 8, 9 and 113. The model also reveals that the side chain recognized by the non-blocking antibodies (K74) is found on a side of the lectin domain that is opposite to that which appears to bind the blocking antibodies (FIG. 7). This result is consistent with the region recognized by non-blocking antibodies being a considerable distance from the carbohydrate recognition site. Thus, the model of E-Selectin suggests that a relatively small patch of the molecule recognized by blocking monoclonal antibodies appears to be involved with carbohydrate recognition.

Examination of the location amino acids found to be involved with sLex binding is consistent with the interpretation that the region recognized by the blocking monoclonal antibodies is involved with carbohydrate recognition. The close spacing of residue E8, whose mutation was found to enhance sLex binding, and residue K113, whose mutation was found to abolish carbohydrate binding, can be clearly seen on the model. Perhaps more interesting is the close proximity of two other mutations that either completely or almost completely abolish sLex recognition. As can be seen from the model in FIG. 7, residue R97, whose mutation virtually abolished sLex recognition, is found quite close to the K113 site whose mutation also abolished sLex binding. The K99 mutation, which also showed a profound negative effect on sLex binding, was also found near this region. Mutation of another residue within this same loop (D100) had no effect on sLex binding (FIG. 6A). These results are consistent with the recognition of sLex by a relatively small region of the E-Selectin lectin domain comprised of residues from the N and C termini and the small disulfide-bonded loop. In addition, they also suggest a role for at least one positively-charged amino acid side chain (R97, K99 or K113) in the recognition of this carbohydrate ligand. Finally, the model shown in FIG. 7 demonstrates that a number of side chains whose mutation did not affect sLex binding are located on a side of the molecule that is quite distant from the apparent sLex binding site.

C. Discussion

The foregoing data provide valuable information about the interactions between E-Selectin and its carbohydrate ligand, sLex. The work disclosed in this example is unique in that it combines the mapping of blocking and non-blocking monoclonal antibody binding sites with the ability of a given E-Selectin mutant to bind to its natural carbohydrate ligand, sLex. The agreement between blocking Mab mapping data and the location of mutations that affect sLex binding is consistent with the hypothesis that the small region of the E-Selectin lectin domain identified here is directly involved with binding to the previously-defined face of sLex (Tyrrell et al., 1991, Supra; Berg et al., 1991, Supra). This proposal is also supported by the fact that many non-blocking monoclonal antibodies appear to map to the opposite side of the lectin domain.

One of the most interesting aspects of the mutagenesis described here is the discovery that two positively charged residues (R97 and K113) that are critical for sLex recognition appear very close together on the E-Selectin model (FIG. 7). A major supposition of the mutagenic analysis was based upon the potential importance of positively charged residues, and the discovery that the deletion of either of these side chains has negative effects on carbohydrate recognition supports the possibility that positively charged side chains in Selectin lectin domains are involved in carbohydrate recognition (Stoolman et al., 1987, Supra; Yednock et al., 1987, Supra; Lasky et al., 1989). One possible means by which this recognition could be accomplished is by charge interaction between these side chains and the carboxylate group of the sialic acid residue found in sLex. The importance of the carboxylate group in sLex binding is underlined by organic synthesis studies that have revealed that an sLex-like compound with only a carboxylic acid group at the sialic acid site can be effectively recognized by E Selectin (J. Musser and B. Brandley-unpublished observations). Thus, it seems likely that some type of charge-mediated interaction may be involved with sLex adhesion to E Selectin. All three selectins appear to require sialic acid for adhesion, and it is interesting that, while K113 is found in all three selectins from a number of different species, a positively charged residue (R) is found at position 97 of L- and E-Selectin only, while human P-Selectin contains an S at this site. The conservation of a K at position 113 of all selectins, together with the mutagenesis analysis described here, is consistent with a direct role for this residue in sialic acid recognition, perhaps by the formation of a salt bridge or hydrogen bond. The less stringent conservation between selectins at position 97 argues that this residue, while clearly involved with carbohydrate recognition, may have a less direct effect on sugar binding than residue K113. Interestingly, mutation of D100 to alanine showed no effect on sLex binding, consistent with the supposition that only the positively charged residues in this area are involved with sLex recognition.

The data disclosed here also provide strong evidence for involvement of the N-terminus of E-Selectin in carbohydrate binding. Mutagenesis of the N-terminus was initially inspired by previous data that demonstrated that the anti-murine L-Selectin blocking Mab, Mel 14, appeared to map to the N-terminus of this glycoprotein. In agreement with that study, a number of anti-E-Selectin blocking monoclonal antibodies were found to recognize residues in the N-terminus of this glycoprotein as well. In fact, of the five blocking antibodies that we have analyzed, four (BBA 2, ENA 1, 8E4 and 7H5) have been directly shown to bind to this region of E-Selectin, consistent with the important role of this site in carbohydrate recognition. The finding of a residue (E8) in this region whose mutation to A enhanced carbohydrate binding was also consistent with the involvement of this site in sLex recognition. In addition, the enhanced recognition of sLex by mutation at position 8 may be of biological significance. As was pointed out earlier, selectins appear to mediate a relatively low affinity "rolling" type of adhesion as a precursor to firmer adhesion mediated by leukocyte integrins (Butcher 1991, Supra; Lawrence and Springer 1991. Supra; Ley et al., 1991, Supra; VonAndrian et al., 1991, Supra). It is possible that the N terminal region of E selectin has evolved to decrease the relative affinity of carbohydrate recognition by incorporation of a charged residue at this site. Interestingly, the other two selectins (L- and P-) contain a positive charge at this site (K), and mutation of the K in L-Selectin to an A also appears to similarly enhance sLex recognition by 5 to 10 fold (see Example 2). It thus seems possible that the charge at this site may serve to decrease the affinity of carbohydrate binding, consistent with a close association of carbohydrate with this region.

While the residues delineated here may be directly involved with sLex recognition, indirect effects may also play a role in the loss of binding by some of these mutants. For example, mutation of residue K99 to alanine partially decreased sLex recognition by E-Selectin. This residue was relatively distant from the closely opposed R97A and K113A mutations which profoundly affected sLex binding, consistent with the possibility that the K99A mutation may have affected sLex binding by an indirect mechanism. One such indirect effect would be if the K99 to A mutation changed the conformation of this loop such that R97 no longer formed a stable contact with the carbohydrate. Another indirect effect may involve interactions between the egf-like and lectin domains. Previous data have clearly demonstrated, in both the L- and E-Selectin adhesion molecules, that removal of the egf-like domain results in a loss of epitope recognition by antibodies directed against the lectin domain (Bowen et al., 1990, Supra; Walz et al., 1990, Supra). These results were consistent with the possibility that one role for the egf domain is in the mediation of lectin domain structure, perhaps by intimate contacts between residues in each of these motifs. It is, therefore, possible that loss of binding by one or more of the mutants described here may have been due to a decreased level of interaction between the lectin and egf-like domains. However, it must be emphasized that crystallography studies of point mutants in other proteins show structural differences to be highly localized (Jin et al., 1992, Supra; Wells 1991, Supra and references therein). Additionally, it should be noted that the retention of binding by the lectin-specific monoclonal antibodies to mutants R97A and K99A is not consistent with the major disruption of lectin domain structure that might be expected by inhibition of some of the interactions between the lectin and egf-like domains (Bowen et al., 1990, Supra; Walz et al., 1990, Supra).

Recently, Geng and coworkers showed that a mAb capable of inhibiting neutrophil binding to P-Selectin mapped to residues 19–34 of this molecule, and that a peptide corresponding to this stretch also inhibited neutrophil binding to P-Selectin (Geng et al., 1991, Supra). In the model of E-Selectin presented here, residues 19–34 form a loop which is on the opposite side from the site where sLex appears to bind. The two mutants made within this sequence in E-Selectin either did not affect sLex or mAb binding (mutant K32A) or resulted in a misfolded protein (mutants Y18A, Q20A, R22A). Thus, although an extensive mutational analysis of this loop was not performed, our data are not consistent with its direct involvement in carbohydrate recognition by E-Selectin.

In addition to the mutations described above, another substitution, N82D, in the E-selectin lectin domain was found to dramatically affect sLex recognition. The results of antibody capture and 2'3 sLex binding studies are shown in FIG. 16. Although this substitution did not affect the binding of any of the mAb's (A), it completely abolished binding of E-selectin to 2'3 sLex (B). The asparagine at position 82 is predicted to participate in the $Ca^{++}$ chelation via its Oδ1 molecule. Removal of the amino group from this aspargine in the N82D substitution would not be predicted, a priori, to disrupt this interaction. However, it was thought possible that the N82D mutant had lost ligand binding due to a reduced calcium affinity. To test this possibility, the N82D mutant was tested for 2'3 sLex binding in the presence of added calcium. As seen in FIG. 16 (C), the N82D mutant did not bind sLex even at calcium concentrations as high as 40 mM. Therefore, the loss of binding by this E-selectin mutant is probably not due to a loss of calcium chelation by the lectin domain. Rather, these results implicate a role for the terminal amino group of asparagine at position 82 of the E-selectin lectin domain in ligand recognition by E-selectin.

EXAMPLE 2

Murine L-Selectin-IgG chimeras were prepared essentially as described in Example 1 for E-Selectin. Lysine (K) at amino acid position 8 of the L-Selectin was substituted by alanine (A) following the method of Kunkel et al., 1987, Supra, using the Muta-Gene Phagemid in vitro Mutagenesis Kit (BioRad) according to the manufacturer's instructions. The correct mutant was confirmed by DNA sequencing, and the mutant chimera was transiently expressed and secreted by transfection of human embryonic kidney 293 cells (Watson et al., 1991, Supra). The concentration of the chimera was quantified by ELISA using an anti-human IgG1-Fc specific mouse mAb as described by Watson et al., 1991, Supra). The Sialyl Lewis X binding assay was performed essentially as described in Example 1. The results are shown in FIG. 8.

EXAMPLE 3

A. Experimental Procedures
Flow Cytometric Assay for P-Selectin Ligand

The interaction of P-Selectin and its cellular ligand was studied using a flow cytometric assay. Cells used in this assay were either HL60 cells (maintained in high glucose Dulbecco's MEM plus 10% Hyclone FBS) or fresh human neutrophils. Human neutrophils were purified from heparinised peripheral blood by a Ficoll-Hypaque gradient to remove mononuclear cells, followed by treatment with 3% dextran sulfate to remove red blood cells. The resulting cells were >90% neutrophils. Prior to staining with P-Selectin-IgG both cell types were preincubated in Dulbecco's PBS/ 1% bovine serum albumin/0.1% sodium azide/1% normal rabbit serum (staining medium) for 30–60 mins on ice. After this initial incubation, 1μg of P-Selectin-IgG was added to 100 ul aliquots of $10^6$ cells and incubated for 30–60 mins on ice. The cells were then washed with staining medium and resuspended in 100 ul of staining medium to which was added 2 ul of a phycoerythrin-conjugated F(ab')$_2$ goat anti-human IgG (Fc specific). The cells were incubated for 15–30 mins on ice, washed twice with staining medium, and resuspended in 0.5 ml of staining medium prior to flow cytometric analysis on a FACScan (Becton-Dickinson). To determine that the staining was an interaction of P-Selectin with its ligand, the staining was also done in the presence of 10 mM EGTA. To determine the protease sensitivity and the requirement for sialic acid of this interaction, HL-60 cells in D-PBS and 1%BSA were incubated with either trypsin or Arthrobacter or Clostridium sialidases at 37° C. prior to resuspending in staining medium. To determine the effect of activation on the expression of the ligand, human neutrophils were incubated at 37° C. with 50 ng/ml phorbol myristate acetate for 10 mins prior to resuspending in staining medium. To examine the ability of various carbohydrates to inhibit staining, reagents were added to cells immediately prior to the addition of the P-Selectin chimera and were present until the cells were washed prior to addition of the second stage antibody. A potential complication of this assay arose from the use of selectin-IgG chimeras to stain cells (HL60 cells and neutrophils) which bear human IgG Fc receptors (FcgR, Fanger, M. W., *Immunol. Today* 10: 92–99 (1989)). Adding rabbit IgG (in the form of normal rabbit serum) to the assay medium blocked this binding in most cases. However, in some experiments with human neutrophils, it was necessary to add murine mAb's to human FcgR (Medarex, Inc., West Lebanon, N.H.) to the assay medium to completely block this interaction.

Anti-Selectin Monoclonal Antibodies

The following anti-human P-Selectin monoclonal antibodies were purchased to characterize the mutant chimeras: mAb's AK-6 (CLB-thromb/6) and CRC 81 from BioDesign International (Kennebunkport, Me.), and mAb AC 1.2 from Becton Dickinson (San Jose, Calif.). The anti-E-Selectin mAb's 9A1, 7E10, 3B7, and 9H9 have been described in Example 1.

Construction and Expression of Wild Type and Mutant Chimeras

Production and characterization of the P-Selectin-IgG and E-Selectin-IgG chimeras has been previously described (Asa, D. et al., *J. Cell Biol.* 117: 895–902 (1992)). The PE-1 chimera was constructed in two steps. First, an EcoRI-XhoI fragment encoding the signal peptide, lectin domain, and part of the EGF domain of P-Selectin was removed from a pRK5/P-Selectin-IgG plasmid. pRK5 is disclosed in EP 307,247 published 15 Mar. 1989. This fragment was inserted into a pRK5/E-Selectin-IgG plasmid which had been digested with EcoRI and BglII to remove the E-Selectin signal peptide and most of the E-Selectin lectin domain. Second, the P-Selectin lectin domain was joined in-frame to the E-Selectin EGF domain via oligonucleotide-directed deletional mutagenesis using the method of Kunkel (Kunkel, T. A. et al., *Methods in Enzymol.* 154: 367–382 (1987)) as described in Example 1. The expressed PE-1 construct consisted of the signal peptide and lectin domain from P-Selectin, followed by the EGF, CR1 and CR2 domains of E-Selectin, and the IgG1 hinge, CH2 and CH3 domains common to both the P-Selectin-IgG and E-selectin-IgG constructs.

Amino acid substitutions were introduced into the lectin domain of the P-Selectin-IgG chimera as described in Example 1. Wild type and mutant chimeras were expressed and secreted by 293 cells, quantified and tested for anti-selectin mAb reactivity also as described in Example 1. Mutant chimeras are defined using the nomenclature: K113A is a mutant where the lysine (K) at position 113 is changed to an alanine (A).

Binding of Selectin-IgG Chimeras to Sialyl Lewis x and Sulfatides

Assays for binding of the different selectin-IgG chimeras to immobilized sLe$^x$ glycolipids or sulfatides were performed as described (Asa, D. et al., Supra). Briefly, 2'3 sLe$^x$ glycolipids, 2'6 sLe$^x$ glycolipids, or bovine brain sulfatides (Sigma, St. Louis, Mo.) were dried onto microtitre wells, washed with distilled water, and then blocked with BSA. Biotinylated goat anti-human IgG Fc and alkaline phosphatase-streptavidin (Caltag, South San Francisco, Calif.) were each diluted 1:1000 into 293 cell supernatants containing equal concentrations of wild type or mutant chimeras and allowed to form a complex prior to addition to the wells. These supernatants were then incubated on the sLe$^x$ glycolipid or sulfatide coated surfaces, followed by washing, addition of substrate (p-nitrophenyl phosphate), and measurement of the O.D. at 405 nm.

Generation of a P-Selectin Lectin Domain Model

A model of the P-Selectin lectin domain was generated based on the crystal structure of the rat mannose-binding protein (MBP) (Drickamer, K. et al., *Science* 254:1608–1615 (1991)) as previously described for an E-Selectin lectin domain model (Brandley, B. K. et al., Supra). Briefly, MBP residues were changed to the P-Selectin sequence with the sidechain conformations kept similar to those of MBP where possible. Otherwise sidechain conformations were based on rotamer libraries (Ponder, J. W. and Richards, F. M., *J. Mol. Biol.* 193: 775–791 (1987)), packing and hydrogen-bonding considerations. Possible loop structures for the eleven insertions and two deletions in P-Selectin relative to MBP were gleaned from a search of crystal structures in the Protein Data Bank (Bernstein, F. C. et al., *J. Mol. Biol.* 112: 535–542 (1977)). Finally, the P-Selectin model was subjected to repetitive cycles of energy minimization using the method described for E-Selectin (Brandley, B. K., et al., Supra).

Results

Figure 10A:
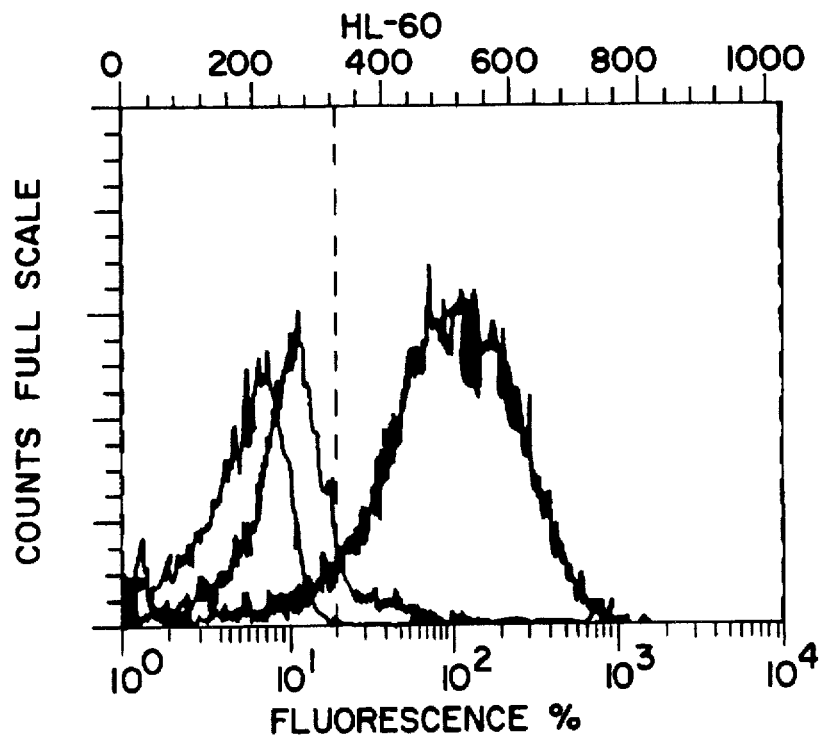
Figure 10B:
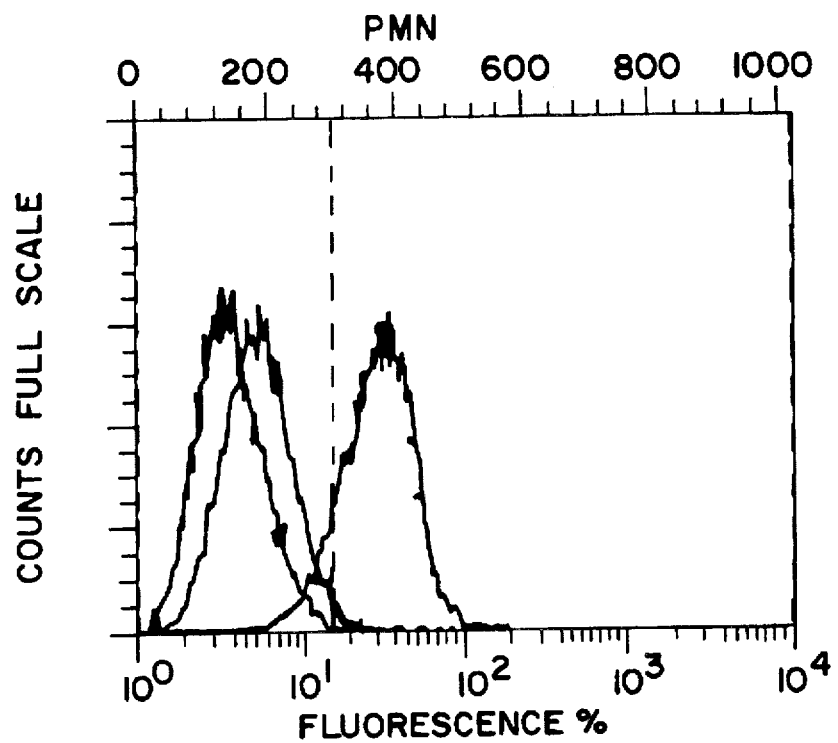
Figure 10C:
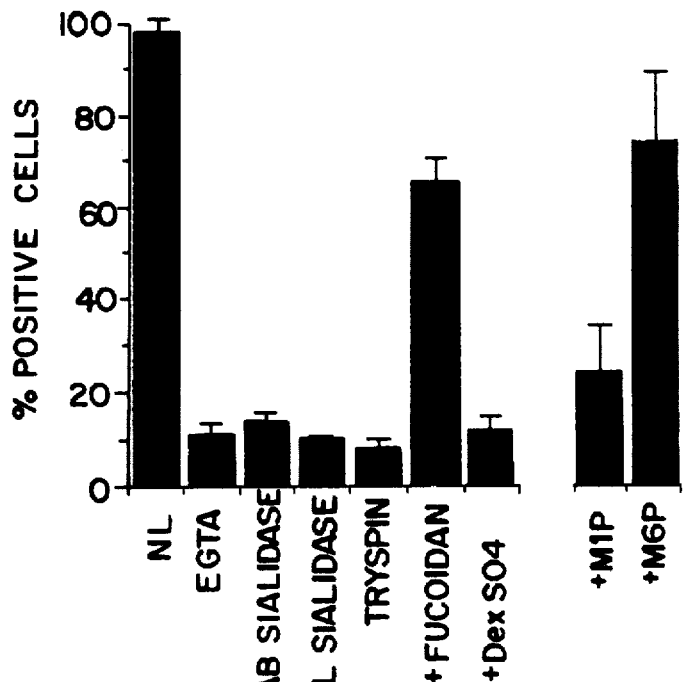
Figure 10D:
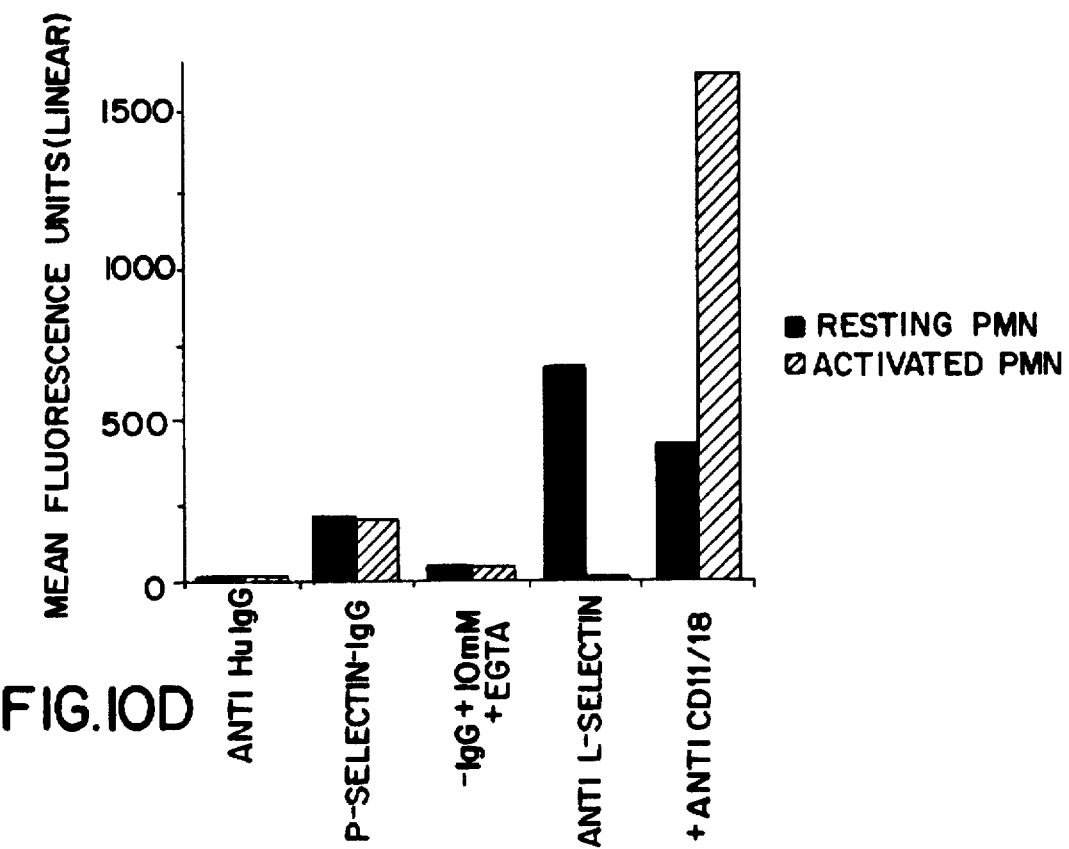

As a starting point for evaluating the residues in P-Selectin responsible for binding ligand, we developed a flow cytometric assay using the P-Selectin-IgG chimera to stain HL60 cells and neutrophils. Whereas E-Selectin-IgG did not bind HL60 cells or neutrophils in this assay, P-Selectin-IgG staining resulted in a strong fluorescence shift for both cell types (FIG. 10, A and B). This binding was inhibited by EGTA, reflecting the calcium requirement for P-Selectin's interaction with its ligand. Further controls indicated that this assay using the P-Selectin-IgG chimera reflects the published characteristics of P-Selectin/ligand binding. In particular, treatment of HL60 cells with either trypsin or sialidase abolished staining (FIG. 10C). Furthermore, P-Selectin-IgG staining was inhibited by dextran sulfate and mannose-1-phosphate, but not fucoidin or mannose-6-phosphate (FIG. 10C). Following activation of human neutrophils with PMA, although surface expression of L-Selectin decreased and surface expression of CD11/18 increased, surface expression of the P-Selectin ligand did not change (FIG. 10D). In addition to neutrophils, monocytes and NK/LGL cells were positive when stained with P-Selectin-IgG (data not shown), which is consistent with the expression of the P-Selectin ligand on these cells.

As noted above, the E-Selectin-IgG chimera did not bind HL60 cells or neutrophils in the soluble FACS assay. We exploited this finding to aid in mapping the region of P-Selectin necessary for conferring this high affinity binding. Since our study with E-Selectin had localized its ligand binding site to a region within its lectin domain, we sought to determine if the apparent differences in E- and P-Selectin binding could be attributed to differences in their lectin domains. Consequently, we constructed a chimera (PE-1) which consisted of E-Selectin-IgG with the E-Selectin lectin domain replaced with the lectin domain from P-Selectin. To see if this chimera was folded correctly, we tested its binding to antibodies specific for the various domains of E- and P-Selectin. The PE-1 chimera reacted well with antibodies to the CR1 and CR2 domains of E-Selectin (mAb's 9A1 and 7E10, Table I) but not with antibodies to the lectin domain of E-Selectin (mAb's 3B7 and 9H9, Table I). PE-1 bound to the blocking antibody to P-Selectin (De Bruijni-Admiraal, L. G., et al., Blood 80: 134–142 (1992)) (AK-6, Table I), consistent with the localization of the epitope recognized by this mAb to the lectin domain of P-Selectin. By contrast, the nonblocking antibodies to P-Selectin, AC 1.2 and CRC 81, did not recognize PE-1 (Table I). This latter result is consistent with earlier studies which indicated a contribution of residues within the EGF and/or CR domains of P-Selectin in AC 1.2 binding (Jutila, M. A., et al., J. Exp. Med. 175: 1565–1573 (1992)). These results are consistent with the PE-1 chimera being correctly folded, and indicate that at least part of the epitope recognized by the blocking mAb AK-6 is localized to the lectin domain of P-Selectin.

To determine if transferring the P-Selectin lectin domain onto E-Selectin-IgG transferred carbohydrate specificity, we examined binding of PE-1 to various immobilized glycolipids. This binding was compared to that seen with either P-Selectin-IgG or E-Selectin-IgG. As shown in FIG. 11, the PE-1 chimera appeared to closely mimic P-Selectin-IgG in binding to all three glycolipids tested: 2'3 sLe$^x$ (FIG. 11A), 2'6 sLe$^x$ (FIG. 11B) and sulfatides (FIG. 11C). Therefore, the lectin domain of P-Selectin appears to be sufficient for transferring specificity in binding to these purified glycolipids.

Figure 12:
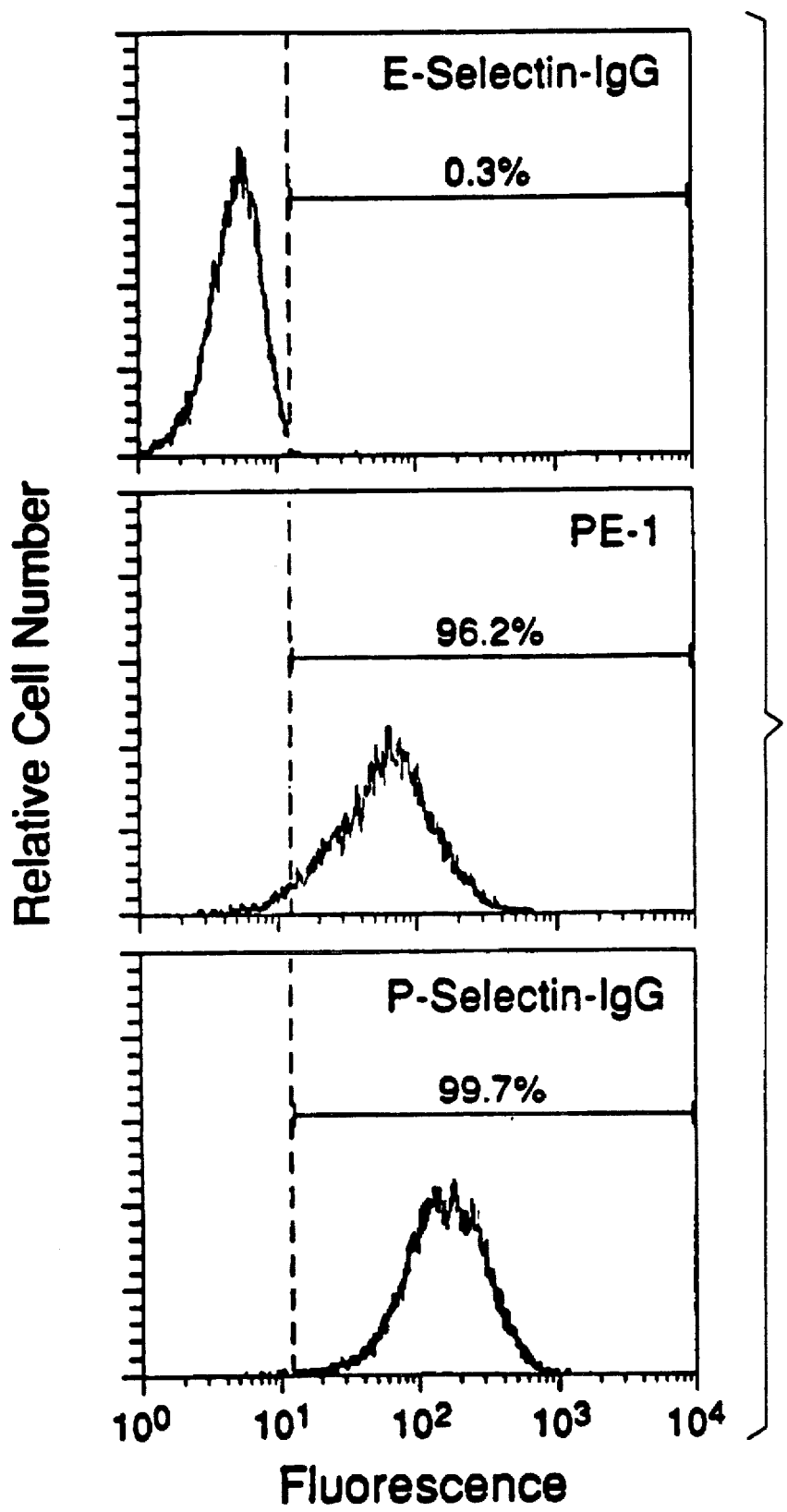

We then tested the PE-1 chimera for cell staining to see if the P-Selectin lectin domain could also confer the high affinity binding to the P-Selectin ligand on HL60 cells. As seen in FIG. 12, the PE-1 chimera did bind HL60 cells. However, the shift in fluorescence seen with PE-1 staining was not as great as that seen with P-Selectin-IgG (FIG. 12). Therefore, although the lectin domain of P-Selectin did appear to clearly confer HL60 cell staining, some contribution of the EGF and/or CR1 domain of P-Selectin may be required for full, high affinity binding to these cells. Similar results were seen when neutrophils were stained with these three chimeras (data not shown).

The above results using the PE-1 chimera indicated that the lectin domain of P-Selectin contained elements responsible for the differences in binding of E- and P-Selectin to immobilized glycolipids and cells. Therefore, we performed mutagenesis of the P-Selectin lectin domain to further localize the residues responsible for the interaction of P-Selectin with its ligand. P-Selectin mutagenesis was focused on those sites which in our previous study proved to be important for E-Selectin binding to its ligand. This strategy was followed for two reasons. First, as mentioned above, a wealth of experimental evidence exists indicating similarities in recognition of sugars by E- and P-Selectin. Thus, it is reasonable to suppose that a site important for E-Selectin-mediated adhesion would also participate in Selectin-mediated binding. The second reason derived from an experimental consideration. In the E-Selectin study we were able to generate an entire panel of antibodies to serve as structural controls for the effects of point mutations on lectin domain structure. This allowed the elimination of amino acid substitutions which grossly affected folding of the E-Selectin lectin domain from consideration. In this study, we were limited to just three anti-P-Selectin mAb's (AK-6, AC 1.2, CRC 81), only one of which (AK-6) was clearly shown to bind a determinant in the lectin domain (see above). To avoid the generation and analysis of mutants which do not bind ligand due to a gross conformational effect rather than a specific side chain substitution, we restricted our analysis to only those mutations which had resulted in correctly folded proteins in the E-Selectin analysis (Example 1).

Figure 13A:
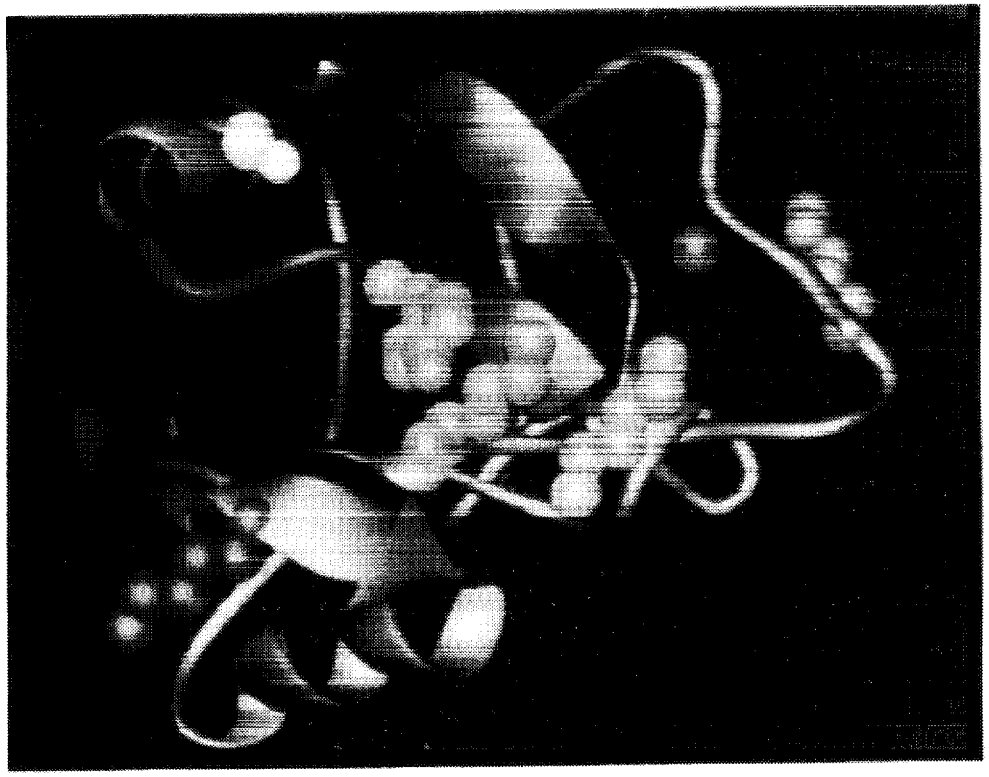
Figure 13B:
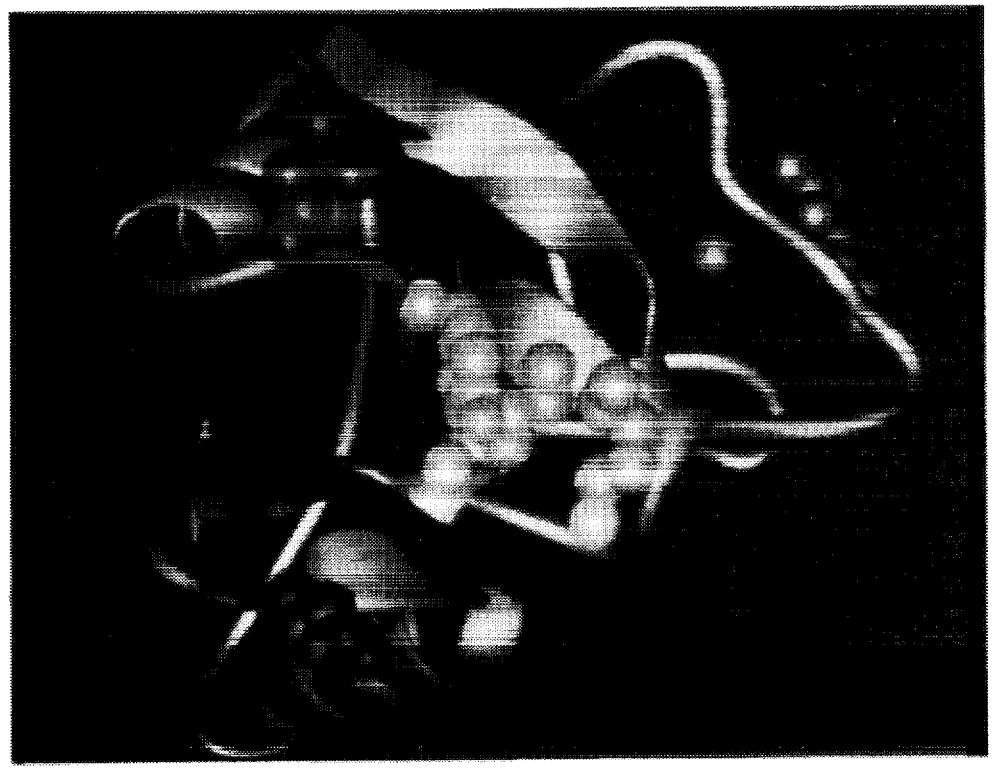
Figure 14:
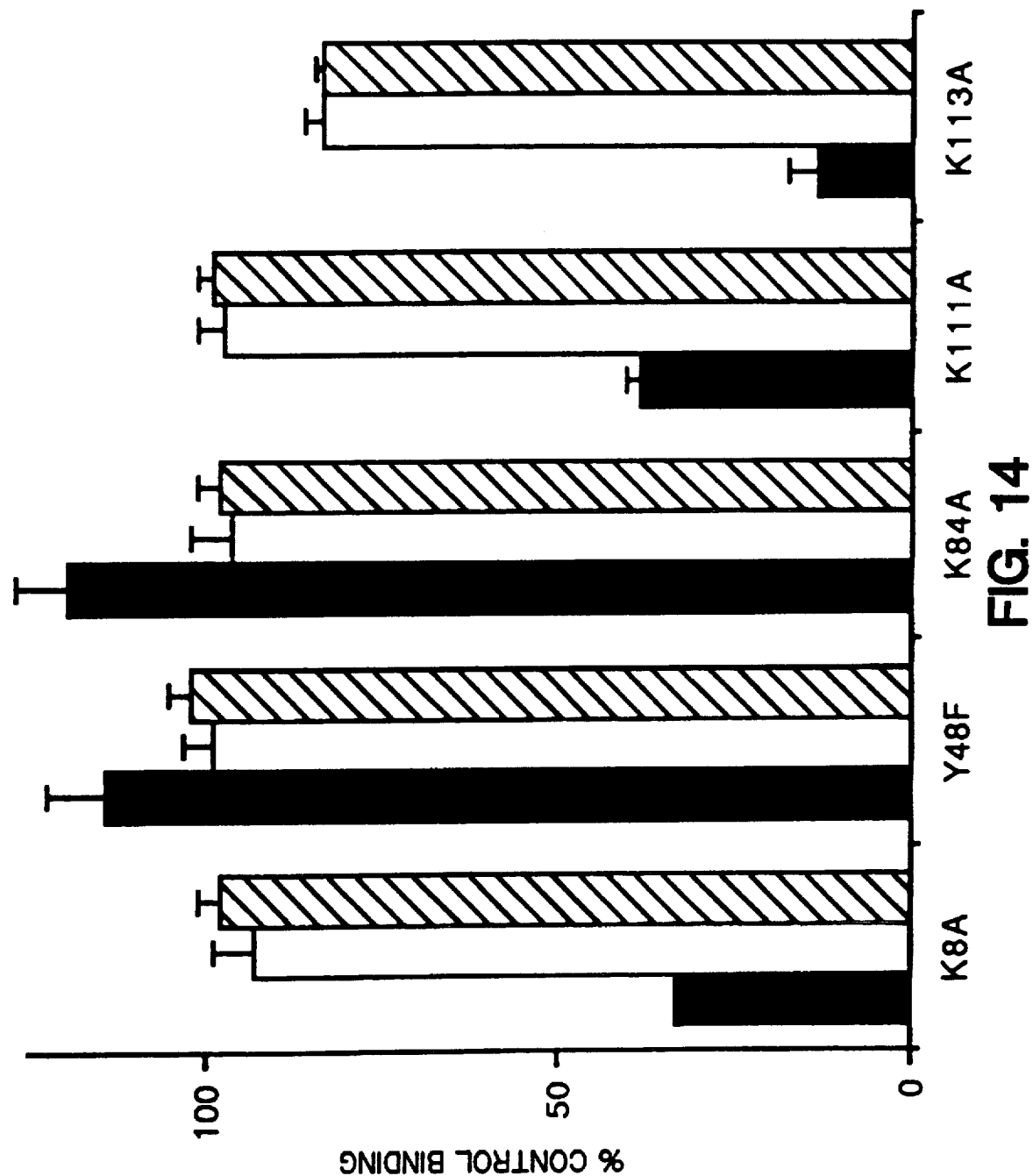
Figure 15A:
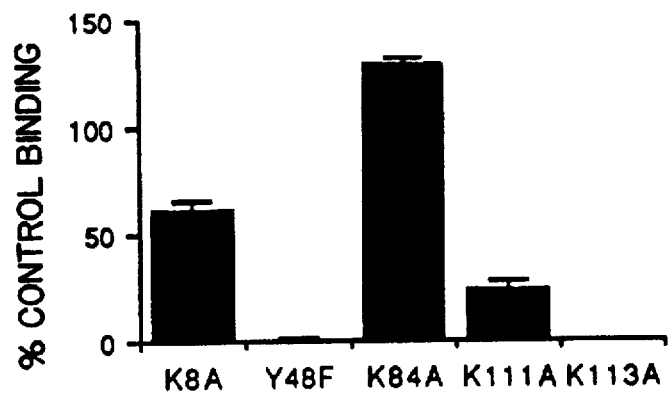
Figure 15B:
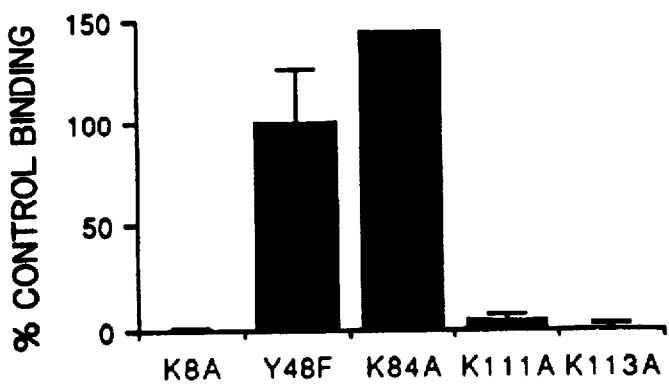
Figure 15C:
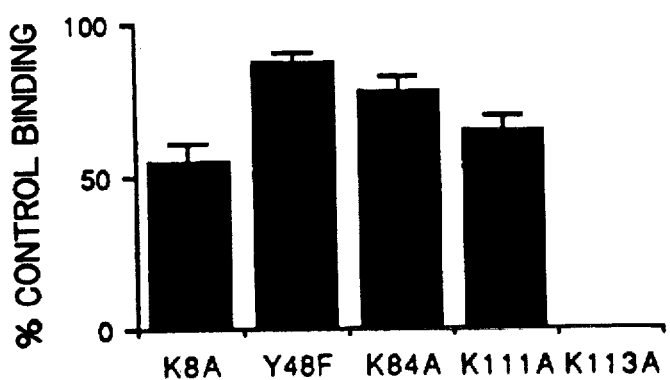
Figure 15D:
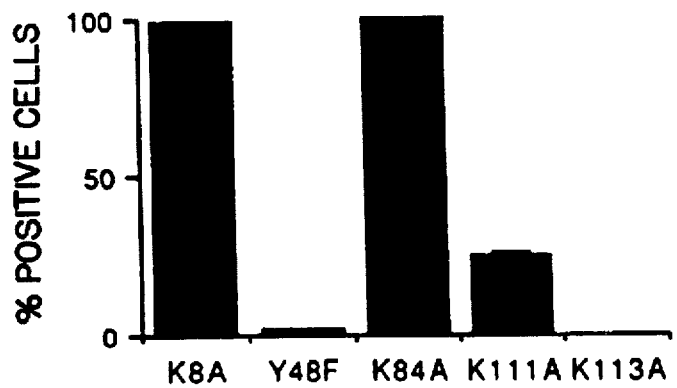
Figure 16A:
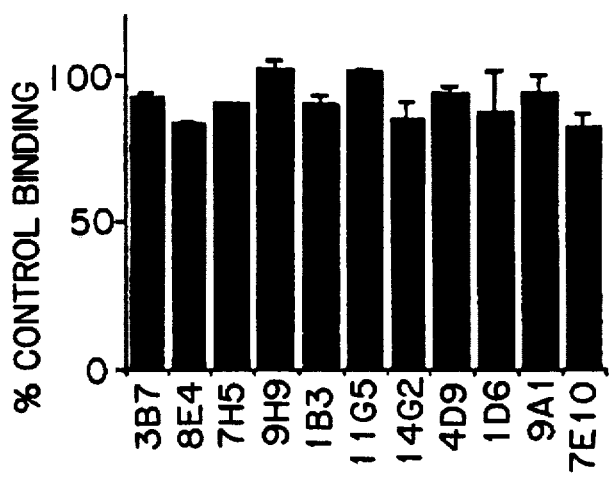
Figure 16B:
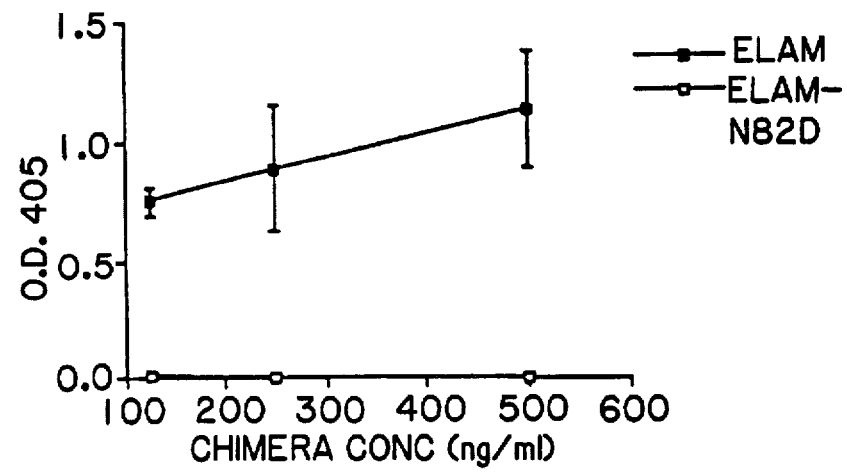
Figure 16C:
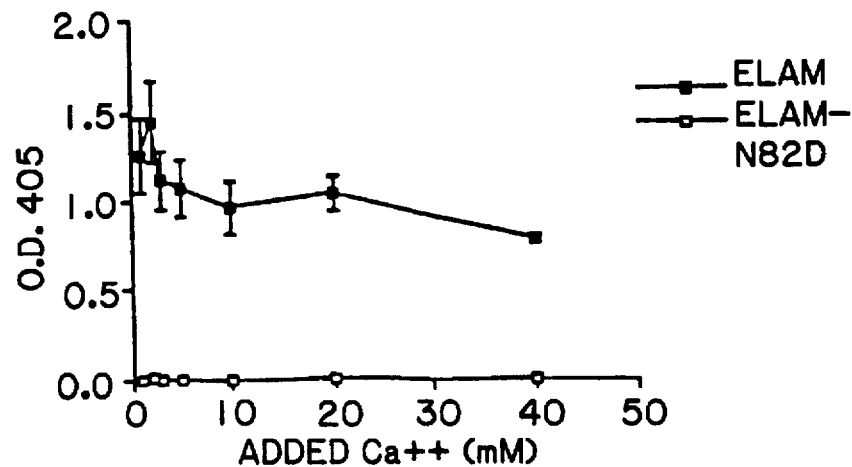

As a starting point for P-Selectin mutagenesis we generated a three dimensional model of the P-Selectin lectin domain in the same manner that the E-Selectin model was generated (see FIG. 13). Comparison of the two models revealed that of the residues that appeared most important for E-Selectin binding to 2'3 sLe$^x$, three are conserved in P-Selectin: Y48, K111 and K113. In E-Selectin, the substitutions Y48F, K111A and K113A each profoundly decreased sLe$^x$ binding. Mutation of position 84 from R to A did not affect sLe$^x$ binding by E-Selectin, and mutation of position 8 from E to A increased sLe$^x$ binding by E-Selectin. FIG. 14 shows the effect of complimentary substitutions at these positions in P-Selectin on the binding of the anti-P-Selectin mAb's. Whereas none of these substitutions significantly affected capture by the nonblocking antibodies (AC 1.2 and CRC 81), each of the substitutions K8A, K111A and K113A partially decreased binding of the blocking antibody AK-6 (FIG. 14). These results are consistent with the PE-1 chimera results above which localized part of the AK-6 epitope to the lectin domain of P-Selectin. These results are also consistent with the relatively close alignment of these three positions along the same face of the P-Selectin lectin domain, as predicted by the model (FIG. 13). Furthermore, the complimentary substitutions K8A and K113A in E-Selectin completely abolished binding of a number of blocking mAb's to E-Selectin. Also like E-Selectin, mutation of the residues at positions 48 and 84 in P-Selectin did not affect mAb binding (FIG. 14).

Next, we evaluated these P-Selectin mutants for binding to immobilized glycolipids and cells (FIG. 15). Measurement of the binding of this panel of mutants to the 2'3 sLe$^x$ glycolipid indicated that P-Selectin appears to use some of the same residues as E-Selectin in binding this carbohydrate (FIG. 15A). Whereas P-Selectin mutants with the substitutions K8A and K84A still bound 2'3 sLe$^x$, the mutants Y48F and K113A were completely negative. In E-Selectin the mutant K111A did not bind 2'3 sLe$^x$ at all. Here, however, the P-Selectin mutant K111A mediated partial binding to 2'3 sLe$^x$, perhaps indicating a subtle difference in recognition of this sugar by E- and P-Selectin. A different set of residues appeared to be important for binding to the 2'6 form of sLe$^x$ (FIG. 5B). The substitutions K8A, K111A and K113A ablated binding, while Y48F had no effect. The mutant K84A also still bound 2'6 sLe$^x$(FIG. 15B). When sulfatide binding was evaluated, a third pattern emerged (FIG. 15C). Only the mutation K113A significantly decreased sulfatide binding by P-Selectin. These results indicate that the same face of P-Selectin appears to participate in binding these three glycolipids, with subtle differences in the residues used to bind each sugar.

Since a more relevant assay for measuring P-Selectin interactions with its ligand is the cell binding assay, the panel of mutants was evaluated by flow cytometry for staining of HL60 cells (FIG. 14D). Interestingly, the binding pattern seen with cells closely mimics that seen with the immobilized glycolipid 2'3 sLe$^x$. K8A and K84A both bound to HL60 cells, Y48F and K113A did not, and K111A bound HL60 cells only partially. Similar reactivities were seen when neutrophils were stained (data not shown). So, mutation of residues within this pocket of P-Selectin also affected binding to its cognate ligand on cells. Furthermore, comparison of the reactivity of this panel of mutants with purified glycolipids provided some potential insights into the nature of the carbohydrate seen by P-Selectin (see Discussion).

In E-Selectin the arginine at position 97 was also important for sugar recognition. Mutation of this residue to alanine completely abolished E-Selectin/2'3 sLe$^x$ binding (Example 1). The residue at position 97 in P-Selectin is a serine and the above results indicated that P-Selectin appears to use the same region as E-Selectin in binding to its ligand. Therefore, we tested if this difference in residues at position 97 could account for the differences in ligand binding by E- and P-Selectin. Examination of the three dimensional models of the E- and P-Selectin lectin domains (FIG. 13) reveals that amino acid 97 falls within a loop formed by residues 94–100, which is an insertion in selectins relative to the mannose binding protein. The sequence of these two selectins is quite different through this stretch- YIKREKDV for E-Selectin vs. YIKSPSAP for P-Selectin- so these loops would be expected to have different conformations. To test the importance of the residue at position 97 in conferring specificity to selectins, we made a P-Selectin-IgG mutant with the 94–100 loop replaced with the corresponding residues from E-Selectin: S97R, P98E, S99K, A100D, P101V. We then tested this mutant (abbreviated REKDV) for binding to antibodies, glycolipids and cells. Binding of the P-Selectin-IgG REKDV mutant to each of the three anti-P-Selectin mAb's (AK-6, AC 1.2, and CRC 81) was approximately 70% of control P-Selectin-IgG binding. This would seem to indicate that although folding of this mutant is largely correct, some subtle structural perturbations may be present. Accordingly, this mutant did not bind any of the purified glycolipids (data not shown). However, the REKDV mutant did bind to HL60 cells, although its binding was significantly less than that seen with control P-Selectin-IgG (70% cells positive, MFI 290 for REKDV mutant vs. 97% cells positive, MFI 416 for control P-Selectin-IgG). Thus, transferring this loop (containing residue 97) from E-Selectin to P-Selectin did not completely disrupt the ability of the resultant P-selectin mutant to recognize its cellular ligand. These results would seem to imply that at least some of the differences in binding between E- and P-Selectin must be due to differences outside of this region (see Discussion).

Discussion

Research on selectin-carbohydrate interactions continues to be hampered by a lack of detailed understanding of the sugar structures seen by each adhesion molecule. However, results from a number of approaches, including direct binding studies, soluble carbohydrate inhibition studies, and structural and conformational analyses of purified potential ligands, have indicated commonalities in selectin recognition. Many of these findings have centered around the sLe$^x$ core structure. However, many of these proposed similarities may be artifacts of forced binding under experimentally manipulated circumstances (see Varki, A., Cur. Opin. Cell Biol. 4: 257–266 (1992) for discussion). In vitro assays with solid phase carbohydrate ligands and transfected, over expressed selectins can be misleading due to the unnaturally high densities of both receptors and ligands (Varki, A., Supra). Furthermore, unrelated sugars can inhibit the same lectin interaction due to structural mimicry (Varki, A., Supra). The flow cytometric assay employed here to measure P-Selectin's interactions with its cellular ligand should avoid most of these limitations while still being sensitive and convenient. The experiments presented here indicate that the measured binding observed using the P-Selectin-IgG chimera to stain cells accurately represents this interaction. Studies to date have shown that P-Selectin binds a single, possibly unique, major glycoprotein of 120 Kd (Cummings, R. D. et al., J. Cell Biol. 118: 445–456 (1992)). The same glycoprotein has been isolated from both neutrophils and HL60 cells (Cummings, R. D. et al., Supra) and the number of such binding sites for P-Selectin is estimated at 10,000–20,000 per cell (McEver, R. P. et al., J. Cell Biol. 112: 491–499 (1991), Cummings, R. D. et al., supra, Berndt, M. C., J. Biol. Chem. 266: 5371–5374 (1991)). sLe$^x$ probably forms some component of this glycoprotein ligand, and sLe$^x$ is sufficient to confer some P-Selectin binding. However, sLe$^x$ is not sufficient to confer the saturable, high affinity binding characteristic of P-Selectin adhesion (McEver, R. P. et al., Supra). Therefore, the P-Selectin ligand must have structural features in addition to sLe$^x$ that confer specificity and affinity (Cummings, R. D. et al., Supra; R. D. Cummings, J. Cell. Biol. 115: 557–564 (1991)).

The protein portion of the P-Selectin ligand may contribute to this specificity and affinity by: (a) presenting the sugar in the correct configuration, (b) presenting multivalent sugars to enhance binding avidity, and (c) participating in a protein/protein contact with P-Selectin (Cummings, R. D. et al., Supra). In fact, a role for presentation of polyvalent ligands to L-Selectin by the GlyCAM 1 ligand has already been proposed (Dowbenko, D. et al., Cell 69: 927–938 (1992)). In the assay described here, P-Selectin-IgG binding was ablated by protease treatment of cells, consistent with a requirement for this glycoprotein (Ahern, T. J. et al., J. Biol. Chem. 267: 11104–11110 (1992)). As noted above, sialic acid is crucial to P-Selectin binding and sialidase treatment also abolished binding. Most importantly, removal of calcium chelation by EGTA also led to a loss of binding, a result that is a signature of the biologically relevant interactions performed by all C-type lectins (Drickamer, K. et al., Supra). A suprising finding was that the E-Selectin-IgG chimera did not bind HL60 cells or neutrophils in this fluid phase staining assay. This is despite the fact that the E-Selectin carbohydrate ligand, sLe$^x$, is clearly expressed by these cells (Gaeta, F. C. A., Science 250: 1130–1132 (1990); Aruffo, A., Science 250: 1132–1135 (1990)). Furthermore, we and others (Alford, J. et al., J. Leuk. Biol, 52: 85–88 (1992)) have found that E-Selectin-IgG is capable of binding HL60 cells and neutrophils when the chimera is presented on a solid substrate, suggesting that the lack of binding in the fluid phase may be due to lower affinity of E-Selectin for its cognate cell surface ligand. Thus, E-Selectin and P-Selectin are clearly distinct in binding to cells both as soluble Ig chimeras, as well as when they are expressed on endothelial/platelet cell surfaces.

At least part of this difference between E- and P-Selectin must be due to differences in their lectin domains. Transferring the P-Selectin lectin domain onto the E-Selectin-IgG construct resulted in a molecule (PE-1) which stained cells, albeit at a lower intensity than P-Selectin-IgG. Carbohydrate reactivity was completely transferred with the relevant lectin domain. Thus, PE-1 reacted with the purified glycolipids in a manner that was indistinguishable from P-Selectin-IgG and quite distinct from E-Selectin-IgG. Therefore, the lectin domain of each selectin appears sufficient for determining the differences in reactivities with these relatively small sugars. This result is consistent with a study by Kansas et al. (Kansas, G. S., et al., *J. Cell Biol.* 114: 351–358 (1991)) in which domains of L- and P-Selectin were exchanged to show that PPME and fucoidin binding, both L-Selectin-specific carbohydrate ligands, as well as the epitope defined by blocking mAb LAM1-3, map at least in part to the C-terminal 67 amino acid residues of the L-Selectin lectin domain. These authors also demonstrated that the CR domains are not important for conferring PPME or fucoidin specificity (Kansas, G. S. et al., Supra). The EGF and CR domains of selectins have clearly been shown to perform vital structural roles for these receptors (Bowen, B. et al., *J. Cell. Biol.* 107: 1853–1862 (1990); Jutila, M. A. et al., *J. Exp. Med.* 175: 1565–1573 (1992); Aruffo, A. et al., *Science* 250: 1132–1135 (1990); Fennie, C. et al., *J. Cell. Biol.* 115: 235–243 (1991)). Whether these domains in P-Selectin also participate in making crucial contacts with its glycoprotein ligand cannot be answered here. However, the results of this study do place limitations on the nature of any such contacts. First, the P-Selectin-IgG chimera employed here only contains the lectin, EGF and CR1 domains of P-Selectin (Dowbenko, S. et al., Supra). Thus, CR2-CR9 must not form necessary contacts for the high affinity binding between P-Selectin and its ligand and it is interesting to note that mouse P-Selectin lacks the CR2 domain (Isenmann, S. et al., *J. Biol. Chem,* 267: 15176–15183 (1992). In addition, because the PE-1 chimera did bind cells, any potential protein/protein contact sites may map to the lectin domain of P-Selectin. The difference in staining between PE-1 and P-Selectin-IgG might reflect subtle conformational effects of the P- or E-Selectin EGF domains interacting with the common lectin domain. However, it is important to stress that protein/protein contacts mediated by the EGF or CR1 domains cannot be ruled out.

Two recent studies have identified regions of the P-Selectin lectin domain that may be important for cell adhesion. Geng and coworkers showed that a mAb capable of inhibiting neutrophil binding to P-Selectin mapped to residues 19–34 of this molecule, and that a peptide corresponding to this stretch also inhibited neutrophil binding to P-Selectin (Geng, J. G., et al., *J. Biol. Chem.* 256: 22313–22318 (1991)). This group described other peptides from the lectin domain of P-Selectin (corresponding to residues 23–30, 54–63, and 70–79) which blocked P-Selectin-mediated adhesion (Geng, J. G., et al., *J. Biol. Chem.*, "Lectin-domain peptides from selectins interact with both cell surface ligands and $Ca^{2+}$ ions," in press (1991). In the model of P-Selectin, these residues fall on the opposite side of the lectin domain from the site that we have identified as important for selectin-carbohydrate binding and cell adhesion (see FIG. 13 and Example 1). The residues characterized by Geng and co-workers may represent a second site in P-Selectin which may bind the carbohydrate and/or protein component of its ligand. In light of this, it is important to remember that the results with the REKDV mutant indicated that not all of the differences in specificity between E- and P-Selectin can be explained by the region identified in this study. Therefore, the possible co-operation of this site with those described by Geng et al. in conferring P-Selectin binding specificity warrants exploration.

The results presented here establish that the site previously identified as crucial for E-Selectin binding to 2'3 sLe$^x$ is also crucial to P-Selectin binding to this ligand. Mutations in two of the conserved residues within this site, Y48 and K113, completely abolished 2'3 sLe$^x$ binding and cell adhesion by both E- and P-Selectin. The anti-P-Selectin blocking mAb AK-6 mapped to this same site, as did all of the anti-E-Selectin blocking mAb's. Furthermore, Mel-14, a mAB that blocks L-Selectin-mediated adhesion in vitro and in vivo, maps to this region (Bowen, B. et al., Supra. The fact that adhesion blocking mABs to all three selectins bind to residues within this site emphasizes its importance to the adhesive functions of these proteins.

By comparing the binding of the panel of P-Selectin mutants to 2'3 sLe$^x$, 2'6 sLe$^x$ and sulfatides with their ability to bind cells, some insight as to the nature of the carbohydrate component of the P-Selectin ligand can be gained. As noted above, one study has shown that E- and P-Selectin have related but distinct carbohydrate specificities (Ahern, T. J., Supra). For example, these authors found that the interaction of E-Selectin with the sLe$^x$ component of the P-Selectin ligand precludes P-Selectin binding (Ahern, T. J., Supra). Using a 2'6 sialyl-specific lectin to block P-Selectin binding, they also proposed that the P-Selectin ligand may contain a bidentate carbohydrate structure with one arm containing 2'3 sLe$^x$ and the other a terminal sialyl-2'6 beta Gal (Dell, A., et al., *J. Biol. Chem.* 259: 10925–10935 (1984); Ahern, T. J., Supra). However, our results with the P-Selectin mutants would seem to question a role for 2'6 linked sialic acid in cell adhesion. The mutant K8A did not bind the 2'6 form of sLe$^x$ at all, but still bound the P-Selectin ligand on cells. Furthermore, the Y48F mutant did not bind cells at all, but still bound 2'6 sLe$^x$. Consequently, 2'6 sLe$^x$ binding did not correlate with ligand binding. However, the binding to 2'6 sLe$^x$ in the solid phase assays employed here is weak compared to 2'3 sLe$^x$ and sulfatide binding, so caution is warranted in interpreting these results. Thus, it is conceivable that presentation of the 2'6 sialylated carbohydrate to P-Selectin provides a critical parameter of ligand recognition that is not replicated in our solid phase assay (Dowbenko, D. et al., Supra).

A second binding activity of P-Selectin whose biological relavance has been recently questioned is its interaction with sulfatides. Sulfatide binding by P-Selectin is probably not relevant in vivo due to the observation that this interaction is not calcium dependent, that it is not removed by proteases, and that cells expressing sulfatides (erythrocytes and platelets) do not necessarily bind P-Selectin (R. D. Cummings, et al., *J. Cell. Biol.* 118: 445–456 (1992)). Also, sulfatide binding by the P-Selectin mutants studied here did not correlate with cell binding. For example, mutant Y48F bound sulfatides well but did not adhere to cells at all. Cell binding was only correlated with binding to 2'3 sLe$^x$. Each mutant which bound 2'3 sLe$^x$ bound cells (K8A and K84A), while those which did not bind 2'3 sLe$^x$ (Y48F and K113A) did not bind cells, and one mutant (K111A) showed partial binding to both 2'3 sLe$^x$ and cells. This is interesting given a recent study demonstrating that expression of 2'3 sLe$^x$ correlated with a cell's ability to bind activated platelets via P-Selectin (De bruijne-Admiraal, et al., Supra), and it is consistent with the mAB and carbohydrate blocking studies of Polley et al. (Hakomori, S. et al., *Proc. Natl. Acad. Sci. U.S.A.* 88: 6224–6228 (1991)).

Although one cannot rule out the involvement of 2'6 linked sialic acid or sulfatides in P-Selectin's interactions with its ligand, the data presented here clearly questions the role (if any) they may play. Specificity of binding between E- and P-Selectin may derive from the manner in which 2'3 sLe$^x$ is presented (i.e. glycolipid vs glycoprotein). However, it must be allowed that 2'3 sLe$^x$ may not be the naturally occurring carbohydrate ligand recognized by either selectin, and that these differences in selectin binding could be accounted for by subtle changes in the saccharide itself (Varki, A., Supra). Sulfatides, as well as the sulfated glycans heparin, fucoidin, and dextran sulfate, may inhibit P-Selectin function by mimicking its ligand (R. D. Cummings, et al., *J. Cell Biol.* 118: 445–456 (1992)). sLe$^x$, sulfated glycans, and sulfatides all have a negative charge which may play a role in the interaction of P-Selectin with its ligand (De bruijne-Admiraal et al., Supra; Example 1) and these sugars may inhibit selectin-mediated adhesion by binding to a common site (for example, at K113) which is important for P-Selectin/ligand interactions.

All citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

TABLE I

PE-1 Binding to Anti-selectin Antibodies

| mAb Class | Clone | P-selectin-IgG | O.D. 450 PE-1 | E-selectin-IgG |
|---|---|---|---|---|
| blocking mAb to P-selectin | AK-6 | 1.3 +/– 0.1 | 1.7 +/– 0.1 | 0.0 +/– 0.0 |
| nonblocking mAb to P-selectin | AC 1.2 | 2.8 +/– 0.1 | 0.1 +/– 0.0 | 0.0 +/– 0.0 |
|  | CRC81 | 3.1 +/– 0.1 | 0.1 +/– 0.0 | 0.0 +/– 0.0 |
| mAb to CR1 & CR2 of E-selectin | 9A1 | 0.1 +/–0.0 | 1.1 +/– 0.2 | 0.9 +/– 0.1 |
|  | 7E10 | 0.0 +/– 0.0 | 1.6 +/–0.0 | 1.2 +/– 0.2 |
| mAb to Lectin domain of E-selectin | 3B7 | 0.1 +/– 0.1 | 0.0 +/– 0.0 | 1.9 +/– 0.0 |
|  | 9H9 | 0.0 +/– 0.0 | 0.0 +/– 0.0 | 2.2 +/– 0.1 |

The P-selectin-IgG, E-selectin-IgG, and PE-1 chimeras were tested for capture by the antibodies indicated using the ELISA format described previously (10). Result shown are the mean optical density +/– SD of duplicate determinations.

EXAMPLE 4 cDNA sequences encoding the entire extracellular portion of human E-selectin (amino acids 1M to 532S) were fused to the carboxy terminal 37 amino acids of CD16 which contains the signal sequence for cell surface anchorage via a glycosylphosphatidylinositol linkage (GPI). The fusion construct was cloned into the plasmid vector pEF-Bos [Mizushima and Nagata, *Nucl. Acids Res.* 18, 5322 (1990)], and the GPI anchored E-selectin expressed under the control of the human EF-1alpha chromosomal promoter. Point mutations were introduced into this cDNA construct using standard oligonucleotide directed mutagenesis techniques, as described in Example 1. Transient expression in COS-7 cells was used to address the impact of each E-selectin mutation on structure/function.

The function of mutants E-selectins was determined by performing adhesion assays with human neutrophils as described in Example 3. The following mutations were found to abolish neutrophil binding without altering their recognition by the panel of Mabs: Y48F, Y94F, R97A, K111a, and K113A E-selectin. A mutation at position 105 (N105D) showed a marked reduction in binding of monoclonal antibodies specific for the lectin egf domain, suggesting a sever structural perturbation. In addition, E8A, and R84,K86A exhibited an increased neutrophil binding capacity. These results are in agreement with the results obtained by the sLex binding assay disclosed in Example 1.

We claim:

1. A human E-, L- or P-selectin variant which has an amino acid substituted at a site or sites selected from the group consisting of amino acid residues 7–9, 97, 111 and 113 of the lectin domain of the corresponding native human E-, L- or P-selectin SEQ. ID. NOs: 36, 38 and 39, respectively), and otherwise retains the sequence of the corresponding native human selectin, provided that said variant is other than a native selectin molecule.

2. The variant of claim 1 that is a human E- or L-Selectin variant and has an uncharged amino acid substituted for a charged amino acid at amino acid residue number 8 of the lectin domain of the corresponding native human E- or L-selectin.

3. The variant of claim 2 wherein the amino acid substituted is alanine, valine, serine or threonine.

4. The variant of claim 3 wherein the amino acid substituted is alanine.

5. The variant of claim 4 that is E8A E-Selectin, or K8A L-Selectin.

6. The variant of claim 1 having a positively charged amino acid at at least one of the amino acid positions 111 and 113 of the lectin domain of the corresponding native human selectin.

7. The variant of claim 6 having a positively charged amino acid at both of the amino acid positions 111 and 113.

8. The variant of claim 7 wherein said positively charged amino acid is lysine or arginine.

9. The variant of claim 8 having retained the native amino acids at positions 111 and 113 of the lectin domain of the corresponding native human selectin.

10. The variant of claim 7 that is an E- or L-Selectin variant and has a positively charged amino acid at each of the amino acid positions 97, 111 and 113 of the lectin domain of the corresponding native human selectin.

11. The variant of claim 10 having retained the native amino acids at positions 97, 111 and 113 of the corresponding native human selectin.

12. The variant of claim 1 having an uncharged amino acid substituted at at least one of the amino acid positions 111 and 113 of the lectin domain of the corresponding native selectin.

13. The variant of claim 12 wherein said uncharged amino acid is alanine.

14. An isolated DNA molecule encoding the variant of claim 1.

15. The DNA molecule of claim 14 encoding the variant of claim 2.

16. The DNA molecule of claim 14 encoding the variant of claim 5.

17. A replicable expression vector containing and capable, in a transformant host cell, of expressing the DNA molecule of claim 16.

18. A host cell transformed with the vector of claim 17.

19. The host cell of claim 18 that is eukaryotic.

20. The host cell of claim 18 that is mammalian.

21. A replicable expression vector containing and capable, in a transformant host cell, of expressing the DNA molecule of claim 14.

22. The DNA molecule of claim 14 encoding the variant of claim 12.

23. A replicable expression vector containing and capable, in a transformant host cell, of expressing the DNA molecule of claim 22.

24. A host cell transformed with the vector of claim 23.

25. The DNA molecule of claim 14 encoding the variant of claim 13.

\* \* \* \* \*

UNITED STATES PATENT AND TRADEMARK OFFICE
CERTIFICATE OF CORRECTION

PATENT NO. : 5,593,882
DATED : January 14, 1997
INVENTOR(S) : Erbe, D. et al.

Page 1 of 1

It is certified that error appears in the above-identified patent and that said Letters Patent is hereby corrected as shown below:

Claim 1,
Line 5, before "SEQ.", insert --(--.

Claim 18,
Line 1, delete "claim 17" and insert therefor --claim 21--.

Signed and Sealed this

Twenty-sixth Day of June, 2001

*Attest:*

*Attesting Officer*

NICHOLAS P. GODICI
*Acting Director of the United States Patent and Trademark Office*